US007959928B2

(12) United States Patent
Bachmann et al.

(10) Patent No.: US 7,959,928 B2
(45) Date of Patent: Jun. 14, 2011

(54) VLP-ANTIGEN CONJUGATES AND THEIR USES AS VACCINES

(75) Inventors: Martin F. Bachmann, Seuzach (CH); Karl G. Proba, Zürich (CH); Patrik Maurer, Winterthur (CH); Edwin Meijerink, Zürich (CH); Katrin Schwarz, Schlieren (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 8 days.

(21) Appl. No.: 11/664,716

(22) PCT Filed: Oct. 5, 2005

(86) PCT No.: PCT/EP2005/055009
§ 371 (c)(1),
(2), (4) Date: Apr. 5, 2007

(87) PCT Pub. No.: WO2006/037787
PCT Pub. Date: Apr. 13, 2006

(65) Prior Publication Data
US 2008/0095738 A1   Apr. 24, 2008

Related U.S. Application Data

(60) Provisional application No. 60/615,637, filed on Oct. 5, 2004.

(30) Foreign Application Priority Data

Jun. 14, 2005   (EP) .................................... 05105228

(51) Int. Cl.
*A61K 39/00*   (2006.01)
*C12N 7/00*   (2006.01)
(52) U.S. Cl. .................................. 424/204.1; 435/235.1
(58) Field of Classification Search ........................ None
See application file for complete search history.

(56) References Cited

U.S. PATENT DOCUMENTS

| | | |
|---|---|---|
| 4,950,599 A | 8/1990 | Bertling |
| 5,534,257 A | 7/1996 | Mastico et al. |
| 5,698,424 A | 12/1997 | Mastico et al. |
| 6,159,728 A | 12/2000 | Stockley et al. |
| 6,251,678 B1 | 6/2001 | Volkin et al. |
| 6,932,971 B2 | 8/2005 | Bachmann et al. |
| 6,964,769 B2 | 11/2005 | Sebbel et al. |
| 7,094,409 B2 | 8/2006 | Bachmann et al. |
| 7,115,266 B2 | 10/2006 | Bachmann |
| 7,128,911 B2 | 10/2006 | Bachmann et al. |
| 7,138,252 B2 | 11/2006 | Bachmann et al. |
| 7,264,810 B2 | 9/2007 | Renner et al. |
| 7,279,165 B2 | 10/2007 | Bachmann et al. |
| 7,320,793 B2 | 1/2008 | Renner et al. |
| 2003/0091593 A1 | 5/2003 | Bachmann et al. |
| 2003/0099668 A1 | 5/2003 | Bachmann et al. |
| 2003/0175290 A1 | 9/2003 | Renner et al. |
| 2004/0005338 A1 | 1/2004 | Bachmann et al. |
| 2004/0076645 A1 | 4/2004 | Bachmann et al. |
| 2004/0136962 A1 | 7/2004 | Renner et al. |
| 2005/0191317 A1 | 9/2005 | Bachmann et al. |
| 2006/0088550 A1 | 4/2006 | Bachmann et al. |
| 2006/0204475 A1 | 9/2006 | Bachmann et al. |
| 2006/0210588 A1 | 9/2006 | Bachmann et al. |
| 2006/0251623 A1 | 11/2006 | Bachmann et al. |
| 2006/0251677 A1 | 11/2006 | Bachmann et al. |
| 2007/0184068 A1 | 8/2007 | Renner et al. |
| 2007/0248617 A1 | 10/2007 | Bachmann et al. |

FOREIGN PATENT DOCUMENTS

| | | |
|---|---|---|
| EP | 0 648 272 B1 | 10/1997 |
| EP | 0 572 433 B1 | 5/2001 |
| EP | 0 591 369 B1 | 9/2001 |
| WO | WO 00/23955 A1 | 4/2000 |
| WO | WO 00/32227 A2 | 6/2000 |
| WO | WO 03/024480 A2 | 3/2003 |
| WO | WO 03/024481 A2 | 3/2003 |
| WO | WO 04/000351 A1 | 12/2003 |
| WO | WO 2004/009124 A2 | 1/2004 |
| WO | WO 2004/084939 A2 | 10/2004 |
| WO | WO 2004/084940 A1 | 10/2004 |
| WO | WO 2004/085635 A1 | 10/2004 |
| WO | WO 2005/004907 A1 | 1/2005 |
| WO | WO 2005/048918 A2 | 6/2005 |

(Continued)

OTHER PUBLICATIONS

Abreu, M.T. and Arditi, M., "Innate Immunity and Toll-like Receptors: Clinical Implications of Basic Science Research," *J Pediatr.* 144:421-429, Elsevier Science (Apr. 2004).

Bachmann, M.F. and Zinkernagel, R.M., "The Influence of Virus Structure on Antibody Responses and Virus Serotype Formation," *Immunol. Today* 17:553-558, Elsevier Science (1996).

Bancroft, J.B., et al., "The Self-Assembly of a Nucleic-Acid Free Pseudo-Top Component for a Small Spherical Virus," *Virology* 36:146-149, Academic Press (1968).

Bancroft, J.B., et al., "The Effects of Various Polyanions on Shell Formation of Some Spherical Viruses," *Virology* 39:924-930, Academic Press (1968).

(Continued)

*Primary Examiner* — Stacy B. Chen
*Assistant Examiner* — Nicole Kinsey White
(74) *Attorney, Agent, or Firm* — Sterne, Kessler, Goldstein & Fox P.L.L.C.

(57) ABSTRACT

The present invention is related to the fields of molecular biology, virology, immunology and medicine. The invention provides a composition comprising a virus-like particle (VLP) of an RNA-bacteriophage and at least one antigen, wherein the VLP is recombinantly produced in a host, and wherein the amount of host RNA with secondary structure comprised by the VLP is at most 20% of the amount of host RNA with secondary structure originally comprised by the VLP; and wherein the VLP and the at least one antigen are linked with one another. The invention also provides methods for producing the compositions of the invention. The compositions of the invention are useful in the production of vaccines for the treatment of diseases, disorders and conditions. Furthermore, the compositions of the invention are particularly useful to efficiently induce strong antibody responses against the antigen within the indicated context while lowering or eliminating unwanted T cell responses.

32 Claims, 5 Drawing Sheets

FOREIGN PATENT DOCUMENTS

| WO | WO 2005/068639 A2 | 7/2005 |
|----|-------------------|--------|
| WO | WO 2005/108425 A1 | 11/2005 |
| WO | WO 2005/117963 A1 | 12/2005 |
| WO | WO 2006/027300 A2 | 3/2006 |
| WO | WO 2006/032674 A1 | 3/2006 |
| WO | WO 2007/144150 A1 | 12/2007 |

OTHER PUBLICATIONS

Beckett, D., et al., "Roles of Operator and Non-Operator RNA Sequences in Bacteriophage R17 Capsid Assembly," *J. Mol. Biol.* 204:939-947, Academic Press (1988).

Chackerian, B., et al., "Induction of Autoantibodies to Mouse CCR5 with Recombinant Papillomavirus Particles," *Proc. Natl. Acad. Sci. USA* 96:2373-2378, National Academy of Sciences (1999).

Diebold, S., et al., "Innate Antiviral Responses by Means of TLR7-Mediated Recognition of Single-Stranded RNA," *Science* 303:1529-1531, American Association for the Advancement of Science (Mar. 2004).

Fehr, T., et al., "T Cell-Independent Type I Antibody Response Against B cell Epitopes Expressed Repetitively on Recombinant Virus Particles," *Proc. Natl. Acad. Sci. USA* 95:9477-9481, National Academy of Sciences (1998).

Heal, K.G., et al., "Expression and Immunogenicity of a Liver Stage Malaria Epitope Presented as a Foreign Peptide on the Surface of RNA-Free MS2 Bacteriophage Capsids," *Vaccine* 18:251-258, Elsevier Science (2000).

Heil, F., et al., "Species-Specific Recognition of Single-Stranded RNA via Toll-like Receptor 7 and 8," *Science* 303:1526-1529, American Association for the Advancement of Science (Mar. 2004).

Hohn, T., "The Assembly of Protein Particles of the RNA Bacteriophage fr in Absence of RNA," *Biochem. Biophys. Res. Commun.* 36:7-17, Elsevier Science (1969).

Hohn, T., "Role of RNA in the Assembly Process of Bacteriophage fr," *J. Mol. Biol.* 43:191-200, Elsevier Science (1969).

Kopp, E. and Medzhitov, R., "Recognition of Microbial Infection by Toll-like Receptors," *Curr. Opin. Immunol.* 15:396-401, Elsevier Science (2003).

Kozlovska, T., et al., "RNA Phage Qβ Coat Protein as a Carrier for Foreign Epitopes," *Intervirology* 39:9-15, S. Karger AG Basel (1996).

Mastico, R.A., et al., "Multiple Presentation of Foreign Peptides on the Surface of an RNA-Free Spherical Bacteriophage Capsid," *J. Gen. Virol.* 74:541-548, The Society for General Microbiology (1993).

Rohrmann, G.F. and Krueger, R.G., "The Self-Assembly of RNA Free Protein Subunits from Bacteriophage MS-2," *Biochem. Biophys. Res. Commun.* 38:406-413, Elsevier Science (1970).

Schwarz, K., et al., "Role of Toll-like Receptors in Costimulating Cytotoxic T cell Responses," *Eur. J. Immunol.* 33:1465-1470, Wiley-VCH Verlag GmbH (2003).

Storni, T., et al., "Nonmethylated CG Motifs Packaged into Virus-like Particles Induce Protective Cytotoxic T Cell Responses in the Absence of Systemic Side Effects," *J. Immunol.* 172:1777-1785, American Association of Immunologists (Feb. 2004).

Vasiljeva, I., et al., "Mosaic Qβ Coats as a New Presentation Model," *FEBS Lett.* 431:7-11, Federation of European Biochemical Societies (1998).

Yang, T., et al., "Alternative Splicing of the Human Cholesteryl Ester Transfer Protein Gene in Transgenic Mice. Exon Exclusion Modulates Gene Expression in Response to Dietary or Developmental Change," *J. Biol. Chem.* 271:12603-2609, The American Society for Biochemistry and Molecular Biology (1996).

Yang, Y., et al., "Persistent Toll-like Receptor Signals are Required for Reversal of Regulatory T Cell-Mediated CD8 Tolerance," *Nat. Immunol.* 5:508-515, Nature Publishing Group (Apr. 2004).

Zhang, D., et al., "A Toll-like Receptor that Prevents Infection by Uropathogenic Bacteria," *Science* 303:1522-1526, American Association for the Advancement of Science (Mar. 2004).

```
                        SEQUENCE LISTING

<160> NUMBER OF SEQ ID NOS: 125

<210> SEQ ID NO 1
<211> LENGTH: 10
<212> TYPE: PRT
<213> ORGANISM: Unknown
<220> FEATURE:
<223> OTHER INFORMATION: Mammalian

<400> SEQUENCE: 1

Glu His Trp Ser Tyr Gly Leu Arg Pro Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: GnRH analogue CGG-GnRH

<400> SEQUENCE: 2

Cys Gly Gly Glu His Trp Ser Tyr Gly Leu Arg Pro Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: GnRH analogue GnRH-GGC

<400> SEQUENCE: 3

Glu His Trp Ser Tyr Gly Leu Arg Pro Gly Gly Gly Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: GnRH analogue C-GnRH

<400> SEQUENCE: 4

Cys Glu His Trp Ser Tyr Gly Leu Arg Pro Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: GnRH analogue GnRH-C

<400> SEQUENCE: 5

Glu His Trp Ser Tyr Gly Leu Arg Pro Gly Cys
1               5                   10

<210> SEQ ID NO 6
<211> LENGTH: 189
<212> TYPE: PRT
```

<213> ORGANISM: Homo sapiens

<400> SEQUENCE: 6

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 7
<211> LENGTH: 170
<212> TYPE: PRT
<213> ORGANISM: Homo sapiens

<400> SEQUENCE: 7

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 8
<211> LENGTH: 20
<212> TYPE: PRT
<213> ORGANISM: Homo sapiens

<400> SEQUENCE: 8

Gln Cys Gln Gln Leu Ser Gln Lys Leu Cys Thr Leu Ala Trp Ser Ala
1               5                   10                  15

His Pro Leu Val
            20

<210> SEQ ID NO 9
<211> LENGTH: 21
<212> TYPE: PRT
<213> ORGANISM: Homo sapiens

<400> SEQUENCE: 9

Leu Pro Asp Ser Pro Val Ala Gln Leu His Ala Ser Leu Leu Gly Leu
1               5                   10                  15

Ser Gln Leu Leu Gln
            20

<210> SEQ ID NO 10
<211> LENGTH: 132
<212> TYPE: PRT
<213> ORGANISM: Bacteriophage Q-beta

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 11
<211> LENGTH: 329
<212> TYPE: PRT
<213> ORGANISM: Bacteriophage Q-beta

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
        50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
               100                 105                 110

Leu Ala Ala Leu Leu Ala Ser Pro Leu Leu Ile Asp Ala Ile Asp Gln
           115                 120                 125

Leu Asn Pro Ala Tyr Trp Thr Leu Leu Ile Ala Gly Gly Gly Ser Gly
130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
               180                 185                 190

Val Glu Leu Gln Pro Arg Glu Phe Asp Val Ala Leu Lys Asp Leu Leu
           195                 200                 205

Gly Asn Thr Lys Trp Arg Asp Trp Asp Ser Arg Leu Ser Tyr Thr Thr
210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
               260                 265                 270

Lys Ser Ile Asn Ala Tyr Cys Ser Leu Ser Asp Ile Ala Ala Tyr His
           275                 280                 285

Ala Asp Gly Val Ile Val Gly Phe Trp Arg Asp Pro Ser Ser Gly Gly
290                 295                 300

Ala Ile Pro Phe Asp Phe Thr Lys Phe Asp Lys Thr Lys Cys Pro Ile
305                 310                 315                 320

Gln Ala Val Ile Val Pro Arg Ala
                325

<210> SEQ ID NO 12
<211> LENGTH: 129
<212> TYPE: PRT
<213> ORGANISM: Bacteriophage R17

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
 50                  55                  60

Pro Lys Val Ala Thr Gln Thr Val Gly Gly Val Glu Leu Pro Val Ala
 65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Asn Ser Gly Ile
        115                 120                 125

Tyr

<210> SEQ ID NO 13
<211> LENGTH: 130
<212> TYPE: PRT
<213> ORGANISM: Bacteriophage fr

<400> SEQUENCE: 13

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 14
<211> LENGTH: 130
<212> TYPE: PRT
<213> ORGANISM: Bacteriophage GA

<400> SEQUENCE: 14

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

```
<210> SEQ ID NO 15
<211> LENGTH: 132
<212> TYPE: PRT
<213> ORGANISM: Bacteriophage SP

<400> SEQUENCE: 15

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 16
<211> LENGTH: 329
<212> TYPE: PRT
<213> ORGANISM: Bacteriophage SP

<400> SEQUENCE: 16

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205
```

```
Gly Asn Thr Asn Trp Arg Asn Trp Asp Gln Arg Leu Ser Asp Tyr Asp
    210                 215                 220

Ile Ala Asn Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 17
<211> LENGTH: 130
<212> TYPE: PRT
<213> ORGANISM: Bacteriophage MS2

<400> SEQUENCE: 17

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 18
<211> LENGTH: 133
<212> TYPE: PRT
<213> ORGANISM: Bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60
```

```
Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ser Asp Val Thr Phe Ser
                 85                  90                  95

Phe Thr Gln Tyr Ser Thr Val Glu Glu Arg Ala Leu Val Arg Thr Glu
                100                 105                 110

Leu Gln Ala Leu Leu Ala Asp Pro Met Leu Val Asn Ala Ile Asp Asn
            115                 120                 125

Leu Asn Pro Ala Tyr
        130

<210> SEQ ID NO 19
<211> LENGTH: 133
<212> TYPE: PRT
<213> ORGANISM: Bacteriophage MX1

<400> SEQUENCE: 19

Met Ala Lys Leu Gln Ala Ile Thr Leu Ser Gly Ile Gly Lys Asn Gly
 1               5                  10                  15

Asp Val Thr Leu Asn Leu Asn Pro Arg Gly Val Asn Pro Thr Asn Gly
             20                  25                  30

Val Ala Ala Leu Ser Glu Ala Gly Ala Val Pro Ala Leu Glu Lys Arg
         35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ala Asp Val Thr Phe Ser
                 85                  90                  95

Phe Thr Gln Tyr Ser Thr Asp Glu Glu Arg Ala Leu Val Arg Thr Glu
                100                 105                 110

Leu Lys Ala Leu Leu Ala Asp Pro Met Leu Ile Asp Ala Ile Asp Asn
            115                 120                 125

Leu Asn Pro Ala Tyr
        130

<210> SEQ ID NO 20
<211> LENGTH: 330
<212> TYPE: PRT
<213> ORGANISM: Bacteriophage NL95

<400> SEQUENCE: 20

Met Ala Lys Leu Asn Lys Val Thr Leu Thr Gly Ile Gly Lys Ala Gly
 1               5                  10                  15

Asn Gln Thr Leu Thr Leu Thr Pro Arg Gly Val Asn Pro Thr Asn Gly
             20                  25                  30

Val Ala Ser Leu Ser Glu Ala Gly Ala Val Pro Ala Leu Glu Lys Arg
         35                  40                  45

Val Thr Val Ser Val Ala Gln Pro Ser Arg Asn Arg Lys Asn Tyr Lys
 50                  55                  60

Val Gln Ile Lys Leu Gln Asn Pro Thr Ala Cys Thr Lys Asp Ala Cys
 65                  70                  75                  80

Asp Pro Ser Val Thr Arg Ser Gly Ser Arg Asp Val Thr Leu Ser Phe
                 85                  90                  95

Thr Ser Tyr Ser Thr Glu Arg Glu Arg Ala Leu Ile Arg Thr Glu Leu
                100                 105                 110

Ala Ala Leu Leu Lys Asp Asp Leu Ile Val Asp Ala Ile Asp Asn Leu
```

```
                        115                 120                 125
Asn Pro Ala Tyr Trp Ala Ala Leu Leu Ala Ala Ser Pro Gly Gly Gly
            130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 21
<211> LENGTH: 129
<212> TYPE: PRT
<213> ORGANISM: Bacteriophage f2

<400> SEQUENCE: 21

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 22
<211> LENGTH: 128
<212> TYPE: PRT
<213> ORGANISM: Bacteriophage PP7
```

```
<400> SEQUENCE: 22

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 23
<211> LENGTH: 132
<212> TYPE: PRT
<213> ORGANISM: Artificial Sequence
<220> FEATURE:
<223> OTHER INFORMATION: Bacteriophage Qbeta 240 mutant

<400> SEQUENCE: 23

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 24
<211> LENGTH: 132
<212> TYPE: PRT
<213> ORGANISM: Artificial Sequence
<220> FEATURE:
<223> OTHER INFORMATION: Bacteriophage Q-beta 243 mutant

<400> SEQUENCE: 24

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30
```

```
Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
 50                      55                  60

Gln Val Lys Ile Gln Asn Pro Thr Ala Cys Thr Ala Asn Gly Ser Cys
 65                  70                  75                  80

Asp Pro Ser Val Thr Arg Gln Lys Tyr Ala Asp Val Thr Phe Ser Phe
                    85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
            130
```

<210> SEQ ID NO 25
<211> LENGTH: 132
<212> TYPE: PRT
<213> ORGANISM: Artificial Sequence
<220> FEATURE:
<223> OTHER INFORMATION: Bacteriophage Q-beta 250 mutant

<400> SEQUENCE: 25

```
Ala Arg Leu Glu Thr Val Thr Leu Gly Asn Ile Gly Arg Asp Gly Lys
 1               5                  10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
 50                      55                  60

Gln Val Lys Ile Gln Asn Pro Thr Ala Cys Thr Ala Asn Gly Ser Cys
 65                  70                  75                  80

Asp Pro Ser Val Thr Arg Gln Lys Tyr Ala Asp Val Thr Phe Ser Phe
                    85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
            130
```

<210> SEQ ID NO 26
<211> LENGTH: 132
<212> TYPE: PRT
<213> ORGANISM: Artificial Sequence
<220> FEATURE:
<223> OTHER INFORMATION: Bacteriophage Q-beta 251 mutant

<400> SEQUENCE: 26

```
Ala Lys Leu Glu Thr Val Thr Leu Gly Asn Ile Gly Lys Asp Gly Arg
 1               5                  10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
 50                      55                  60
```

```
Gln Val Lys Ile Gln Asn Pro Thr Ala Cys Thr Ala Asn Gly Ser Cys
 65                  70                  75                  80

Asp Pro Ser Val Thr Arg Gln Lys Tyr Ala Asp Val Thr Phe Ser Phe
                 85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 27
<211> LENGTH: 132
<212> TYPE: PRT
<213> ORGANISM: Artificial Sequence
<220> FEATURE:
<223> OTHER INFORMATION: Bacteriophage Q-beta 259 mutant

<400> SEQUENCE: 27

Ala Arg Leu Glu Thr Val Thr Leu Gly Asn Ile Gly Lys Asp Gly Arg
 1               5                  10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
 65                  70                  75                  80

Asp Pro Ser Val Thr Arg Gln Lys Tyr Ala Asp Val Thr Phe Ser Phe
                 85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 28
<211> LENGTH: 10
<212> TYPE: PRT
<213> ORGANISM: Artificial Sequence
<220> FEATURE:
<223> OTHER INFORMATION: GnRH analogue GnRH 1Q-10

<400> SEQUENCE: 28

Gln His Trp Ser Tyr Gly Leu Arg Pro Gly
 1               5                  10

<210> SEQ ID NO 29
<211> LENGTH: 131
<212> TYPE: PRT
<213> ORGANISM: bacteriophage AP205

<400> SEQUENCE: 29

Met Ala Asn Lys Pro Met Gln Pro Ile Thr Ser Thr Ala Asn Lys Ile
 1               5                  10                  15

Val Trp Ser Asp Pro Thr Arg Leu Ser Thr Thr Phe Ser Ala Ser Leu
                20                  25                  30

Leu Arg Gln Arg Val Lys Val Gly Ile Ala Glu Leu Asn Asn Val Ser
```

```
                35                  40                  45
Gly Gln Tyr Val Ser Val Tyr Lys Arg Pro Ala Pro Lys Pro Glu Gly
        50                  55                  60

Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 30
<211> LENGTH: 20
<212> TYPE: PRT
<213> ORGANISM: Artificial Sequence
<220> FEATURE:
<223> OTHER INFORMATION: GnRH analogue tandem sequence

<400> SEQUENCE: 30

Glu His Trp Ser Tyr Gly Leu Arg Pro Gly Glu His Trp Ser Tyr Gly
 1               5                  10                  15

Leu Arg Pro Gly
            20

<210> SEQ ID NO 31
<211> LENGTH: 20
<212> TYPE: PRT
<213> ORGANISM: Artificial Sequence
<220> FEATURE:
<223> OTHER INFORMATION: GnRH analogue tandem sequence

<400> SEQUENCE: 31

Glu His Trp Ser Tyr Gly Leu Arg Pro Gly Gln His Trp Ser Tyr Gly
 1               5                  10                  15

Leu Arg Pro Gly
            20

<210> SEQ ID NO 32
<211> LENGTH: 20
<212> TYPE: PRT
<213> ORGANISM: Artificial Sequence
<220> FEATURE:
<223> OTHER INFORMATION: GnRH analogue tandem sequence

<400> SEQUENCE: 32

Gln His Trp Ser Tyr Gly Leu Arg Pro Gly Gln His Trp Ser Tyr Gly
 1               5                  10                  15

Leu Arg Pro Gly
            20

<210> SEQ ID NO 33
<211> LENGTH: 14
<212> TYPE: PRT
<213> ORGANISM: Homo sapiens

<400> SEQUENCE: 33

Phe Tyr Glu Lys Leu Leu Gly Ser Asp Ile Phe Thr Gly Glu
 1               5                  10
```

```
<210> SEQ ID NO 34
<211> LENGTH: 22
<212> TYPE: PRT
<213> ORGANISM: Homo sapiens

<400> SEQUENCE: 34

Phe Tyr Glu Lys Leu Leu Gly Ser Asp Ile Phe Thr Gly Glu Pro Ser
1               5                   10                  15

Leu Leu Pro Asp Ser Pro
            20

<210> SEQ ID NO 35
<211> LENGTH: 17
<212> TYPE: PRT
<213> ORGANISM: Homo sapiens

<400> SEQUENCE: 35

Val Ala Gln Leu His Ala Ser Leu Leu Gly Leu Ser Gln Leu Leu Gln
1               5                   10                  15

Pro

<210> SEQ ID NO 36
<211> LENGTH: 27
<212> TYPE: PRT
<213> ORGANISM: Homo sapiens

<400> SEQUENCE: 36

Gly Glu Pro Ser Leu Leu Pro Asp Ser Pro Val Ala Gln Leu His Ala
1               5                   10                  15

Ser Leu Leu Gly Leu Ser Gln Leu Leu Gln Pro
            20                  25

<210> SEQ ID NO 37
<211> LENGTH: 19
<212> TYPE: PRT
<213> ORGANISM: Homo sapiens

<400> SEQUENCE: 37

Pro Glu Gly His His Trp Glu Thr Gln Gln Ile Pro Ser Leu Ser Pro
1               5                   10                  15

Ser Gln Pro

<210> SEQ ID NO 38
<211> LENGTH: 8
<212> TYPE: PRT
<213> ORGANISM: Homo sapiens

<400> SEQUENCE: 38

Pro Ser Leu Leu Pro Asp Ser Pro
1               5

<210> SEQ ID NO 39
<211> LENGTH: 7
<212> TYPE: PRT
<213> ORGANISM: Homo sapiens

<400> SEQUENCE: 39

Leu Pro Asp Ser Pro Val Ala
1               5

<210> SEQ ID NO 40
<211> LENGTH: 39
<212> TYPE: PRT
<213> ORGANISM: Homo sapiens
```

<400> SEQUENCE: 40

Phe Tyr Glu Lys Leu Leu Gly Ser Asp Ile Phe Thr Gly Glu Pro Ser
1               5                   10                  15

Leu Leu Pro Asp Ser Pro Val Ala Gln Leu His Ala Ser Leu Leu Gly
            20                  25                  30

Leu Ser Gln Leu Leu Gln Pro
        35

<210> SEQ ID NO 41
<211> LENGTH: 6
<212> TYPE: PRT
<213> ORGANISM: Homo sapiens

<400> SEQUENCE: 41

Leu Leu Pro Asp Ser Pro
1               5

<210> SEQ ID NO 42
<211> LENGTH: 28
<212> TYPE: PRT
<213> ORGANISM: Homo sapiens

<400> SEQUENCE: 42

Leu Leu Gly Ser Asp Ile Phe Thr Gly Glu Pro Ser Leu Leu Pro Asp
1               5                   10                  15

Ser Pro Val Ala Gln Leu His Ala Ser Leu Leu Gly
            20                  25

<210> SEQ ID NO 43
<211> LENGTH: 32
<212> TYPE: PRT
<213> ORGANISM: Home sapiens

<400> SEQUENCE: 43

Phe Tyr Glu Lys Leu Leu Gly Ser Asp Ile Phe Thr Gly Glu Pro Ser
1               5                   10                  15

Leu Leu Pro Asp Ser Pro Val Ala Gln Leu His Ala Ser Leu Leu Gly
            20                  25                  30

<210> SEQ ID NO 44
<211> LENGTH: 7
<212> TYPE: PRT
<213> ORGANISM: Homo sapiens

<400> SEQUENCE: 44

Gln Pro Glu Gly His His Trp
1               5

<210> SEQ ID NO 45
<211> LENGTH: 25
<212> TYPE: PRT
<213> ORGANISM: artificial sequence
<220> FEATURE:
<223> OTHER INFORMATION: homology sequence between TNF-superfamily
      members

<400> SEQUENCE: 45

Lys Pro Ala Ala His Leu Val Gly Lys Pro Leu Gly Gln Gly Pro Leu
1               5                   10                  15

Ser Trp Glu Asn Asp Gly Gly Thr Ala
            20                  25

<210> SEQ ID NO 46
<211> LENGTH: 113
<212> TYPE: PRT
<213> ORGANISM: Mus musculus

<400> SEQUENCE: 46

Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Gly Thr Val Glu
    50                  55                  60

Met Leu Phe Gln Asn Leu Ser Leu Ile Lys Lys Tyr Ile Asp Arg Gln
65                  70                  75                  80

Lys Glu Lys Cys Gly Glu Glu Arg Arg Arg Thr Arg Gln Phe Leu Asp
                85                  90                  95

Tyr Leu Gln Glu Phe Leu Gly Val Met Ser Thr Glu Trp Ala Met Glu
            100                 105                 110

Gly

<210> SEQ ID NO 47
<211> LENGTH: 115
<212> TYPE: PRT
<213> ORGANISM: Homo sapiens

<400> SEQUENCE: 47

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 48
<211> LENGTH: 17
<212> TYPE: PRT
<213> ORGANISM: artificial sequecne
<220> FEATURE:
<223> OTHER INFORMATION: N-terminal gamma 3 linker

<400> SEQUENCE: 48

Cys Gly Gly Pro Lys Pro Ser Thr Pro Pro Gly Ser Ser Gly Gly Ala
1               5                   10                  15

Pro

<210> SEQ ID NO 49
<211> LENGTH: 9

```
<212> TYPE: PRT
<213> ORGANISM: artificial sequence
<220> FEATURE:
<223> OTHER INFORMATION: gastrin fragment 1-9

<400> SEQUENCE: 49

Glu Gly Pro Trp Leu Glu Glu Glu Glu
1               5

<210> SEQ ID NO 50
<211> LENGTH: 17
<212> TYPE: PRT
<213> ORGANISM: Homo sapiens

<400> SEQUENCE: 50

Glu Gly Pro Trp Leu Glu Glu Glu Glu Ala Tyr Gly Trp Met Asp
1               5                   10                  15

Phe

<210> SEQ ID NO 51
<211> LENGTH: 18
<212> TYPE: PRT
<213> ORGANISM: Homo sapiens

<400> SEQUENCE: 51

Glu Gly Pro Trp Leu Glu Glu Glu Glu Ala Tyr Gly Trp Met Asp
1               5                   10                  15

Phe Gly

<210> SEQ ID NO 52
<211> LENGTH: 34
<212> TYPE: PRT
<213> ORGANISM: Homo sapiens

<400> SEQUENCE: 52

Glu Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

<210> SEQ ID NO 53
<211> LENGTH: 35
<212> TYPE: PRT
<213> ORGANISM: Homo sapiens

<400> SEQUENCE: 53

Glu Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe Gly
        35

<210> SEQ ID NO 54
<211> LENGTH: 21
<212> TYPE: PRT
<213> ORGANISM: artificial sequence
<220> FEATURE:
<223> OTHER INFORMATION: gastrin CCG1-17G

<400> SEQUENCE: 54

Cys Gly Gly Glu Gly Pro Trp Leu Glu Glu Glu Glu Ala Tyr Gly
```

```
                1               5                   10                  15
Trp Met Asp Phe Gly
                20

<210> SEQ ID NO 55
<211> LENGTH: 9
<212> TYPE: PRT
<213> ORGANISM: Mus musculus

<400> SEQUENCE: 55

Arg Pro Pro Gly Phe Ser Pro Phe Arg
1               5

<210> SEQ ID NO 56
<211> LENGTH: 8
<212> TYPE: PRT
<213> ORGANISM: Mus musculus

<400> SEQUENCE: 56

Arg Pro Pro Gly Phe Ser Pro Phe
1               5

<210> SEQ ID NO 57
<211> LENGTH: 74
<212> TYPE: PRT
<213> ORGANISM: Homo sapiens

<400> SEQUENCE: 57

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly Arg
65                  70

<210> SEQ ID NO 58
<211> LENGTH: 82
<212> TYPE: PRT
<213> ORGANISM: Mus musculus

<400> SEQUENCE: 58

Cys Gly Ser Gly Gly Asn Leu His Leu Leu Arg Gln Lys Ile Glu Glu
1               5                   10                  15

Gln Ala Ala Lys Tyr Lys His Ser Val Pro Lys Lys Cys Cys Tyr Asp
                20                  25                  30

Gly Ala Arg Val Asn Phe Tyr Glu Thr Cys Glu Glu Arg Val Ala Arg
            35                  40                  45

Val Thr Ile Gly Pro Leu Cys Ile Arg Ala Phe Asn Glu Cys Cys Thr
        50                  55                  60

Ile Ala Asn Lys Ile Arg Lys Glu Ser Pro His Lys Pro Val Gln Leu
65                  70                  75                  80

Gly Arg

<210> SEQ ID NO 59
<211> LENGTH: 20
<212> TYPE: PRT
<213> ORGANISM: Homo sapiens
```

<400> SEQUENCE: 59

Cys Val Val Ala Ser Gln Leu Arg Ala Asn Ile Ser His Lys Asp Met
1               5                   10                  15

Gln Leu Gly Arg
            20

<210> SEQ ID NO 60
<211> LENGTH: 352
<212> TYPE: PRT
<213> ORGANISM: Homo sapiens

<400> SEQUENCE: 60

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 61
<211> LENGTH: 12
<212> TYPE: PRT
<213> ORGANISM: artificial sequence
<220> FEATURE:
<223> OTHER INFORMATION: CCR5 ECL2A cyclic

<400> SEQUENCE: 61

Cys Arg Ser Gln Lys Glu Gly Leu His Tyr Thr Gly
1               5                   10

<210> SEQ ID NO 62
<211> LENGTH: 10
<212> TYPE: PRT
<213> ORGANISM: artificial sequence
<220> FEATURE:
<223> OTHER INFORMATION: CCR5 ECL2A

<400> SEQUENCE: 62

Arg Ser Gln Lys Glu Gly Leu His Tyr Thr
1               5                   10

<210> SEQ ID NO 63
<211> LENGTH: 31
<212> TYPE: PRT
<213> ORGANISM: artificial sequence
<220> FEATURE:
<223> OTHER INFORMATION: CCR5 PNt

<400> SEQUENCE: 63

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg
            20                  25                  30

<210> SEQ ID NO 64
<211> LENGTH: 352
<212> TYPE: PRT
<213> ORGANISM: Homo sapiens

<400> SEQUENCE: 64

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

```
Gln Arg Pro Arg Lys Leu Leu Ala Glu Lys Val Val Tyr Val Gly Val
145                 150                 155                 160

Trp Ile Pro Ala Leu Leu Thr Ile Pro Asp Phe Ile Phe Ala Asn
            165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 65
<211> LENGTH: 10
<212> TYPE: PRT
<213> ORGANISM: artificial sequence
<220> FEATURE:
<223> OTHER INFORMATION: CXCR4 176-185

<400> SEQUENCE: 65

Asn Val Ser Glu Ala Asp Asp Arg Tyr Ile
1               5                   10

<210> SEQ ID NO 66
<211> LENGTH: 39
<212> TYPE: PRT
<213> ORGANISM: artificial sequence
<220> FEATURE:
<223> OTHER INFORMATION: CXCR4 1-39

<400> SEQUENCE: 66

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile
        35

<210> SEQ ID NO 67
<211> LENGTH: 170
<212> TYPE: PRT
<213> ORGANISM: artificial sequence
<220> FEATURE:
<223> OTHER INFORMATION: mouse TNF his and cys containing linker at the
      N terminus
```

```
<400> SEQUENCE: 67

Met Gly Cys Gly Gly His His His His His Gly Ser Leu Arg
1               5                   10                  15

Ser Ser Ser Gln Asn Ser Asp Lys Pro Val Ala His Val Val Ala
            20                  25                  30

Asn His Gln Val Glu Glu Gln Leu Glu Trp Leu Ser Gln Arg Ala Asn
            35                  40                  45

Ala Leu Leu Ala Asn Gly Met Asp Leu Lys Asp Asn Gln Leu Val Val
        50                  55                  60

Pro Ala Asp Gly Leu Tyr Leu Val Tyr Ser Gln Val Leu Phe Lys Gly
65                  70                  75                  80

Gln Gly Cys Pro Asp Tyr Val Leu Leu Thr His Thr Val Ser Arg Phe
                85                  90                  95

Ala Ile Ser Tyr Gln Glu Lys Val Asn Leu Leu Ser Ala Val Lys Ser
                100                 105                 110

Pro Cys Pro Lys Asp Thr Pro Glu Gly Ala Glu Leu Lys Pro Trp Tyr
            115                 120                 125

Glu Pro Ile Tyr Leu Gly Gly Val Phe Gln Leu Glu Lys Gly Asp Gln
130                 135                 140

Leu Ser Ala Glu Val Asn Leu Pro Lys Tyr Leu Asp Phe Ala Glu Ser
145                 150                 155                 160

Gly Gln Val Tyr Phe Gly Val Ile Ala Leu
                165                 170

<210> SEQ ID NO 68
<211> LENGTH: 476
<212> TYPE: PRT
<213> ORGANISM: Homo sapiens

<400> SEQUENCE: 68

Cys Ser Lys Gly Thr Ser His Glu Ala Gly Ile Val Cys Arg Ile Thr
1               5                   10                  15

Lys Pro Ala Leu Leu Val Leu Asn His Glu Thr Ala Lys Val Ile Gln
            20                  25                  30

Thr Ala Phe Gln Arg Ala Ser Tyr Pro Asp Ile Thr Gly Glu Lys Ala
        35                  40                  45

Met Met Leu Leu Gly Gln Val Lys Tyr Gly Leu His Asn Ile Gln Ile
    50                  55                  60

Ser His Leu Ser Ile Ala Ser Ser Gln Val Glu Leu Val Glu Ala Lys
65                  70                  75                  80

Ser Ile Asp Val Ser Ile Gln Asn Val Ser Val Val Phe Lys Gly Thr
                85                  90                  95

Leu Lys Tyr Gly Tyr Thr Thr Ala Trp Trp Leu Gly Ile Asp Gln Ser
            100                 105                 110

Ile Asp Phe Glu Ile Asp Ser Ala Ile Asp Leu Gln Ile Asn Thr Gln
        115                 120                 125

Leu Thr Cys Asp Ser Gly Arg Val Arg Thr Ala Pro Asp Cys Tyr
    130                 135                 140

Leu Ser Phe His Lys Leu Leu His Leu Gln Gly Glu Arg Glu Pro
145                 150                 155                 160

Gly Trp Ile Lys Gln Leu Phe Thr Asn Phe Ile Ser Phe Thr Leu Lys
                165                 170                 175

Leu Val Leu Lys Gly Gln Ile Cys Lys Glu Ile Asn Val Ile Ser Asn
            180                 185                 190

Ile Met Ala Asp Phe Val Gln Thr Arg Ala Ala Ser Ile Leu Ser Asp
```

Gly Asp Ile Gly Val Asp Ile Ser Leu Thr Gly Asp Pro Val Ile Thr
    195                 200                 205
                210                 215                 220

Ala Ser Tyr Leu Glu Ser His His Lys Gly His Phe Ile Tyr Lys Asn
225                 230                 235                 240

Val Ser Glu Asp Leu Pro Leu Pro Thr Phe Ser Pro Thr Leu Leu Gly
                245                 250                 255

Asp Ser Arg Met Leu Tyr Phe Trp Phe Ser Glu Arg Val Phe His Ser
                260                 265                 270

Leu Ala Lys Val Ala Phe Gln Asp Gly Arg Leu Met Leu Ser Leu Met
                275                 280                 285

Gly Asp Glu Phe Lys Ala Val Leu Glu Thr Trp Gly Phe Asn Thr Asn
                290                 295                 300

Gln Glu Ile Phe Gln Glu Val Val Gly Gly Phe Pro Ser Gln Ala Gln
305                 310                 315                 320

Val Thr Val His Cys Leu Lys Met Pro Lys Ile Ser Cys Gln Asn Lys
                325                 330                 335

Gly Val Val Val Asn Ser Ser Val Met Val Lys Phe Leu Phe Pro Arg
                340                 345                 350

Pro Asp Gln Gln His Ser Val Ala Tyr Thr Phe Glu Glu Asp Ile Val
                355                 360                 365

Thr Thr Val Gln Ala Ser Tyr Ser Lys Lys Lys Leu Phe Leu Ser Leu
                370                 375                 380

Leu Asp Phe Gln Ile Thr Pro Lys Thr Val Ser Asn Leu Thr Glu Ser
385                 390                 395                 400

Ser Ser Glu Ser Ile Gln Ser Phe Leu Gln Ser Met Ile Thr Ala Val
                405                 410                 415

Gly Ile Pro Glu Val Met Ser Arg Leu Glu Val Val Phe Thr Ala Leu
                420                 425                 430

Met Asn Ser Lys Gly Val Ser Leu Phe Asp Ile Ile Asn Pro Glu Ile
                435                 440                 445

Ile Thr Arg Asp Gly Phe Leu Leu Leu Gln Met Asp Phe Gly Phe Pro
                450                 455                 460

Glu His Leu Leu Val Asp Phe Leu Gln Ser Leu Ser
465                 470                 475

<210> SEQ ID NO 69
<211> LENGTH: 16
<212> TYPE: PRT
<213> ORGANISM: artificial sequence
<220> FEATURE:
<223> OTHER INFORMATION: CETP 461-476

<400> SEQUENCE: 69

Phe Gly Phe Pro Glu His Leu Leu Val Asp Phe Leu Gln Ser Leu Ser
1               5                   10                  15

<210> SEQ ID NO 70
<211> LENGTH: 82
<212> TYPE: PRT
<213> ORGANISM: artificial sequence
<220> FEATURE:
<223> OTHER INFORMATION: CGSGG mouse C5a

<400> SEQUENCE: 70

Cys Gly Ser Gly Gly Asn Leu His Leu Arg Gln Lys Ile Glu Glu
1               5                   10                  15

Gln Ala Ala Lys Tyr Lys His Ser Val Pro Lys Lys Cys Cys Tyr Asp

```
                 20                  25                  30

Gly Ala Arg Val Asn Phe Tyr Glu Thr Cys Glu Arg Val Ala Arg
         35                  40                  45

Val Thr Ile Gly Pro Leu Cys Ile Arg Ala Phe Asn Glu Cys Cys Thr
     50                  55                  60

Ile Ala Asn Lys Ile Arg Lys Glu Ser Pro His Lys Pro Val Gln Leu
65                  70                  75                  80

Gly Arg

<210> SEQ ID NO 71
<211> LENGTH: 22
<212> TYPE: PRT
<213> ORGANISM: artificial sequence
<220> FEATURE:
<223> OTHER INFORMATION: CGG mouse C5a59-77

<400> SEQUENCE: 71

Cys Gly Gly Thr Ile Ala Asn Lys Ile Arg Lys Glu Ser Pro His Lys
1               5                   10                  15

Pro Val Gln Leu Gly Arg
            20

<210> SEQ ID NO 72
<211> LENGTH: 16
<212> TYPE: PRT
<213> ORGANISM: artificial sequence
<220> FEATURE:
<223> OTHER INFORMATION: G17(1-9)C2

<400> SEQUENCE: 72

Glu Gly Pro Trp Leu Glu Glu Glu Glu Ser Ser Pro Pro Pro Pro Cys
1               5                   10                  15

<210> SEQ ID NO 73
<211> LENGTH: 20
<212> TYPE: PRT
<213> ORGANISM: artificial sequence
<220> FEATURE:
<223> OTHER INFORMATION: c1G17

<400> SEQUENCE: 73

Glu Gly Pro Trp Leu Glu Glu Glu Glu Ala Tyr Gly Trp Met Asp
1               5                   10                  15

Phe Gly Gly Cys
            20

<210> SEQ ID NO 74
<211> LENGTH: 20
<212> TYPE: PRT
<213> ORGANISM: artificial sequence
<220> FEATURE:
<223> OTHER INFORMATION: nG17amide
<220> FEATURE:
<221> NAME/KEY: misc_feature
<222> LOCATION: (20)..(20)
<223> OTHER INFORMATION: F is amidated

<400> SEQUENCE: 74

Cys Gly Gly Gln Gly Pro Trp Leu Glu Glu Glu Glu Ala Tyr Gly
1               5                   10                  15

Trp Met Asp Phe
            20

<210> SEQ ID NO 75
```

```
<211> LENGTH: 37
<212> TYPE: PRT
<213> ORGANISM: artificial sequence
<220> FEATURE:
<223> OTHER INFORMATION: nG34amide

<400> SEQUENCE: 75

Cys Gly Gly Gln Leu Gly Pro Gln Gly Pro Pro His Leu Val Ala Asp
1               5                   10                  15

Pro Ser Lys Lys Gln Gly Pro Trp Leu Glu Glu Glu Glu Ala Tyr
            20                  25                  30

Gly Trp Met Asp Phe
        35

<210> SEQ ID NO 76
<211> LENGTH: 38
<212> TYPE: PRT
<213> ORGANISM: artificial sequence
<220> FEATURE:
<223> OTHER INFORMATION: nG34-G

<400> SEQUENCE: 76

Cys Gly Gly Gln Leu Gly Pro Gln Gly Pro Pro His Leu Val Ala Asp
1               5                   10                  15

Pro Ser Lys Lys Gln Gly Pro Trp Leu Glu Glu Glu Glu Ala Tyr
            20                  25                  30

Gly Trp Met Asp Phe Gly
        35

<210> SEQ ID NO 77
<211> LENGTH: 6
<212> TYPE: PRT
<213> ORGANISM: artificial sequence
<220> FEATURE:
<223> OTHER INFORMATION: human ghrelin 1-6

<400> SEQUENCE: 77

Gly Ser Ser Phe Leu Ser
1               5

<210> SEQ ID NO 78
<211> LENGTH: 7
<212> TYPE: PRT
<213> ORGANISM: artificial sequence
<220> FEATURE:
<223> OTHER INFORMATION: human ghrelin 1-7

<400> SEQUENCE: 78

Gly Ser Ser Phe Leu Ser Pro
1               5

<210> SEQ ID NO 79
<211> LENGTH: 8
<212> TYPE: PRT
<213> ORGANISM: artificial sequence
<220> FEATURE:
<223> OTHER INFORMATION: human ghrelin 1-8

<400> SEQUENCE: 79

Gly Ser Ser Phe Leu Ser Pro Glu
1               5

<210> SEQ ID NO 80
<211> LENGTH: 10
<212> TYPE: PRT
<213> ORGANISM: Homo sapiens
```

```
<400> SEQUENCE: 80

Lys Arg Pro Pro Gly Phe Ser Pro Phe Arg
1               5                   10

<210> SEQ ID NO 81
<211> LENGTH: 9
<212> TYPE: PRT
<213> ORGANISM: Homo sapiens

<400> SEQUENCE: 81

Lys Arg Pro Pro Gly Phe Ser Pro Phe
1               5

<210> SEQ ID NO 82
<211> LENGTH: 14
<212> TYPE: PRT
<213> ORGANISM: artificial sequence
<220> FEATURE:
<223> OTHER INFORMATION: human ghrelin 1-14

<400> SEQUENCE: 82

Gly Ser Ser Phe Leu Ser Pro Glu His Gln Arg Val Gln Gln
1               5                   10

<210> SEQ ID NO 83
<211> LENGTH: 13
<212> TYPE: PRT
<213> ORGANISM: artificial sequence
<220> FEATURE:
<223> OTHER INFORMATION: dog ghrelin 1-13

<400> SEQUENCE: 83

Gly Ser Ser Phe Leu Ser Pro Glu His Gln Lys Leu Gln
1               5                   10

<210> SEQ ID NO 84
<211> LENGTH: 13
<212> TYPE: PRT
<213> ORGANISM: artificial sequence
<220> FEATURE:
<223> OTHER INFORMATION: cat ghrelin 1-13

<400> SEQUENCE: 84

Gly Ser Ser Phe Leu Ser Pro Glu His Gln Lys Val Gln
1               5                   10

<210> SEQ ID NO 85
<211> LENGTH: 10
<212> TYPE: PRT
<213> ORGANISM: artificial sequence
<220> FEATURE:
<223> OTHER INFORMATION: human ghrelin 1-10

<400> SEQUENCE: 85

Gly Ser Ser Phe Leu Ser Pro Glu His Gln
1               5                   10

<210> SEQ ID NO 86
<211> LENGTH: 42
<212> TYPE: PRT
<213> ORGANISM: artificial sequence
<220> FEATURE:
<223> OTHER INFORMATION: human Ab 1-42

<400> SEQUENCE: 86

Asp Ala Glu Phe Arg His Asp Ser Gly Tyr Glu Val His His Gln Lys
```

-continued

```
                1               5                  10                  15
Leu Val Phe Phe Ala Glu Asp Val Gly Ser Asn Lys Gly Ala Ile Ile
                    20                  25                  30

Gly Leu Met Val Gly Gly Val Val Ile Ala
            35                  40

<210> SEQ ID NO 87
<211> LENGTH: 6
<212> TYPE: PRT
<213> ORGANISM: artificial sequence
<220> FEATURE:
<223> OTHER INFORMATION: human Ab1-6

<400> SEQUENCE: 87

Asp Ala Glu Phe Arg His
1               5

<210> SEQ ID NO 88
<211> LENGTH: 20
<212> TYPE: PRT
<213> ORGANISM: artificial sequence
<220> FEATURE:
<223> OTHER INFORMATION: human TNF 4-23

<400> SEQUENCE: 88

Ser Ser Arg Thr Pro Ser Asp Lys Pro Val Ala His Val Val Ala Asn
1               5                  10                  15

Pro Gln Ala Glu
            20

<210> SEQ ID NO 89
<211> LENGTH: 20
<212> TYPE: PRT
<213> ORGANISM: artificial sequence
<220> FEATURE:
<223> OTHER INFORMATION: mouse TNF 4-23

<400> SEQUENCE: 89

Ser Ser Gln Asn Ser Ser Asp Lys Pro Val Ala His Val Val Ala Asn
1               5                  10                  15

His Gln Val Glu
            20

<210> SEQ ID NO 90
<211> LENGTH: 11
<212> TYPE: PRT
<213> ORGANISM: artificial sequence
<220> FEATURE:
<223> OTHER INFORMATION: mouse TNF 22-32

<400> SEQUENCE: 90

Val Glu Glu Gln Leu Glu Trp Leu Ser Gln Arg
1               5                  10

<210> SEQ ID NO 91
<211> LENGTH: 11
<212> TYPE: PRT
<213> ORGANISM: artificial sequence
<220> FEATURE:
<223> OTHER INFORMATION: human TNF 22-32

<400> SEQUENCE: 91

Ala Glu Gly Gln Leu Gln Trp Leu Asn Arg Arg
1               5                  10
```

```
<210> SEQ ID NO 92
<211> LENGTH: 4
<212> TYPE: PRT
<213> ORGANISM: artificial sequence
<220> FEATURE:
<223> OTHER INFORMATION: AP205 spacer 1

<400> SEQUENCE: 92

Gly Ser Gly Gly
1

<210> SEQ ID NO 93
<211> LENGTH: 3
<212> TYPE: PRT
<213> ORGANISM: artificial sequence
<220> FEATURE:
<223> OTHER INFORMATION: AP205 spacer 2

<400> SEQUENCE: 93

Gly Ser Gly
1

<210> SEQ ID NO 94
<211> LENGTH: 8
<212> TYPE: PRT
<213> ORGANISM: artificial sequence
<220> FEATURE:
<223> OTHER INFORMATION: AP205 spacer 3

<400> SEQUENCE: 94

Gly Thr Ala Gly Gly Gly Ser Gly
1               5

<210> SEQ ID NO 95
<211> LENGTH: 11
<212> TYPE: PRT
<213> ORGANISM: artificial sequence
<220> FEATURE:
<223> OTHER INFORMATION: AP205 spacer 4

<400> SEQUENCE: 95

Gly Ser Gly Thr Ala Gly Gly Gly Ser Gly Ser
1               5                   10

<210> SEQ ID NO 96
<211> LENGTH: 3
<212> TYPE: PRT
<213> ORGANISM: artificial sequence
<220> FEATURE:
<223> OTHER INFORMATION: linker 1

<400> SEQUENCE: 96

Cys Gly Gly
1

<210> SEQ ID NO 97
<211> LENGTH: 10
<212> TYPE: PRT
<213> ORGANISM: artificial sequence
<220> FEATURE:
<223> OTHER INFORMATION: gamma linker 1

<400> SEQUENCE: 97

Cys Gly Asp Lys Thr His Thr Ser Pro Pro
1               5                   10

<210> SEQ ID NO 98
<211> LENGTH: 6
```

```
<212> TYPE: PRT
<213> ORGANISM: artificial sequence
<220> FEATURE:
<223> OTHER INFORMATION: N terminial glycine linker

<400> SEQUENCE: 98

Gly Cys Gly Gly Gly Gly
1               5

<210> SEQ ID NO 99
<211> LENGTH: 6
<212> TYPE: PRT
<213> ORGANISM: artificial sequence
<220> FEATURE:
<223> OTHER INFORMATION: N-terminal glycine serine linker

<400> SEQUENCE: 99

Cys Gly Gly Gly Gly Ser
1               5

<210> SEQ ID NO 100
<211> LENGTH: 9
<212> TYPE: PRT
<213> ORGANISM: artificial sequence
<220> FEATURE:
<223> OTHER INFORMATION: GCGSGGGGS linker

<400> SEQUENCE: 100

Gly Cys Gly Ser Gly Gly Gly Gly Ser
1               5

<210> SEQ ID NO 101
<211> LENGTH: 10
<212> TYPE: PRT
<213> ORGANISM: artificial sequence
<220> FEATURE:
<223> OTHER INFORMATION: C-terminal gamma 1 linker

<400> SEQUENCE: 101

Asp Lys Thr His Thr Ser Pro Pro Cys Gly
1               5                   10

<210> SEQ ID NO 102
<211> LENGTH: 18
<212> TYPE: PRT
<213> ORGANISM: artificial sequence
<220> FEATURE:
<223> OTHER INFORMATION: C terminal gamma linker 3

<400> SEQUENCE: 102

Pro Lys Pro Ser Thr Pro Pro Gly Ser Ser Gly Gly Ala Pro Gly Gly
1               5                   10                  15

Cys Gly

<210> SEQ ID NO 103
<211> LENGTH: 6
<212> TYPE: PRT
<213> ORGANISM: artificial sequence
<220> FEATURE:
<223> OTHER INFORMATION: C terminal glycine linker

<400> SEQUENCE: 103

Gly Gly Gly Gly Cys Gly
1               5

<210> SEQ ID NO 104
<211> LENGTH: 6
```

```
<212> TYPE: PRT
<213> ORGANISM: artificial sequence
<220> FEATURE:
<223> OTHER INFORMATION: C terminal glycine serine linker

<400> SEQUENCE: 104

Ser Gly Gly Gly Gly Cys
1               5

<210> SEQ ID NO 105
<211> LENGTH: 10
<212> TYPE: PRT
<213> ORGANISM: artificial sequence
<220> FEATURE:
<223> OTHER INFORMATION: GSGGGGSGCG linker

<400> SEQUENCE: 105

Gly Ser Gly Gly Gly Gly Ser Gly Cys Gly
1               5                   10

<210> SEQ ID NO 106
<211> LENGTH: 6
<212> TYPE: PRT
<213> ORGANISM: artificial sequence
<220> FEATURE:
<223> OTHER INFORMATION: glycine lysine linker

<400> SEQUENCE: 106

Gly Gly Lys Lys Gly Cys
1               5

<210> SEQ ID NO 107
<211> LENGTH: 6
<212> TYPE: PRT
<213> ORGANISM: artificial sequence
<220> FEATURE:
<223> OTHER INFORMATION: glycine lysine linker 2

<400> SEQUENCE: 107

Cys Gly Lys Lys Gly Gly
1               5

<210> SEQ ID NO 108
<211> LENGTH: 14
<212> TYPE: PRT
<213> ORGANISM: homo sapiens

<400> SEQUENCE: 108

Asp Arg Val Tyr Ile His Pro Phe His Leu Val Ile His Asn
1               5                   10

<210> SEQ ID NO 109
<211> LENGTH: 10
<212> TYPE: PRT
<213> ORGANISM: Homo sapiens

<400> SEQUENCE: 109

Asp Arg Val Tyr Ile His Pro Phe His Leu
1               5                   10

<210> SEQ ID NO 110
<211> LENGTH: 8
<212> TYPE: PRT
<213> ORGANISM: Homo sapiens

<400> SEQUENCE: 110

Asp Arg Val Tyr Ile His Pro Phe
```

```
<210> SEQ ID NO 111
<211> LENGTH: 11
<212> TYPE: PRT
<213> ORGANISM: artificial sequence
<220> FEATURE:
<223> OTHER INFORMATION: Synthetic peptide

<400> SEQUENCE: 111

Cys Gly Gly Asp Arg Val Tyr Ile His Pro Phe
1               5                   10

<210> SEQ ID NO 112
<211> LENGTH: 13
<212> TYPE: PRT
<213> ORGANISM: artificial sequence
<220> FEATURE:
<223> OTHER INFORMATION: Synthetic peptide

<400> SEQUENCE: 112

Cys Gly Gly Asp Arg Val Tyr Ile His Pro Phe His Leu
1               5                   10

<210> SEQ ID NO 113
<211> LENGTH: 13
<212> TYPE: PRT
<213> ORGANISM: artificial sequence
<220> FEATURE:
<223> OTHER INFORMATION: Synthetic peptide

<400> SEQUENCE: 113

Asp Arg Val Tyr Ile His Pro Phe His Leu Gly Gly Cys
1               5                   10

<210> SEQ ID NO 114
<211> LENGTH: 11
<212> TYPE: PRT
<213> ORGANISM: artificial sequence
<220> FEATURE:
<223> OTHER INFORMATION: Synthetic peptide

<400> SEQUENCE: 114

Cys Asp Arg Val Tyr Ile His Pro Phe His Leu
1               5                   10

<210> SEQ ID NO 115
<211> LENGTH: 6
<212> TYPE: PRT
<213> ORGANISM: artificial sequence
<220> FEATURE:
<223> OTHER INFORMATION: Synthetic peptide

<400> SEQUENCE: 115

Cys His Pro Phe His Leu
1               5

<210> SEQ ID NO 116
<211> LENGTH: 6
<212> TYPE: PRT
<213> ORGANISM: artificial sequence
<220> FEATURE:
<223> OTHER INFORMATION: Synthetic peptide

<400> SEQUENCE: 116

Cys Gly Pro Phe His Leu
1               5
```

```
<210> SEQ ID NO 117
<211> LENGTH: 6
<212> TYPE: PRT
<213> ORGANISM: artificial sequence
<220> FEATURE:
<223> OTHER INFORMATION: Synthetic peptide

<400> SEQUENCE: 117

Cys Tyr Ile His Pro Phe
1               5

<210> SEQ ID NO 118
<211> LENGTH: 6
<212> TYPE: PRT
<213> ORGANISM: artificial sequence
<220> FEATURE:
<223> OTHER INFORMATION: Synthetic peptide

<400> SEQUENCE: 118

Cys Gly Ile His Pro Phe
1               5

<210> SEQ ID NO 119
<211> LENGTH: 6
<212> TYPE: PRT
<213> ORGANISM: artificial sequence
<220> FEATURE:
<223> OTHER INFORMATION: Synthetic peptide

<400> SEQUENCE: 119

Cys Gly Gly His Pro Phe
1               5

<210> SEQ ID NO 120
<211> LENGTH: 8
<212> TYPE: PRT
<213> ORGANISM: artificial sequence
<220> FEATURE:
<223> OTHER INFORMATION: Synthetic peptide

<400> SEQUENCE: 120

Asp Arg Val Tyr Ile Gly Gly Cys
1               5

<210> SEQ ID NO 121
<211> LENGTH: 7
<212> TYPE: PRT
<213> ORGANISM: artificial sequence
<220> FEATURE:
<223> OTHER INFORMATION: Synthetic peptide

<400> SEQUENCE: 121

Asp Arg Val Tyr Gly Gly Cys
1               5

<210> SEQ ID NO 122
<211> LENGTH: 6
<212> TYPE: PRT
<213> ORGANISM: artificial sequence
<220> FEATURE:
<223> OTHER INFORMATION: Synthetic peptide

<400> SEQUENCE: 122

Asp Arg Val Gly Gly Cys
1               5

<210> SEQ ID NO 123
```

```
<211> LENGTH: 6
<212> TYPE: PRT
<213> ORGANISM: artificial sequence
<220> FEATURE:
<223> OTHER INFORMATION: human Ab1-6

<400> SEQUENCE: 123

Asp Ala Glu Phe Gly His
1               5

<210> SEQ ID NO 124
<211> LENGTH: 9
<212> TYPE: PRT
<213> ORGANISM: artificial sequence
<220> FEATURE:
<223> OTHER INFORMATION: LCMV-peptide gp33 (Q.beta.x33)

<400> SEQUENCE: 124

Lys Ala Val Tyr Asn Phe Ala Thr Met
1               5

<210> SEQ ID NO 125
<211> LENGTH: 16
<212> TYPE: PRT
<213> ORGANISM: artificial sequence
<220> FEATURE:
<223> OTHER INFORMATION: Synthetic peptide

<400> SEQUENCE: 125

Phe Gly Phe Pro Glu His Leu Leu Val Asp Phe Leu Gln Ser Leu Ser
1               5                   10                  15
```

VLP-ANTIGEN CONJUGATES AND THEIR USES AS VACCINES

CROSS REFERENCE TO RELATED APPLICATIONS

The present application is the U.S. National Phase of International Application PCT/EP2005/055009, filed Oct. 5, 2005, which designates the United States of America and which was published in English under PCT Article 21(2) as WO 2006/037787 A2 on Apr. 13, 2006, which claims the benefit of U.S. Provisional Application No. 60/615,637, filed Oct. 5, 2004; and European Patent Application No. 05105228.0, filed Jun. 14, 2005. The disclosures of all of the above-referenced applications are incorporated by reference herein in their entireties.

REFERENCE TO SEQUENCE LISTING SUBMITTED ELECTRONICALLY

The content of the electronically submitted sequence listing (Name: Substitute_Sequence_Listing_ascii.txt; Size: 69,604 bytes; and Date of Creation: Apr. 26, 2011) filed with the application is incorporated herein by reference in its entirety.

BACKGROUND OF THE INVENTION

1. Field of the Invention

The present invention is related to the fields of molecular biology, virology, immunology and medicine. The invention provides a composition comprising a virus-like particle (VLP) of an RNA-bacteriophage and at least one antigen, wherein the VLP is recombinantly produced in a host, and wherein the amount of host RNA with secondary structure comprised by the VLP is at most 20% of the amount of host RNA with secondary structure originally comprised by the VLP; and wherein the VLP and the at least one antigen are linked with one another.

The invention also provides methods for producing the compositions of the invention. The compositions of the invention are useful in the production of vaccines for the treatment of diseases, disorders and conditions. Furthermore, the compositions of the invention are particularly useful to efficiently induce strong antibody responses against the antigen within the indicated context while lowering or eliminating unwanted T cell responses.

2. Related Art

Virus-like particles (VLPs) of RNA-bacteriophages to which antigens are linked have been described to be useful vaccine compositions. Thus, WO 02/056905 describes VLP-antigen conjugates as vaccines for the treatment of infectious diseases, to prevent or cure cancer as well as to efficiently induce self-specific immune responses. Moreover, in the context of the induction of self-specific immune responses, specific VLP-antigen conjugates have been disclosed, for example, for the treatment of allergies (WO 03/040164) or bone diseases (WO 03/039225), or for the therapy and prophylaxis of conditions associated with the renin-activated angiotensin system (WO 03/031466).

Depending on the nature of the antigen and the related disease, certain types of immune response caused by the vaccine are usually more preferred over others. For example, while it is usually desirable to induce a strong cytotoxic T cell (CTL) response against tumor cells or viral infections, such a response, in particular for vaccines comprising self antigens, might result in serious adverse effect such as induction of self-specific T cells (Orgogozo, J. M. et al., Neurology 61, 46-54 (2003); Hock, C. et al., Natural Med. 8, 1270-75 (2002); Hock C. et al., Neuron 38, 547-554, (2003)).

Activation of antigen specific T cells largely depends on the cross-talk between T cells and the antigen presenting cells (APCs) such as dendritic cells, B cells and macrophages, which APCs present T cell antigens in the context of MHC molecules. One way leading to the activation of APCs is the interaction of CD40L on Th cells with CD40 on dendritic cells (Foy, T. M., et al., *Annu. Rev. Immunol.* 14:591 (1996)). Interestingly, this CD40L-mediated maturation of dendritic cells seems to be responsible for the helper effect on CTL responses. In fact, it has recently been shown that CD40-triggering by Th cells renders dendritic cells able to initiate a CTL-response (Ridge, J. P., et al., *Nature* 393:474 (1998); Bennett, S. R. M., et al., *Nature* 393:478 (1998); Schoenenberger, S. P., et al., *Nature* 393:480 (1998)).

Another way leading to the activation of APCs is through the activation of toll-like receptors expressed by APCs. So far ten human toll-like receptors have been identified, whose ligands exhibit a limited number of invariant patterns associated with pathogens (Medzhitov, R. and Janeway, C. A., Jr., *Cell* 91:295-298 (1997)). Examples of such patterns include lipopolysaccharides (LPS), non-methylated CG-rich DNA (CpG) or double stranded RNA, which are specific for bacterial and viral infections, respectively.

Generalized activation of APCs by factors that stimulate innate immunity may often be the cause for triggering self-specific lymphocytes and autoimmunity. Activation may result in enhanced expression of co-stimulatory molecules or cytokines such as IL-12 or IFNα. This view is compatible with the observation that administration of LPS together with thyroid extracts is able to overcome tolerance and trigger autoimmune thyroiditis (Weigle, W. O., *Adv. Immunol.* 30:159 (1980)). Moreover, in a transgenic mouse model, it was recently shown that administration of self-peptide alone failed to cause auto-immunity unless APCs were activated by a separate pathway (Garza, K. M., et al., *J. Exp. Med.* 191: 2021 (2000)). The link between innate immunity and autoimmune disease is further underscored by the observation that LPS, viral infections or generalized activation of APCs delay or prevent the establishment of peripheral tolerance (Vella, A. T., et al., *Immunity* 2:261 (1995); Ehl, S., et al., *J. Exp. Med.* 187:763 (1998); Maxwell, J. R., et al., *J. Immunol.* 162:2024 (1999)). In this way, innate immunity not only enhances the activation of self-specific lymphocytes but also inhibits their subsequent elimination.

The virus-like particles of RNA phages, such as Qβ or AP205 described in the prior art and used as antigen carrier for vaccination have been prepared by recombinant expression from *E. coli*. The resulting VLPs obtained by subsequent purification from *E. coli* lysate, however, still contain encapsulated *E. coli* components, mainly *E. coli* RNA as well as some *E. coli* proteins. Many bacterial components, in particular bacterial nucleic acids, and hereby in particular bacterial DNA and bacterial RNA, cause stimulation of T-cell responses through the activation of toll-like receptors. As indicated, the activation of T cell responses might result in serious adverse effects. Moreover, the presence of substances such as unidentified bacterial components beside the proven pharmaceutically active ingredients within vaccines is undesired due to potential risks or side effects caused by such unidentified bacterial components.

Thus, there remains a need in the art for the development of new and potent vaccines for treating broader spectrum of diseases. In particular there remains a need in the art for the development of new vaccines, for which, to the great extent possible, unwanted side effects such as activation or stimulation of undesired T-cell responses are lowered or eliminated while a maximal therapeutical effect is maintained.

SUMMARY OF THE INVENTION

We have surprisingly found that the inventive compositions are capable of inducing strong immune responses, in particular antibody responses, against the antigen comprised by the vaccine while minimizing or avoiding unwanted T cell responses or other unwanted side effects, such as fever.

Stimulation of innate immunity results in the induction of antibodies of the IgG2a and IgG2b type, which are more potent at tissue destruction than IgG1 (mouse). We have surprisingly found that the inventive compositions shift antibody isotype profile away from IgG2a and/or IgG2b or IgG1 (human).

In addition, we have surprisingly found that the inventive compositions are potent vaccines that induce strong immune responses against a large variety of antigens, in particular self antigens, which can be used as targets in treating a large variety of diseases, such as, but not limited to autoimmune diseases, inflammatory diseases, obesity and drug addiction.

Thus, in a first aspect, the invention provides for a composition comprising (a) a virus-like particle (VLP) comprising coat proteins, mutants or fragments thereof, of an RNA-bacteriophage with at least one first attachment site, wherein said VLP is recombinantly produced by a host, and wherein the amount of host RNA with secondary structures comprised by the VLP is at most 20%, preferably at most 10%, of the amount of host RNA with secondary structure originally comprised by said VLP; (b) at least one antigen with at least one second attachment site; wherein said at least one antigen (b) is linked to said VLP (a) through said at least one first attachment site and said at least one second attachment site. Preferably the inventive compositions form an ordered and repetitive antigen array. The at least one antigen can be selected from polypeptides, carbohydrates, steroid hormones, organic molecules or haptens, preferably, the at least one antigen is a self antigen or a hapten. Typical and preferred methods to determine the amount of RNA, preferably nucleic acids, in accordance with the present invention are provided herein.

The strongly decreased amount of host RNA, preferably host nucleic acids, in the inventive compositions and vaccines leads to VLPs or VLP-antigen conjugates that, as a consequence, possess a strongly decreased amount, or preferably are essentially free, of Toll-like receptor ligands. Toll-like receptors are considered to be the pivot linking the innate immune response and the adaptive immune response. Activation of Toll-like receptors leads to the general activation of the innate immune system as well as to the activation of APCs, which further leads to antigen-specific immune response. It was, therefore, surprising, that the inventive compositions and vaccines which comprise VLPs comprising at most 20%, preferably at most 10%, of the amount of host RNA with secondary structure originally comprised by the VLP, more preferably VLP being essentially free of host RNA, preferably host nucleic acids, and still more preferably being essentially free of Toll-like receptors, induce strong antigen-specific immune response, in particular antibody response, while typically bypassing the activation of Toll-like receptors. Moreover, the inventive compositions and vaccines induce a high immune response against the specific antigen in the composition, while minimizing or failing to prime CTL responses. In addition the inventive compositions and vaccines reduce the production of IgG2a and/or IgG2b and shift the antibody isotype away from the more tissue destructive IgG2a and/or IgG2b.

In a further aspect, the invention provides for a composition comprising (a) a virus-like particle (VLP) comprising coat proteins, mutants or fragments thereof, of an RNA-bacteriophage with at least one first attachment site, wherein said VLP is recombinantly produced by a host, and wherein said VLP is essentially free of host RNA, preferably wherein said VLP is essentially free of host nucleic acids; (b) at least one antigen with at least one second attachment site, wherein said at least one antigen (b) is linked to said VLP (a) through said at least one first attachment site and said at least one second attachment site.

We have further found that the inventive compositions and vaccines induce a high immune response against the specific antigen linked to VLP without noticeable, or typically and preferably significant, activation of inflammatory T cells, which is a subset of Th1 cells, as demonstrated by the decrease of IgG2a titers and, in particular, by the resulting low ratio of IgG2a/IgG1. Activation of different subset of T cells leads to the expression of different antibody subtypes. For example, Th1 cells notably produce IFN-γ, which promotes production of immunoglobulin IgG2a opsonising and complement-fixing antibodies and mediates macrophage activation and antibody-dependent cellular cytotoxicity. Th2 cells are characterised by IL-4 and IL-10 production and provide help for B-cell maturation and IgG1 antibody production. The IgG2a/IgG1 ratio is thus a good and well accepted parameter to measure the degree of activation of Th1 cells versus Th2 cells. In addition, reduction of IgG2a and/or IgG2b is a significant advantage if the opsonising and complement-fixing properties of the antibody subclasses are not wanted as in, for example, the case of vaccines developed for the induction of antibodies against self antigens.

In another preferred embodiment of the present invention, the composition further comprises at least one polyanionic macromolecule bound to the VLP. In an even more preferred embodiment of the present invention, the at least one polyanionic macromolecule is enclosed or packaged by the VLP. The presence of the at least one polyanionic macromolecule typically leads to an even higher antibody titer, in particular an IgG1 titer, against the antigens while maintaining low IgG2a/IgG1 ratios and low CTL responses. Moreover, the presence of the at least one polyanionic macromolecule bound to or, preferably, enclosed or packaged by the VLP, is typically advantageous and beneficial for the assembly of the coat proteins, mutants or fragments thereof, of a RNA-bacteriophage into VLPs as well as for their stabilization. In a preferred embodiment, the polyanionic macromolecule is a polyanionic polypeptide, more preferably the polyanionic macromolecule is polyglutamic acid and/or polyaspartic acid.

In further aspects, the invention provides methods of preparing the inventive compositions and VLP of an RNA-bacteriophage-antigen conjugates, respectively. In a preferred aspect, the invention provides a method of preparing the inventive composition and a VLP of an RNA-bacteriophage-antigen conjugate, respectively, which method comprises the steps of (a) recombinantly producing by a host a virus-like particle (VLP) with at least one first attachment site, wherein said VLP comprises coat proteins, mutants or fragments thereof, of an RNA-bacteriophage; (b) disassembling said virus-like particle to said coat proteins, mutants or fragments thereof, of said RNA-bacteriophage; (c) purifying said coat proteins, mutants or fragments thereof; (d) reassembling said purified coat proteins, mutants or fragments thereof, of said RNA-bacteriophage to a virus-like particle, wherein said virus-like particle is essentially free of host RNA, preferably host nucleic acids; and (e) linking at least one antigen with at least one second attachment site to said VLP obtained from step (d). In a preferred embodiment, the step of reassembling of said purified coat proteins is effected in the presence of at least one polyanionic macromolecule.

In another aspect, the invention provides a vaccine composition comprising the composition of the invention, preferably further comprising a buffer. The vaccine may be administered to patients either without or with at least one adjuvant. In a further aspect, the invention provides a method of immunization comprising administering said vaccine to an animal or human.

In a further aspect, the invention provides a method of treating a disease comprising administering the composition of the invention to an animal or human. In a preferred embodiment, the invention provides a method of treating diseases, for example but not limited to, inflammatory diseases, chronic autoimmune diseases, obesity or drug addiction.

In still another aspect, the invention provides a pharmaceutical composition comprising the composition of the invention and an acceptable pharmaceutical carrier.

In a still further aspect, the inventive vaccine compositions are essentially free of bacterial RNA as well as other bacterial components, leading to more defined compositions and vaccines, respectively. This will not only lead to safer vaccines but is also in line with the good manufacturing practice (GMP) standard.

DETAILED DESCRIPTION OF THE INVENTION

Definitions

Figure 1:
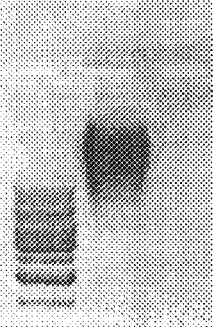
FIG. 1 depicts the analysis of RNA hydrolysis from Qβ VLPs by RNase A on a 1% agarose gel stained with ethidium bromide. Loaded on the gel are the following samples: 1. MBI Fermentas 1 kb DNA ladder; 2. Prior art Qβ VLP; 3. Qβ VLP treated with RNase A in 0.2×HBS buffer pH 7.2.

Antibody isotype: Unless otherwise indicated, the nomenclature of the antibody isotype used in the application is mouse nomenclature. Skilled person in the art is aware of the corresponding human nomenclature. For example, antibody isotype IgG2a of mouse is antibody isotype IgG1 of human.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Attachment Site, First: As used herein, the phrase "first attachment site" refers to an element which is naturally occurring with the VLP or which is artificially added to the VLP, and to which the second attachment site may be linked. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid such as lysine. The first attachment site is located, typically on the surface, and preferably on the outer surface of the VLP. Multiple first attachment sites are present on the surface, preferably on the outer surface, of the virus-like particle, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in another preferred embodiment the first attachment site is artificially added to the VLP.

Attachment Site, Second: As used herein, the phrase "second attachment site" refers to an element which is naturally occurring with or which is artificially added to the antigen of the present invention and to which the first attachment site may be linked. The second attachment site of the invention may be a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is the sulfhydryl group, preferably of an amino acid such as cysteine. The terms "at least one antigen with at least one second attachment site", refer, therefore, to a construct comprising the antigen of the invention and at least one second attachment site. However, in particular for a second attachment site, which is not naturally occurring within the antigen, such a construct typically and preferably further comprises a "linker". In another preferred embodiment the second attachment site is associated with the antigen of the invention through at least one covalent bond, preferably through at least one peptide bond. In a further embodiment, the second attachment site is naturally occurring within the antigen of the invention. In yet another preferred embodiment, the second attachment site is artificially added to the antigen of the invention through a linker, preferably comprising a cysteine, by protein fusion.

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "bound" is broader than and includes terms such as "coupled," "fused," "enclosed", "packaged" and "attached." For example, the polyanionic macromolecule such as the polyglutamic acid can be, and typically and preferably is, enclosed or packaged by the VLP, typically and preferably without the existence of an actual covalent binding.

Coat protein: The term "coat protein" and the interchangeably used term "capsid protein" within this application, refers to a viral protein, which is capable of being incorporated into a virus capsid or a VLP. Typically and preferably the term "coat protein" refers to the coat protein encoded by the genome of an RNA bacteriophage or by the genome of a variant of an RNA bacteriophage. More preferably and by way of example, the term "coat protein of AP205" refers to SEQ ID NO:29 or the amino acid sequence, wherein the first methionine is cleaved from SEQ ID NO:29. More preferably and by way of example, the term "coat protein of Qβ" refers to SEQ ID NO:10 ("Qβ") and SEQ ID NO:11 (A1), with or without the methione at the N-terminus. (SEQ ID NO:67). The capsid of bacteriophage Qβ is composed mainly of the Qβ CP, with a minor content of the A1 protein.

Epitope: As used herein, the term "epitope" refers to continuous or discontinuous portions of a polypeptide having antigenic or immunogenic activity in an animal, preferably a mammal, and most preferably in a human. An epitope is recognized by an antibody or a T cell through its T cell receptor in the context of an MHC molecule.

Essentially free of host RNA, preferably host nucleic acids: The term "essentially free of host RNA, preferably host nucleic acids" as used herein, refers to the amount of host RNA, preferably host nucleic acids, comprised by the VLP, which is typically and preferably less than 30 μg, preferably less than 20 μg, more preferably less than 10 μg, even more preferably less than 8 μg, even more preferably less than 6 μg, even more preferably less than 4 μg, most preferably less than 2 μg, per mg of the VLP. Host, as used within the aforementioned context, refers to the host in which the VLP is recombinantly produced, which host is preferably a bacteria, and further preferably $E.\ coli$. Conventional methods of determining the amount of RNA, preferably nucleic acids, are known to the skilled person in the art. The typical and preferred method to determine the amount of RNA, preferably nucleic acids, in accordance with the present invention is described in Example 17 for prior art Qβ VLP and Qβ VLPs of the invention. Identical, similar or analogous conditions are, typically and preferably, used for the determination of the amount of RNA, preferably nucleic acids, for inventive compositions comprising VLPs other than Qβ. The modifications of the conditions eventually needed are within the knowledge of the skilled person in the art. The numeric value of the amounts determined should typically and preferably be understood as comprising values having a deviation of ±10%, preferably having a deviation of ±5%, of the indicated numeric value.

Immunostimulatory nucleic acid: As used herein, the term immunostimulatory nucleic acid refers to a nucleic acid capable of inducing and/or enhancing an immune response.

Immunostimulatory substance: As used herein, the term "immunostimulatory substance" refers to a substance capable of inducing and/or enhancing an immune response, and hereby typically and preferably an immune response specifically against the antigen comprised in the inventive composition.

Linked: The term "linked" (or its noun: linkage) as used herein, refers to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only encompass a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker.

Linker: A "linker", as used herein, either associates the second attachment site with antigen of the invention or already comprises, essentially consists of, or consists of the second attachment site. Preferably, a "linker", as used herein, already comprises the second attachment site, typically and preferably—but not necessarily—as one amino acid residue, preferably as a cysteine residue. A "linker" as used herein is also termed "amino acid linker", in particular when a linker according to the invention contains at least one amino acid residue. Thus, the terms "linker" and "amino acid linker" are interchangeably used herein. However, this does not imply that such a linker consists exclusively of amino acid residues, even if a linker consisting of amino acid residues is a preferred embodiment of the present invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Further linkers useful for the present invention are molecules comprising a C1-C6 alkyl-, a cycloalkyl such as a cyclopentyl or cyclohexyl, a cycloalkenyl, aryl or heteroaryl moiety. Moreover, linkers comprising preferably a C1-C6 alkyl-, cycloalkyl-(C5, C6), aryl- or heteroaryl-moiety and additional amino acid(s) can also be used as linkers for the present invention and shall be encompassed within the scope of the invention. Association of the linker with the antigen of the invention is preferably by way of at least one covalent bond, more preferably by way of at least one peptide bond. In case of a second attachment site not naturally occurring with the antigen of the invention, the linker is associated to the at least one second attachment site, for example, a cysteine, preferably, by way of at least one covalent bond, more preferably by way of at least one peptide bond.

Ordered and repetitive antigen array: As used herein, the term "ordered and repetitive antigen array" generally refers to a repeating pattern of antigen characterized by a typically and preferably high order of uniformity in spatial arrangement of the antigens with respect to the virus-like particle. In one embodiment of the invention, the repeating pattern may be a geometric pattern. VLP of RNA phages possess strictly repetitive paracrystalline orders of antigens or antigenic determinants, preferably with spacing of 1 to 30 nanometers, preferably 2 to 15 nanometers, even more preferably 2 to 10 nanometers, even again more preferably 2 to 8 nanometers, and further more preferably 1.6 to 7 nanometers.

Packaged: The term "packaged" as used herein refers to the state of a polyanionic macromolecule in relation to the VLP. The term "packaged" as used herein includes binding that may be covalent, e.g., by chemically coupling, or non-covalent, e.g., ionic interactions, hydrophobic interactions, hydrogen bonds, etc. In a preferred embodiment, the term "packaged" refers to the enclosement, or partial enclosement, of a polyanionic macromolecule by the VLP. Thus, the polyanionic macromolecule can be enclosed by the VLP without the existence of an actual binding, in particular of a covalent binding. In preferred embodiments, the at least one polyanionic macromolecule is packaged inside the VLP, most preferably in a non-covalent manner.

Polyanionic macromolecule: The term "polyanionic macromolecule", as used herein, refers to a molecule of high relative molecular mass which comprises repetitive groups of negative charge, the structure of which essentially comprises the multiple repetition of units derived, actually or conceptually, from molecules of low relative molecular mass. A polyanionic macromolecule should have a molecular weight of at least 2000 Dalton, more preferably of at least 3000 Dalton and even more preferably of at least 5000 Dalton. The term "polyanionic macromolecule" as used herein, typically and preferably refers to a molecule that is not capable of activating toll-like receptors. Thus, the term "polyanionic macromolecule" typically and preferably excludes Toll-like receptors ligands, and even more preferably furthermore excludes immunostimulatory substances such as Toll-like receptors ligands, immunostimulatory nucleic acids, and lipopolysaccharides (LPS). More preferably the term "polyanionic macromolecule" as used herein, refers to a molecule that is not capable of inducing cytokine production. Even more preferably the term "polyanionic macromolecule" excludes immunostimulatory substances.

Polyaspartic acid: The term "polyaspartic acid" as used herein, should refer to a polypeptide comprising at least 50%, preferably at least 70%, more preferably at least 90%, more preferably at least 95%, more preferably at least 99%, more preferably 100%, aspartic acid molecules out of the total number of amino acids consisted of by said polypeptide. The aspartic acid molecules are hereby either all-L or all-D or mixtures thereof.

Polyglutamic acid: The term "polyglutamic acid", as used herein, refers to a polypeptide comprising at least 50%, preferably at least 70%, more preferably at least 90%, more preferably at least 95%, more preferably at least 99%, more preferably 100% glutamic acid molecules out of the total number of amino acids consisted of by said polypeptide. The glutamic acid molecules are hereby either all-L or all-D or mixtures thereof.

Poly (GluAsp): The term "Poly (GluAsp)" as used herein, refers to a polypeptide comprising at least 50%, preferably at least 70%, more preferably at least 90% or again more preferably 95%, still more preferably 99% glutamic acid and aspartic acid in total, out of the total number of amino acids consisted of by said polypeptide. The glutamic acid molecules and the aspartic acid molecules are hereby either all-L or all-D or mixtures thereof.

Polypeptide: The term "polypeptide" as used herein refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. Post-translational modifications of the polypeptide, for example, glycosylations, acetylations, phosphorylations, and the like are also encompassed.

The term "recombinant VLP", as used herein, refers to a VLP that is obtained by a process which comprises at least one step of recombinant DNA technology. The term "VLP recombinantly produced", as used herein, refers to a VLP that is obtained by a process which comprises at least one step of recombinant DNA technology. Thus, the terms "recombinant VLP" and "VLP recombinantly produced" are interchangeably used herein and should have the identical meaning.

RNA, preferably nucleic acid, with secondary structure: The term "RNA, preferably nucleic acid, with secondary structure", as used herein, refers to RNA, preferably nucleic acid, that can intercalate ethidium bromide, which can be visualized by the fluorescence of the ethidium bromide under UV light. The typical and preferred method to intercalate ethidium bromide into host RNA, preferably host nucleic acids, with secondary structure in accordance with the present invention is described in EXAMPLE 2 and 3 of the present invention by way of Qβ VLPs. Identical, similar or analogous conditions are, typically and preferably, used for intercalation of ethidium bromide into host RNA, preferably host nucleic acids, with secondary structure comprised by the VLPs other than Qβ. The modifications of the conditions eventually needed are within the knowledge of the skilled person in the art.

Host RNA, preferably host nucleic acids: The term "host RNA, preferably host nucleic acids", as used herein, refers to the RNA, or preferably nucleic acids, that are originally synthesized by the host. The RNA, preferably nucleic acids, may, however, undergo chemical and/or physical changes during the procedure of reducing or eliminating the amount of RNA, preferably nucleic acids, typically and preferably by way of the inventive methods, for example, the size of the RNA, preferably nucleic acids, may be shortened or the secondary structure thereof may be altered. However, even such resulting RNA or nucleic acids is still considered as host RNA, or host nucleic acids.

Amount of host RNA, preferably nucleic acid, with secondary structure: The term "amount of host RNA, preferably nucleic acid, with secondary structure", as used herein, refers to the amount of host RNA, preferably nucleic acid, that can intercalate ethidium bromide, which can be visualized by the fluorescence of the ethidium bromide under UV light. The typical and preferred method to determine the amount of host RNA, preferably nucleic acid, that can intercalate ethidium bromide in accordance with the present invention and, thus, of host RNA, preferably nucleic acid, with secondary structure comprised by the VLPs is to measure the amount of ethidium bromide intercalated into the RNA, preferably nucleic acids, as described in EXAMPLE 2 and 3 of the present invention by way of Qβ VLPs. Identical, similar or analogous conditions are, typically and preferably, used for the determination of the amount of host RNA, preferably host nucleic acids, with secondary structures comprised by the VLPs other than Qβ. The modifications of the conditions eventually needed are within the knowledge of the skilled person in the art.

Amount of host RNA, preferably nucleic acid, with secondary structure originally comprised by the VLP: The term "amount of host RNA, preferably nucleic acid, with secondary structure originally comprised by the VLP", as used herein, refers to the amount of host RNA, preferably nucleic acid, with secondary structure that was comprised by the VLP after recombinant production by the host but prior to the reduction or elimination of the amount of host RNA, preferably nucleic acids, with secondary structure of the, typically and preferably the same, VLP, that is effected typically and preferably by way of the inventive methods. The "same VLP" as used within this context typically and preferably refers to a VLP deriving from the same batch of expression. Typically and preferably, the term "amount of host RNA, preferably nucleic acid, with secondary structure originally comprised by the VLP", as used herein, refers to the amount of host RNA, preferably nucleic acid, with secondary structure that was comprised by the VLP after recombinant production by the host and after subsequent purification of the resulting VLP but prior to the reduction or elimination of the amount of host RNA, preferably nucleic acids, with secondary structure of the, typically and preferably the same, VLP that is effected typically and preferably by way of the inventive methods. As indicated, the "same VLP" as used within this context typically and preferably refers to a VLP deriving from the same batch of expression, preferably the same batch of purification. Recombinantly produced VLP is typically and preferably to be purified from host cell lysate. Methods of purification of VLP from host cell lysate have been disclosed in the prior art, for example, in WO 02/056905, WO 04/007538 or, preferably, in EXAMPLE 1 of the present application for Qβ VLP. Typically and preferably the reduction of host RNA, preferably nucleic acid, with secondary structure in accordance with the present invention is determined by saving an adequate portion of the recombinantly expressed VLP, preferably after purification, for later to, preferably contemporaneously, determine then, first, the amount of host RNA, preferably nucleic acids, with secondary structure originally comprised by such VLP, and second, the amount of host RNA, preferably nucleic acids, with secondary structure comprised by the inventive VLP, i.e. the VLP typically and preferably obtained after applying the inventive methods. As indicated, the typical and preferred method to determine the amount of host RNA, preferably nucleic acid, with secondary structure is described in EXAMPLE 2 and 3 of the present invention by way of Qβ VLPs. Identical, similar or analogous conditions are, typically and preferably, used for the determination of the amount of host RNA, preferably host nucleic acids, with secondary structures comprised by the VLPs other than Qβ. The modifications of the conditions eventually needed are within the knowledge of the skilled person in the art.

Self antigen: The term "self antigen", as used herein, refers to (i) a polypeptide or a protein encoded by the host's DNA or to a product derived from polypeptides or RNA encoded by the host DNA; (ii) a polypeptide or a protein that has a high homology to (i), wherein said homology is at least 90%, more preferably at least 92%, and again more preferably at least 95%, and again even more preferably at least 97% and that typically and preferably induces in vivo the production of antibody specifically binding to the polypeptide or protein of (i); as well as (iii) an ortholog of the self antigen as defined in (i). Typically and preferably said ortholog induces in vivo the production of antibody specifically binding to the polypeptide or protein of (i). The term "ortholog" denotes a polypeptide or a protein obtained from one species that is the functional counterpart of a polypeptide from a different species. Sequence differences among orthologs are the result of speciation. The term "self antigen" as used herein should furthermore encompass chemical modifications including but not limited to glycosylations, acetylations, phosphorylations of the self antigen as defined above. Furthermore, the term "self antigen", as used herein, preferably refers to polypeptides that result from a combination of two or several self antigen.

Fragment of a self antigen: The term "fragment of a self antigen", as used herein, refers to a polypeptide that comprises, or alternatively consists of, a fraction of a self antigen and that preferably, has a length of at least four, preferably at least five, more preferably at least six, at least seven, at least eight, or even more preferably at least twelve or at least fifteen amino acids and that typically and preferably induces in vivo the production of antibody specifically binding to the polypeptide or protein of (i) of the self antigen definition. The term "fragment of a self antigen" as used herein should furthermore encompass chemical modifications including but not limited to glycosylations, acetylations, phosphorylations of the "fragment of a self antigen" as defined above.

Variant of a self antigen: The term "variant of a self antigen", as used herein, refers to a polypeptide that has a homology to the polypeptide or protein of (i) in the definition of self antigen, wherein said homology is at least 75%, more preferably at least 80%, and again more preferably at least 87% and that typically and preferably induces in vivo the production of antibody specifically binding the polypeptide or protein of (i) of the self antigen definition. The term "variant of a self antigen" as used herein should furthermore encompass chemical modifications including but not limited to glycosylations, acetylations, phosphorylations of the "variant of a self antigen" as defined above.

Toll-like receptor (TLR) ligand: Toll-like receptors (TLRs) are expressed by myelomonocytic cells and endothelial and epithelial cells as well as cells from various organ systems. Toll-like receptors are transmembrane proteins, all of which have a common extracellular leucine-rich domain and a conserved cytoplasmic domain. The cytoplasmic domain of TLR is homologous to the IL-1 and IL-18 receptors and contains the Toll/IL-1 receptor (TIR) homology domain common to these receptors. Toll-like receptors share a common activation pathway mediated through their TIR signalling domains, resulting in the nuclear translocation and activation of the pro-inflammatory transcription factor NF-kB (Abreu M. T. and Arditi M. J. Pediatrics (2004), 421-9). To date, 10 different TLR molecules have been cloned from the human genome (Zarember K A et al., J. Immunol. (2002), 168:554-61) and 11 TLRs have been cloned in mouse (Zhang et al., science, (2004), 303:1522-6).

As used herein, the term "Toll-like receptor ligand" or "TLR ligand" refers to any ligand which is capable of activating at least one of the TLRs (see e.g. Beutler, B. 2002, Curr. Opin. Hematol., 9, 2-10, Schwarz et al., 2003, Eur. J. Immunol., 33, 1465-1470). A TLR ligand of the invention activates without limitation at least one Toll-like receptor 1 (TLR1), TLR2, TLR3, TLR4, TLR5, TLR6, TLR7, TLR8, TLR9, TLR10, or TLR11. For example, peptidoglycan (PGN) or lipoteichoic acid (LTA) typically and preferably activates TLR2 (Aliprantis et al., Science (1999), 285:736-9; Underhill, et al., Nature, (1999), 401:811-5); double-stranded RNA, e.g. poly (I:C), typically and preferably activates TLR3 (Alexopoulou et al., Nature (2001), 413:732-8); lipopolysaccharide (LPS) typically and preferably activates TLR4 (Poltorak, et al., Science (1998), 282:2085-8); flagellin typically and preferably activates TLR5 (Hayashi et al. Nature (2001), 410:1099-103); single stranded RNA, for example bacterial RNA, and certain synthetic substances such as imidazoquinolines, typically and preferably activate TLR7 and TLR8 (Diebold S. et al. Science 303:1529; Heil, F H. et al. Science 303:1526); bacterial DNA, in particular DNA containing CpG motifs typically and preferably activates TLR9 (Schnare et al. Curr. Biol. (2000), 10:1139-42; Hemmi H et al. Nature (2000), 408: 740-5). These cited papers are incorporated herein by reference. A summary of TLR ligands is given in the table of Abreu's review paper and incorporated herein by reference (Abreu M. T. and Arditi M. J., Pediatrics (2004), 421-9) and a reference for TLR 11 and its ligand is described in Zhang et al., Science, (2004), 303:1522-6. By referring to these incorporated papers in conjunction with general knowledge of a skilled person in the art, it is within a routine practice to test whether a molecule is a TLR ligand in accordance with the present invention, and whether a TLR ligand activates at least one of the TLR.

One general, typical and preferred method to measure the activation of a Toll-like receptor in accordance with the present invention is to transfect a cell line, which does not express Toll-like receptor, with a construct that is capable of expressing at least one Toll-like receptor. A NF-kB activated reporter gene, such as luciferase, can be either transfected into said cell line or be comprised by the genome of said cell line. After adding the to-be-tested molecule to the cell culture, the activity of the reporter gene can be quantified and compared with cells to which the to-be-tested molecule has not been added. It is to be mentioned that for the TLR1 and TLR6 activity test, coexpression of TLR2 is prerequisite. It is obvious to a skilled artisan that some TLR-ligands that are unstable, such as RNA with secondary structure, need to be stabilized for testing. One way for stabilization is to pack the RNA with secondary structure into liposomes or substances used for transfection, (eg. DOTAP).

The reference for the TLR sequences can be found in the database Swissprot under the accession numbers TLR1_human; TLR2_human; TLR3_human; TLR4_human; TLR5_human; TLR6_human; TLR7_human; TLR8_human; TLR9_human. Human TLR10 can be found under GenBank accession number AAQ88667 or AAK26744. The accession numbers of the mouse sequences are accordingly TLR1_mouse; TLR2_mouse; TLR3_mouse; TLR4_mouse; TLR5_mouse; TLR6_mouse; TLR7_mouse; TLR8_mouse; TLR9_mouse; TLR10_mouse in Swissprot database. Mouse TLR11 is under GenBank accession number AY531552. The skilled person in the art can set up corresponding assays for the TLR receptors from other mammalian species.

The typical and preferred example for such testing in accordance with the present invention is as follows: $3 \times 10^6$ HEK293 cells are electroporated at 200 volt and 960 µF with 1 µg of TLR expression plasmid and 20 ng NF-kB luciferase reporter-plasmid. The overall amount of plasmid DNA is held constant at 15 µg per electroporation by addition of the appropriate empty expression vector. Cells are seeded at $10^5$ cells per well and after overnight culture stimulated with the ligand to be tested for a further 7 to 10 hours. Typical examples of concentration ranges for known TLR ligands are 25 µg/ml RNA40-42 complexed to DOTAP (facilitating the internalization of RNA inside the cell), 1 µM CpG-ODN 2006, 10 µMR-848, 50 µg/ml poly(I:C) or 1 µg/ml Pam3Cys (Heil, F H. et al. Science 303:1526). Stimulated cells are lysed using reporter lysis buffer (Promega, Mannheim, Germany) and lysate is assayed for luciferase activity using a luminometer, typically and preferably the Berthold luminometer (Wildbad, Germany), according to the manufacturer's instruction. It is within the knowledge of the skilled person in the art to accordingly adapt the aforementioned experiment for the testing of any ligand.

A ligand is, then, considered to activate a TLR in accordance with this invention, when the induced luciferase activity is statistically significantly higher than a threshold value determined from the activity of the negative control (identical experiment and identical experimental conditions without the addition of the ligand to be tested). A threshold value within this context is defined by the mean of the luciferase activities of the negative control in six independent experiments plus three times the standard deviation of the luciferase activities from the six experiments. A ligand is, then typically and preferably, considered to "statistically significantly" activate a TLR when the luciferase activity of the ligand is higher than the threshold value determined as indicated above. Preferably, a ligand is considered to "statistically significantly" activate a TLR when the luciferase activity of the ligand is at least two times higher, preferably three times higher, even more preferably five times higher than the threshold value determined as indicated above.

Virus-like particle of a RNA phage: As used herein, the term "virus-like particle of a RNA phage" refers to a virus-like particle comprising, or preferably consisting essentially of or consisting of coat proteins, mutants or fragments thereof, of a RNA phage. In addition, virus-like particle of a RNA phage resembling the structure of a RNA phage, being non replicative or non-infectious, and typically and preferably being non replicative and non-infectious. Typically and preferably, the term "virus-like particle of a RNA phage" should furthermore refer to a virus-like particle of a RNA phage which lacks at least one of the genes, preferably all of the genes, encoding for the replication machinery of the RNA phage, and typically and further preferably even at least one of the genes, preferably all of the genes, encoding the protein or proteins responsible for viral attachment to or entry into the host. This definition should, however, also encompass virus-like particles of RNA phages, in which the aforementioned gene or genes are still present but inactive, and, therefore, also leading to non-replicative and/or noninfectious virus-like particles of a RNA phage. Moreover, the term "virus-like particle of a RNA phage" should therefore also encompass in its broadest definition a virus particle of a RNA phage, the genome of which has been inactivated by physical or chemical or genetic methods so that the virus particle is not capable of infecting and/or replicating. Preferred VLPs derived from RNA-phages exhibit icosahedral symmetry and consist of 180 subunits. Within this present disclosure the term "subunit" and "monomer" are interexchangeably and equivalently used within this context. In this application, the term "RNA-phage" and the term "RNA-bacteriophage" are interchangeably used.

The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

One, a, or an: when the terms "one", "a", or "an" are used in this disclosure, they mean "at least one" or "one or more" unless otherwise indicated.

This invention provides a composition comprising (a) a virus-like particle (VLP) comprising coat proteins, mutants or fragments thereof, of a RNA-bacteriophage with at least one first attachment site, wherein said VLP is recombinantly produced by a host, and wherein the amount of host RNA, preferably host nucleic acids, with secondary structure comprised by the VLP is at most 20%, preferably 10%, even more preferably 5%, still more preferably 3%, still more preferably 1% of the amount of host RNA, preferably host nucleic acids, with secondary structure originally comprised by the VLP; (b) at least one antigen with at least one second attachment site; wherein said at least one antigen (b) is linked to said VLP (a) through said at least one first attachment site and said at least one second attachment site. In a preferred embodiment, the VLP of the invention is essentially free of host RNA, preferably host nucleic acid.

In one aspect, the invention provides a composition comprising: (a) a virus-like particle (VLP) comprising coat proteins, mutants or fragments thereof, of an RNA-bacteriophage with at least one first attachment site, wherein said VLP is recombinantly produced by a host, and said VLP is essentially free of host RNA, preferably host nucleic acids; (b) at least one antigen with at least one second attachment site; and wherein said at least one antigen (b) is linked to said VLP (a) through said at least one first attachment site and said at least one second attachment site.

In one aspect, this invention provides a composition comprising (a) a virus-like particle (VLP) comprising coat proteins, mutants or fragments thereof, of a RNA-bacteriophage with at least one first attachment site, wherein said VLP is recombinantly produced by a host, and wherein said VLP comprises not more than 60 μg, preferably not more than 50 μg, even more preferably not more than 40 μg, still more preferably not more than 27 μg, still more preferably not more than 20 μg, more preferably not more than 9 μg, most preferably not more than 5 μg host RNA, preferably host nucleic acids, with secondary structure; (b) at least one antigen with at least one second attachment site; wherein said at least one antigen (b) is linked to said VLP (a) through said at least one first attachment site and said at least one second attachment site. In one preferred embodiment, the VLP of the invention is essentially free of host RNA, preferably host nucleic acids.

The virus-like particle of the invention is a recombinant VLP. Typically and preferably, a recombinant VLP is produced by cloning the gene encoding a viral coat protein or a mutant or a fragment thereof, which retains the ability of forming a VLP, into an expression vector and expressing the resulting construct in a compatible host, such as bacteria, typically and preferably in E. coli, yeast, insect or mammalian expression systems.

Preferred examples have been disclosed in WO02/056905 and are herein incorporated by way of reference. A detailed description of the preparation of VLP particles from Qβ are, in particular, disclosed in example 18 of WO 02/056905. It is to note that the VLP-antigen conjugates described in the prior art such as in WO02/056905 still contain the amount of host RNA within the VLP as obtained and resulted through expression in the manner described above. The VLP or the inventive VLP-antigen conjugates, on the other hand, have been prepared or further treated by the inventive methods to exclude, reduce or eliminate the host RNA, preferably host nucleic acids.

In a preferred embodiment, the virus-like particle comprises, or alternatively consists essentially of, or consists of, coat proteins, and/or mutants, and/or fragments thereof, of a RNA-bacteriophage. In a further preferred embodiment, the composition comprises a virus-like particle of a RNA-bacteriophage with at least one first attachment site. In one further preferred embodiment the RNA-bacteriophage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; j) bacteriophage f2; k) bacteriophage PP7 and l) bacteriophage AP205. In a further preferred embodiment, the coat protein of the RNA phage has an amino acid sequence selected from a group comprising or, alternatively consisting of SEQ ID NO:10; a mixture of SEQ ID NO:10 and SEQ ID NO:11; SEQ ID NO:12; SEQ ID NO:13; SEQ ID NO:14; SEQ ID NO:15; a mixture of SEQ ID NO:15 and SEQ ID NO:16; SEQ ID NO:17; SEQ ID NO:18; SEQ ID NO:19; SEQ ID NO:20; SEQ ID NO:21; SEQ ID NO:22; and SEQ ID NO:29.

The term "a fragment of a coat protein", as used herein, is defined as a polypeptide, which is preferably capable of assembling into a virus-like structure of a RNA phage and which is of at least 70%, preferably at least 80%, more preferably at least 90%, the length of the wild-type coat protein. Preferably the fragment is obtained by at least one internal deletion or at least one truncation at the N and/or C terminus or at least one combination thereof. A fragment of the coat protein further encompasses polypeptide, which is preferably capable of assembling into a virus-like particle of a RNA phage and which has at least 80%, preferably 90%, even more preferably 95% amino acid sequence identity with the fragment of a coat protein as defined above.

The term "mutant coat protein" or the term "mutant of a coat protein" as interchangeably used in this invention, refers to a polypeptide having an amino acid sequence derived from the wild type coat protein, which is at least 80%, preferably at least 85%, 90%, 95%, 97%, or 99% identical to the wild type sequence and retains preferably the ability to assemble into a VLP. Typical and preferred examples of mutations include truncations, internal deletions, additions or substitutions of one or more amino acids with respect to the wild-type coat proteins, and hereby preferably at most ten, further preferably at most six, even further preferably at most four, three, two and one amino acid mutation with respect to the wild-type coat protein. "Mutant coat protein" should also, preferably, encompass fragments of wild type coat protein that are capable of assembling into a VLP. Furthermore, the term "mutant coat protein", as used herein, should also, preferably, encompass polypeptide having an amino acid sequence which is at least 80%, preferably at least 85%, 90%, 95%, 97%, or 99% identical to the corresponding wild type coat protein or fragment thereof that are preferably capable of assembling into a VLP.

Assembly of the coat protein, mutant or fragment thereof, into a VLP may be tested, as one skilled in the art would appreciate by expressing the coat protein, mutant or fragment thereof in E. coli, optionally purifying the capsids by gel filtration from cell lysate, and analysing the capsid formation in an immunodiffusion assay (Ouchterlony test) or by Electron Microscopy (EM) (Kozlovska, T. M. et al., Gene 137: 133-37 (1993)). Immunodiffusion assays and EM may be directly performed on cell lysate.

In a further preferred embodiment of the invention, the VLP is a mosaic VLP comprising or alternatively consisting of more than one sequence, preferably two sequences of coat proteins, and/or mutants, and/or a fragments thereof, of a RNA phage. Preferably, the mosaic VLP comprises or alternatively consists of two different coat proteins of a RNA phage, said two coat proteins have an amino acid sequence of SEQ ID NO:10 and SEQ ID NO:11, or of SEQ ID NO:15 and SEQ ID NO:16. In a further preferred embodiment, the mosaic VLP comprises or alternatively consists of two different coat proteins of a RNA phage, said two coat proteins have an amino acid sequence of SEQ ID NO:10 and a C-terminal truncation of SEQ ID NO:1, or of SEQ ID NO:15 and a C-terminal truncation of SEQ ID NO:16. The term "C-terminal truncation of SEQ ID NO:11", as used herein, refers to a sequence which is the result of a truncation of 1, 2, 3, . . . 50, . . . 100, . . . 150, . . . 195 or 196 amino acids from the C-terminal of SEQ ID NO:11.

In further preferred embodiments of the invention, the virus-like particle and the composition of the invention comprises, or alternatively consists essentially of, or alternatively consists of coat proteins, and/or fragments and/or mutants thereof, of a RNA bacteriophage selected from the group consisting of: a) bacteriophage AP205; b) bacteriophage fr; c) bacteriophage R17; d) bacteriophage f2; e) bacteriophage SP; f) bacteriophage MS2; g) bacteriophage M11; h) bacteriophage MX1; i) bacteriophage NL95; and j) bacteriophage PP7.

In further preferred embodiments of the invention, the virus-like particle and the composition of the invention comprises, or alternatively consists essentially of, or alternatively consists of coat proteins, and/or fragments thereof, of the RNA-bacteriophage Qβ or of the RNA-bacteriophage fr, or of the RNA-bacteriophage AP205 or of RNA bacteriophage GA. In a further preferred embodiment of the invention, the said RNA-bacteriophage is not MS2.

The capsid or virus-like particle of RNA-phage Qβ shows an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits not linked via disulfide bonds to other subunits within the capsid, or incompletely linked. However, typically more than about 80% of the subunits are linked via disulfide bridges to each other within the VLP. Qβ capsid protein also shows unusual resistance to organic solvents and denaturing agents.

WO 2004/007538 describes, in particular in Example 1 and Example 2, how to obtain VLP comprising or alternatively consisting of AP205 coat proteins, and hereby in particular the expression and the purification thereto. WO 2004/007538, and hereby in particular Example 1 and Example 2 thereof, is incorporated herein by way of reference. However, It is to note that the VLP-antigen conjugates described in WO 2004/007538 still contain the amount of host RNA within the VLP as obtained and resulted through expression. The VLP or the inventive VLP-antigen conjugates comprising coat proteins, mutants or fragments thereof, of the RNA-bacteriophage AP205, on the other hand, have been prepared or further treated by the inventive methods to exclude, reduce or eliminate the host RNA, preferably host nucleic acids.

Further RNA phage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J. Mol. Biol. 244:279-290, (1994)) have been disclosed.

In one preferred embodiment, the mutant coat proteins of the RNA phage have been modified by removal of at least one, or alternatively at least two, lysine residue by way of substitution or by way of deletion. In another embodiment, the mutant coat proteins of the RNA phage have been modified by addition of at least one, or alternatively at least two, lysine residue by way of substitution or by way of insertion. In one very preferred embodiment, the mutant coat protein is of RNA phage Qβ, wherein at least one, or alternatively at least two, lysine residue have been removed by way of substitution or by way of deletion. In an alternative very preferred embodiment, the mutant coat protein is of RNA phage Qβ, wherein at least one, or alternatively at least two, lysine residue have been added by way of substitution or by way of insertion. In one further preferred embodiment, the mutant coat protein of RNA phage Qβ has an amino acid sequence selected from any one of SEQ ID NO:23-27. The deletion, substitution or addition of at least one lysine residue allows varying the degree of coupling, i.e. the amount of antigen of the invention per subunits of the VLP of the RNA-phages, in particular, to match and tailor the requirements of the vaccine. The construction, expression and purification of the above indicated Qβ coat proteins, mutant Qβ coat protein VLPs and capsids, respectively, are described in WO 02/056905. In particular is hereby referred to Example 18 of above mentioned application. It is to be noted that the VLP-antigen conjugates described in the prior art such as in WO 02/056905 still contain the amount of host RNA within the VLP as obtained and resulted through expression. The VLP or the inventive VLP-antigen conjugates comprising Qβ mutant coat proteins, on the other hand, have been prepared or further treated by the inventive methods to exclude, reduce or eliminate the host RNA, preferably host nucleic acids.

In a further preferred embodiment, the compositions and vaccines of the invention have an antigen density being from 0.05 to 4.0. The term "antigen density", as used herein, refers to the average number of antigen which is linked per subunit, and hereby preferably per coat protein of the VLP of a RNA phage. Thus, this value is calculated as an average over all the subunits or monomers of the VLP, in the composition or vaccines of the invention. In a further preferred embodiment of the invention, wherein the antigen has a molecular weight of equal or more than 8 KDa, the antigen density is, preferably between 0.1 and 1.5. In a further preferred embodiment, wherein the antigen preferably consists of 5-30 amino acids, the antigen density is, preferably, between 0.5 and 4.

In one preferred embodiment, the VLP comprises, or alternatively consists essentially of, or consists of mutant coat proteins, and/or fragments thereof, of a RNA-phage Qβ, fr, AP205 or GA In one preferred embodiment of the present invention, the virus-like particle comprises, or alternatively consists essentially of, or alternatively consists of coat proteins of Qβ, mutants or fragments thereof, wherein the coat proteins comprise, consist essentially of or alternatively consist of a mixture of either one of the foregoing mutants and the corresponding A1 protein.

Assembly-competent mutant forms of AP205 VLPs, including AP205 coat protein with the substitution of proline at amino acid 5 to threonine or asparagine at amino acid 14 to aspartic acid, may also be used in the practice of the invention and leads to other preferred embodiments of the invention.

The crystal structure of several RNA bacteriophages has been determined (Golmohammadi, R. et al., Structure 4:543-554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present invention. Another advantage of the VLPs derived from RNA phages is their high expression yield in bacteria, in particular in *E. coli*, that allows production of large quantities of material at affordable cost.

In another preferred embodiment of the invention, the composition further comprises at least one polyanionic macromolelcule bound to the VLP. Preferably said polyanionic macromolelcule is packaged inside the VLP. In again a further preferred embodiment, the at least one polyanionic macromolecule is selected from the group consisting of (a) polyanionic polypeptides; (b) polyanionic saccharides, and wherein preferably said polyanionic saccharide is not LPS; (c) polyanionic organic polymers and (d) nucleic acids, wherein preferably said nucleic acid is not a Toll-like receptor ligand, preferably not an immunostimulatory nucleic acid.

In a still further preferred embodiment, the at least one polyanionic macromolecule is a nucleic acid, wherein said nucleic acid is not a Toll-like receptor ligand. In a still further preferred embodiment, the nucleic acid comprises, or consists of, more than 20 nucleotides. In one further preferred embodiment, the nucleic acids is a tRNA. tRNA can be purchased from chemical companies or extracted from organisms. Preferred tRNA for this invention is, for example, wheat germ tRNA or yeast tRNA. In another preferred embodiment, the nucleic acid is a DNA, wherein the DNA does not contain CpG motif and does not stimulate TLR9.

In preferred embodiments, the polyanionic polypeptide is selected from a group consisting of: (a) polyglutamic acid; (b) polyaspartic acid; (c) poly(GluAsp) and (d) any chemical modifications of (a) to (c). Examples for chemical modifications include, but are not limited to glycosylations, acetylations, and phosphorylations.

In other preferred embodiments of the invention, the polyanionic saccharide is selected from a group consisting of (a) anionic dextrans; (b) phospho cellulose; (c) polyglucoronic acid; (d) polygalacturonic acid; (e) polysialic acid; (f) hyaluronic acid and (g) glycosaminoglycans. In further preferred embodiments, the anionic dextran is selected from a group consisting of (a) dextran sulfate; (b) carboxylmethyl dextran; (c) sulfopropyl dextran; (d) methyl sulfonate dextran and (e) dextrane phosphate. In another further preferred embodiment glycoaminoglycan is selected from the group consisting of (a) heparin; (b) heparan sulfate; (c) dermatan sulfate; (d) chondroitin sulfate; and (e) keratan sulfate.

In another preferred embodiment of the invention, the polyanionic organic polymer is selected from the group consisting of (a) polyvinylsulfate and (b) polyacrylates.

In certain preferred embodiments of the invention, the molecular weight of the at least one polyanionic macromolecule is from about 2,000 to about 200,000 Dalton, the lowest molecular weight is preferably at least about 3000 Dalton, more preferably at least about 5000 Dalton, even more preferably at least about 7000 Dalton. the highest molecular weight is preferably at most about 200,000 Dalton, preferably at most about 180,000 Dalton, even more preferably at most about 160,000 Dalton, still more preferably at most about 150,000 Dalton.

Depending on the nature of the polyanionic macromolecule, the preferred molecular weight range varies. For example, for a polyanionic polypeptide, in particular for polyglutamic acids and polyaspartic acids, the preferred molecule weight is from 5000 Dalton to 150,000 Dalton. The lowest molecular weight is hereby preferably at least about 5000 Dalton, more preferably at least about 10,000 Dalton, even more preferably at least about 30,000 Dalton. The highest molecular weight is hereby preferably at most about 150,000 Dalton, preferably at most about 120,000 Dalton, even more preferably at most about 100,000 Dalton.

In a very preferred embodiment, the composition of the invention comprises at least one polyanionic macromolecule, wherein preferably said polyanionic macromolecule is at least one polyanionic polypeptide, and even more preferably wherein said polyanionic macromolecule is at least one polyglutamic acid and/or polyaspartic acid.

Polyanionic macromolelcules can be conveniently purchased from chemical companies. For example, polyglutamic acids and polyaspartic acids can be purchased from Sigma (Sigma, New Jersey, USA), covering a wide range of molecular weights (polyglutamic acid: 750-1.500, 1.500-3.000, 3.000-15.000, 15.000-50.000, 50.000-100.000; polyaspartic acid: 5.000-15.000, 15.000-50.000). The molecular weights are determined based on viscosity (Idelson, M. & Blout, E. R. (1958) J. Am. Chem. Soc. 80, p. 4631) and LALLS methods, i.e. low angle laser light scattering.

Polygalacturonic acid (MW, 25.000-50000) can be purchased from Fluka (Fluka, Buchs, Switzerland), dextran sulfate (MW, 5.000, 8.000 and 10000) from Sigma, dextran sulfate (MW, 100.000) from Fluka. The molecular weight is determined by LALLS, viscosity or gel filtration methods. Organic polymers such as polyvinyl sulfate (MW ~170.000) are purchasable from Aldrich.

In a further aspect, the invention provides a method of preparing the composition of the invention and a VLP of an RNA-bacteriophage-antigen conjugate, respectively, comprising the steps of (a) recombinantly producing a virus-like particle (VLP) with at least one first attachment site by a host, wherein said VLP comprises coat proteins, mutants or fragments thereof, of an RNA-bacteriophage; (b) incubating said VLP with solutions comprising metal ions capable of hydrolyzing the host RNA, preferably host nucleic acids; and (c) linking at least one antigen with at least one second attachment site to said VLP obtained from (a) or (b), preferably said VLP obtained from step (b). In preferred embodiments, the metal ions are selected from zinc (Zn) ions, copper (Cu) ions and iron (Fe) ions. Further preferably the incubating of said VLP step is followed by at least one step of purifying said VLP, preferably by dialysis to remove digested nucleic acids.

In another aspect, the invention provides a method to prepare the composition of the invention and a VLP of an RNA-bacteriophage-antigen conjugate, respectively, comprising the steps of: (a) recombinantly producing a virus-like particle (VLP) with at least one first attachment site by a host, wherein said VLP comprises coat proteins, mutants or fragments thereof, of an RNA-bacteriophage; (b) incubating said VLP with RNase; and (c) linking at least one antigen with at least one second attachment site to said VLP obtained from step (a) or (b), preferably said VLP obtained from step (b). In a preferred embodiment, the RNase is RNase A.

In another preferred embodiment, said incubating of said VLP with said RNase, preferably said RNase A is carried out in a low ion strength buffer, wherein preferably said low ion strength buffer has a concentration of lower than 50 mM, more preferably of lower than 40 mM and even more preferably of equal or lower than 30 mM, and wherein further preferably said low ion strength buffer has a concentration of 30 mM. Further preferably the incubating of said VLP step is followed by at least one step of purifying said VLP, preferably by dialysis to remove digested nucleic acids.

In a further aspect, the invention provides a method of preparing the composition of the invention and a VLP of an RNA-bacteriophage-antigen conjugate, respectively, comprising the steps of: (a) recombinantly producing a virus-like particle (VLP) with at least one first attachment site by a host, wherein said VLP comprises coat proteins, mutants or fragments thereof, of an RNA-bacteriophage; (b) disassembling said virus-like particle to said coat proteins, mutants or fragments thereof, of said RNA-bacteriophage; (c) purifying said coat proteins, mutants or fragments thereof; (d) reassembling said purified coat proteins, mutants or fragments thereof, of said RNA-bacteriophage to a virus-like particle, wherein said virus-like particle is essentially free of host RNA, preferably host nucleic acids; and (e) linking at least one antigen with at least one second attachment site to said VLP obtained from step (d). In a further preferred embodiment, the reassembling of purified coat proteins is effected in the presence and/or by addition of at least one polyanionic macromolecule. This inventive method is in particular advantageous since it allows, in particular by way of its disassembling step, the release of essentially all of the host nucleic acids.

In a preferred embodiment of the invention, the disassembling of said virus-like particle is preferably effected under denaturing conditions. Preferred denaturing conditions are high concentration of salt such as between 0.5M to 1M Magnesium chloride or more than 5M urea. Further preferably the step of purifying said coat proteins, mutants or fragments thereof is effected by cation exchange chromatography and/or size exclusion chromatography, in particular, to separate the host nucleic acids and said coat proteins, mutants or fragments thereof.

In a still further aspect, the invention provides a method of preparing the composition of the invention and a VLP of an RNA-bacteriophage-antigen conjugate, respectively, comprising the steps of (a) recombinantly producing coat proteins, mutants or fragments thereof, of an RNA-bacteriophage by a host; (b) purifying said coat proteins, mutants or fragments thereof; (c) forming a virus-like particle with at least one first attachment site, wherein said virus-like particle is essentially free of host RNA, preferably host nucleic acids; and (d) linking at least one antigen with at least one second attachment site to said VLP obtained from step (c). In a further preferred embodiment, the reassembling of purified coat proteins is effected in the presence and/or by addition of at least one polyanionic macromolecule.

In again a further aspect, the invention provides a method for producing the composition of the invention and a VLP of an RNA-bacteriophage-antigen conjugate, respectively, in which the VLP and the antigen are linked though at least one peptide bond. The method comprises the steps of: (a) recombinantly producing fusion proteins comprising coat proteins, mutants or fragments thereof, of an RNA-bacteriophage and an antigen by a host; (b) purifying said fusion proteins; (c) forming a virus-like particle, wherein said virus-like particle is essentially free of host RNA, preferably host nucleic acids. In a further preferred embodiment, the reassembling of purified fusion proteins is effected in the presence and/or by addition of at least one polyanionic macromolecule.

The alternative method comprises the steps of: (a) recombinantly producing a virus-like particle (VLP) by a host, wherein said VLP comprises a fusion protein comprising a coat protein, a mutant or a fragment thereof, of an RNA-bacteriophage and at least one antigen; disassembling said VLP to said fusion proteins, purifying said fusion proteins; reassembling said purified fusion proteins to a VLP, wherein said virus-like particle is essentially free of host RNA, preferably host nucleic acids. In a further preferred embodiment, the reassembling of purified fusion proteins is effected in the presence and/or by addition of at least one polyanionic macromolecule. In a preferred embodiment, the VLP is a VLP of RNA bacteriophage AP205.

In a very preferred embodiment of the invention, the composition of the invention comprises a VLP, essentially free of nucleic acids of host, of a RNA phage Qβ, AP205, fr or GA, even more preferably of RNA phage Qβ or GA, most preferably of RNA-phage Qβ and the composition further comprises at least one polyanionic molecule, preferably polyglutamic acid and/or polyaspartic acid. In another preferred embodiment of the invention, the composition comprises a VLP of RNA phage AP205 or fr, essentially free of nucleic acids of host, without further comprising at least one polyanionic macromolecule.

In a further preferred embodiment of the present invention, the at least one antigen is selected from the group consisting of proteins, polypeptides, carbohydrates, steroid hormones, organic molecules and haptens.

In one preferred embodiment of the invention, the at least one antigen is a hapten. Preferred haptens are hormones, drugs and toxic compounds. Further preferred are drugs, especially addictive drugs and drugs of abuse, respectively, in particular recreational drugs. Representative examples of such antigens include opioids and morphine derivatives, such as codeine, fentanyl, heroin, morphium and opium; relaxants such as diazepam; stimulants such as amphetamine, cocaine, MDMA (methylenedioxymethamphetamine), methamphetamine, methylphenidate and nicotine; hallucinogens such as PCP, LSD, mescaline and psilocybin; cannabinoids such as hashish and marijuana; as well as the desipramine/imipramine class of drugs and the nortriptyline/amitriptyline class of drugs. Therapy for nicotine addiction may also target nicotine derivatives such as O-succinyl-3'-hydroxymethyl-nicotine, metabolites including nornicotine and cotinine.

Detailed teachings of linking nicotine or nicotine derivatives or other drugs of abuse such as cocaine to VLPs have been disclosed in WO 2004/009116, and in particular on page 61, line 28 to page 66, line 13. The general and specific disclosure of WO 2004/009116 is hereby incorporated herein by way of reference.

Thus in one preferred embodiment, the at least one antigen is an organic molecule selected from addictive drugs, and wherein preferably said addictive drug is nicotine or cocaine, preferably nicotine.

In one preferred embodiment of the invention, the at least one antigen is a self antigen or a fragment or a variant thereof. Preferably the self antigen is a protein or a fragment thereof suited to induce an immune response against said self antigen. Thus, the invention provides vaccine compositions suitable for use in methods for preventing and/or attenuating diseases or conditions which are caused or exacerbated by "self" gene products (e.g., tumor necrosis factors). Thus, vaccine compositions of the invention include compositions which lead to the production of antibodies that prevent and/or attenuate diseases or conditions caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), Graves' disease, systemic lupus erythematosus (SLE), inflammatory autoimmune diseases, myasthenia gravis, immunoproliferative disease lymphadenopathy (IPL), angioimmunoproliferative lymphadenopathy (AIL), immunoblastive lymphadenopathy (IBL), rheumatoid arthritis, diabetes, psoriasis, myocarditis, multiple sclerosis, Alzheimer disease and osteoporosis.

In a very preferred embodiment of the invention, the at least one antigen of the invention is selected from the group consisting of: lymphotoxins (e.g. Lymphotoxin a (LT α), Lymphotoxin β (LT β)), lymphotoxin receptors, receptor activator of nuclear factor kB ligand (RANKL), vascular endothelial growth factor (VEGF), vascular endothelial growth factor receptor (VEGF-R), Interleukin-5, Interleukin-17, Interleukin-13, IL-23 p 19, Ghrelin, CCL21, CXCL12, SDF-1, M-CSF, MCP-1, Endoglin, GnRH, TRH, Eotaxin, Bradykinin, BLC, Tumor Necrosis Factor α, amyloid beta peptide (Aβ$_{1-42}$), Aβ$_{1-6}$, angiotensin, gastrin, progastrin, CETP, CCR5, C5a, CXCR4, Des-Arg-Bradykinin, or a fragment or a variant of the aforementioned antigens. As used for the aforementioned antigens, the term "fragment" of those antigens should refer to (i) any polypeptide comprising, or alternatively or preferably consisting of, at least 4, 5, preferably at least 6, 7, 8, 9, 10, 11, 12, 17, 18, 19, 20, 25 or 30 contiguous amino acids of the sequence of the corresponding antigen, or in case of a self antigen, of the human sequence of the wild type antigen as deposit in GeneBank or of the corresponding orthologs from any other animal, preferably of the human sequence of the wild type antigen as deposit in GeneBank; as well as (ii) any polypeptide having an amino acid sequence identity to the any one of the polypeptides of (i), wherein said amino acid sequence identity is more than 65%, preferably more than 80%, even more preferably more than 90% and again more preferably more than 95%. Furthermore, the term "fragment" of those antigens listed above should comprise at least one antigenic site. Preferably, the term "fragment" of those antigens listed above, as used herein, should refer to a polypeptide having a length of not more than 100 amino acids, preferably of not more than 80 amino acids, preferably of not more than 60 amino acids, more preferably of not more than 40 amino acids, again more preferably of not more than 30 amino acids, even more preferably of not more than 20 amino acids. Further preferably, the term "fragment" of those antigens listed above, as used herein and when referring to a self antigen, should refer to a polypeptide, when presented in accordance with the present invention, should be capable of inducing the production of antibody in vivo, which specifically binds to the corresponding antigens listed above. Moreover, the term "fragment" of those antigens listed above, as used herein, should preferably refer to a polypeptide resulting from at least one, preferably two, more preferably one truncation or internal deletion of the corresponding antigen. Methods to determine antigenic site(s) of a protein is known to the skilled person in the art. The U.S. provisional application 60/569,322 has elaborated some of these methods from the first paragraph of page 26 to the fourth paragraph of page 27 and these specific disclosures are incorporated herein by way of reference. It is to note that these methods are generally applicable to other polypeptide antigens, and therefore not restricted to IL-23 p 19 as disclosed in U.S. 60/569,322.

As used for the aforementioned antigens, the term "variant" of those antigens should refer to any polypeptide or any protein comprising, or alternatively or preferably consisting of, any naturally or genetically engineered polypeptide or protein having more than 70%, preferably more than 80%, even more preferably more than 90%, again more preferably more than 95%, and most preferably more than 97% amino acid sequence identity to the sequence of the antigens listed above, or in case of a self antigen, of the human sequence of the wild type antigen as deposit in GeneBank or of the corresponding orthologs from any other animal, preferably of the human sequence of the wild type antigen as deposit in GeneBank. Preferred methods of generating a variant of a protein is by genetic engineering, preferably by insertion, substitution, deletion or a combination thereof. A variant of a protein, when presented in accordance with the present invention, should be capable of inducing the production of antibody in vivo, which specifically binds to the corresponding antigens listed above.

Within this application, antibodies are defined to be specifically binding if they bind to the antigen of the invention, the antigen protein, the fragment of the antigen or the variant of the antigen with a binding affinity (Ka) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The affinity of an antibody can be readily determined by one of ordinary skill in the art typically and preferably by Scatchard analysis.

In one preferred embodiment, the at least one antigen is a GnRH-peptide (Gonadotropin Releasing Hormone, also known as Luteinizing Hormone Releasing Hormone, or LHRH). VLP-GnRH conjugates useful in the production of vaccines are disclosed in PCT/EP2005/053858, which is incorporated herein by reference in its entirety.

As used herein, the term "GnRH-peptide" is a peptide comprising, or alternatively essentially consisting of, or alternatively consisting of at least one, preferably one, mammalian GnRH, and hereby in particular at least one amino acid sequence, preferably one amino acid sequence of SEQ ID NO:1 or SEQ ID NO:28, preferably of SEQ ID NO:1, or fragments or variants thereof. In some embodiments, the GnRH peptide comprises N-terminal puroglutamic acid (pGlu or pE). In other embodiments, the GnRH peptide comprises C-terminal glycine amide (G-NH2). In another embodiment of the invention, the GnRH peptide comprises more than one GnRH peptide or fragment thereof, for example two as in SEQ ID NOs: 30-32, three or more GnRH peptides or fragments thereof in tandem. The tandem-GnRH peptide of the invention also comprises peptides in which the GnRH sequences are interconnected via spacer. The nature of the spacer group may greatly vary from one or more amino acids to a shorter or longer hydrocarbon chain and other compound groups or molecules.

In preferred embodiments, the GnRH peptide is associated with an amino acid linker, which comprises or consists of cysteine. In one further preferred embodiment, the amino acid linker is a cysteine fused to either the N- or the C-terminal of the GnRH peptide. In an even further preferred embodiment, the cysteine is fused to either the N- or the C-terminal of SEQ ID NO:1 (resulting in SEQ ID NO:4 or 5), preferably the N-terminal of SEQ ID NO:1 (SEQ ID NO:4). In another preferred embodiment, the linker CGG is fused to the N-terminal of the GnRH peptide, and preferably to the N-terminal of SEQ ID NO:1 or SEQ ID NO:28, more preferably to the N-terminal of SEQ ID NO:1, resulting in SEQ ID NO:2. In still another preferred embodiment, the linker GGC is fused to the C-terminal of the GnRH peptide, preferably to the C-terminal of SEQ ID NO:1 or SEQ ID NO:28, more preferably to the C-terminal of SEQ ID NO:1, resulting in SEQ ID NO:3.

This composition of the invention comprising GnRH as the at least one antigen can be administered to a mammal, such as pig to prevent the boar taint in the meat. The composition comprising GnRH can be administered to an animal, such as dog, cat, sheep, cattle to control their reproductive behaviour and/or to reduce their reproductivity. This modified VLP comprising GnRH can be administered to human having gonadal steroid hormone dependent cancers.

In a preferred embodiment, the at least one antigen of the invention is the amyloid beta peptide (Aβ$_{1-42}$) having the amino sequence DAEFRHDSGYEVHHQKL VFFAEDVG- SNKGAIIGLMVGGVVIA (SEQ ID NO:86), or a fragment thereof such as Aβ$_{1-6}$ having the amino sequence DAEFRH (SEQ ID NO:87). Accumulation of amyloid beta peptide presumably causes or exacerbates Alzheimer disease, thus the composition of the invention provides a method in treating or alleviating the disease condition. The coupling of various AP fragments to various VLPs such as Qβ or fr and their immunizations to mice have been disclosed in example 13, 15, 17 and 54 of WO02/056905 which are herein incorporated by way of reference. Fusion of the Aβ$_{1-6}$ fragment with viral coat proteins has been disclosed in example 7, 8, 9, 10, 11 of WO04/016282; the coupling of Aβ$_{1-6}$ to VLPs has been, furthermore, disclosed in example 13, 18, 20; the immunization of animals with VLP-Aβ$_{1-6}$ and the resulting vaccine effect have been disclosed in example 12, 14, 16, 17, 19 and 20 of WO04/016282.

In another preferred embodiment of the invention, the at least one antigen is Ghrelin or a fragment or a variant thereof. Ghrelin is a key regulator of feeding behaviour. Peripheral administration of ghrelin increased food uptake leading to increased body weight (Tschop et al, Nature 407:908-12). Thus, immunization against ghrelin, in accordance with the present invention, provides a method in treating obesity. Preferred ghrelin or ghrelin peptides have been disclosed within the pages 68-74 of WO04/009124. Ghrelin may be selected from other mammalian species besides human, such as dog and cat. Example 8, 9, 13, 15 of WO04/009124 discloses some of the methods of coupling ghrelin to VLPs and is herein incorporated by way of reference. In a further preferred embodiment, the at least one antigen is a ghrelin fragment comprising or alternatively consisting of amino acid sequence SEQ ID NO:77, SEQ ID NO: 78, SEQ ID NO:79 or SEQ ID NO:82 or SEQ ID NO:85. In another further preferred embodiment, the at least one antigen is a ghrelin fragment comprising or alternatively consisting of SEQ ID NO:83, wherein said composition of the invention is preferably administered to a dog; or SEQ ID NO:84, wherein said composition of the invention is preferably administered to a cat.

In another preferred embodiment of the invention, the at least one antigen is IL-23 p19 protein or IL-23 p19 fragment, as described in PCT/EP2005/004980, which is incorporated herein by reference in its entirety. In one preferred embodiment, the IL-23 protein comprises or alternatively consists essentially of, or consists of SEQ ID NO:6 or SEQ ID NO:7. In one preferred embodiment, the IL-23 fragment comprises, consists essentially of, or consists of any of the sequence selected from the group consisting of: (a) SEQ ID NOs: 8-9 and (b) SEQ ID NOs: 33-44 (c) fragments or variants of any one of the sequence of (a) and (b).

In another preferred embodiment of the invention, the at least one antigen is an angiotensin peptide or a fragment thereof. The term "angiotensin peptide" as used herein, shall encompass any peptide comprising the sequence, or fragments thereof, of angiotensinogen, angiotensin I or angiotensin II. The sequences are as follows: Angiotensinogen: DRVYIHPFHLVIHN (SEQ ID NO:108); Angiotensin I: DRVYIHPFHL (SEQ ID NO:109); Angiotensin II: DRVYIHPF (SEQ ID NO:110). Typically, one or more additional amino acids are added either at the C- or at the N-terminus of the angiotensin peptide sequences. Those additional amino acids are, in particular, valuable for an oriented and ordered association to the VLP. Further preferred embodiments have been disclosed in WO 03/031466 and herein incorporated by way of reference. In particular preferred Angiotensin fragments sequences with the second attachment site are selected from a group consisting of: a) CGGDRVYIHPF (SEQ ID NO:111); b) CGGDRVYIHPFHL (SEQ ID NO:112); c) DRVYIHPFHLGGC (SEQ ID NO:113); d) CDRVYIHPFHL (SEQ ID NO:114); e) CHPFHL (SEQ ID NO:115); f) CGPFHL (SEQ ID NO:116); g) CYIHPF (SEQ ID NO:117); h) CGIHPF (SEQ ID NO:118); i) CGGHPF (SEQ ID NO:119); j) DRVYIGGC (SEQ ID NO:120); k) DRVYGGC (SEQ ID NO:121); and l) DRVGGC (SEQ ID NO:122). Thus the composition of the invention provides a method in treating or alleviating the disease condition of hypertension. Detailed description of the preparation of the compositions and uses thereof have been disclosed in the WO 03/031466 and the entire application is incorporated herein by way of reference.

In yet another preferred embodiment of the invention, the at least one antigen is RANKL (Receptor Activator of NF kB Ligand), or a fragment or a variant thereof. RANKL is a transmembrane protein of 245 amino acids belonging to the TNF-superfamily. Part of the extracellular region (178 aa) can be shed by a TACE-like protease (Lum et al., *J Biol. Chem.* 274:13613 (1999)). The amino acid sequence of the extracellular part of human RANKL is shown in SEQ ID NO:221 (TrEMBL: 014788), the amino acid sequence of a human isoform is in SEQ ID NO:222 of WO02/056905. Sequences for the extracellular part of murine RANKL and an isoform are shown in SEQ ID NO:223 (TrEMBL:035235), and in SEQ ID NO:224 (TrEMBL:Q9JJK8 and TrEMBL:Q9JJK9) of WO02/056905)

It has been shown that RANKL is an essential factor in osteoclastogenesis. Inhibition of the interaction of RANKL with its receptor RANK can lead to a suppression of osteoclastogenesis and thus provide a means to stop excessive bone resorption as seen in osteoporosis and other conditions.

A human-RANKL construct with a N-terminal amino acid linker containing a cysteine residue fused to the extracellular part of RANKL is a very preferred embodiment of the invention. Further information about the physiological function of RANKL, methods for its expression have been disclosed in WO02/056905 page 62 to 64 and human-RANKL construct has been disclosed in example 6 of WO02/056905 and incorporated as reference herein. Further preferred embodiments of RANKL protein, fragment or RANKL peptide variant have been disclosed in WO03/039225 from paragraph 223 to 235 and herein incorporated by way of reference.

In another embodiment of the invention, the at least one antigen is Interleukin-17 (IL-17), or a fragment or a variant thereof. Human IL-17 is a 32-kDa, disulfide-linked, homodimeric protein with variable glycosylation (Yao, Z. et al., *J. Immunol.* 155: 5483-5486 (1995)). The amino acid sequence of human and mouse IL-17 are given in SEQ ID No: 228 (ACCESSION #: AAC50341) and in SEQ ID NO:229 (ACCESSION #: AAA37490) respectively of WO02/056905.

Clinical studies indicate IL-17 may be involved in many inflammatory diseases. High levels of IL-17 have been reported in patients with rheumatoid arthritis (Ziolkowska M. et al., *J. Immunol.* 164:2832-8 (2000)). Interleukin 17 has been shown to have an effect on proteoglycan degradation in murine knee joints (Dudler J. et al., *Ann Rheum Dis.* 59: 529-32 (2000)) and contribute to destruction of the synovium matrix (Chabaud M. et al., *Cytokine.* 12:1092-9 (2000)). Elevated levels of IL-17 mRNA have been found in mononuclear cells from patients with multiple sclerosis (Matusevicius, D. et al., *Mult. Scler.* 5: 101-104 (1999)). Elevated serum levels of IL-17 are observed in patients suffering Systemic Lupus Erythematosus (Wong C. K. et al, *Lupus* 9: 589-93 (2000)). In addition, IL-17 mRNA levels are increased in T cells isolated from lesional psoriatic skin (Teunissen, M. B. et al., *and J. Invest. Dermatol* 111: 645-649 (1998)). The involvement of IL-17 in rejection of kidney graft has also been demonstrated (Fossiez F. et al., *Int. Rev. Immunol.* 6:541-51 (1998)). The above findings suggest IL-17 may play a pivotal role in the initiation or maintenance of an inflammatory response (Jovanovic, D. V. et al., *J. Immunol.* 160: 3513-3521 (1998)). The human and mouse IL-17 sequence were given in SEQ ID NO:228 (AAC50341) and in SEQ ID NO:229 (AAA37490) of WO02/056905. Methods for expressing IL-17 have been described in page 69 of WO02/056905 and are incorporated herein by way of reference.

In another preferred embodiment of the invention the at least one antigen is Interleukin-13 (IL-13), or a fragment or a variant thereof. The amino acid sequence of precursor human IL-13 is shown in SEQ ID No: 230 and the amino acid sequence of processed human IL-13 is shown in SEQ ID No: 231 of WO02/056905. The first 20 amino acids of the precursor protein correspond to the signal peptide, and are absent of the processed protein.

IL-13 is a T helper 2-derived cytokine (like IL-4, IL-5) that has recently been implicated in allergic airway responses (asthma). Upregulation of IL-13 and IL-13 receptor has been found in many tumour types (e.g. Hodgkin lymphoma). Interleukin 13 is secreted by and stimulates the growth of Hodgkin and Reed-Sternberg cells (Kapp U et al., *J Exp Med.* 189: 1939-46 (1999)). Thus, immunization against IL-13 provides a way of treating among others the conditions described above, such as Asthma or Hodgkins Lymphoma. Methods for expressing IL-13 have been described in page 70 of WO02/056905, IL-13 constructs have been disclosed in example 9 of WO02/056905 and are incorporated herein as reference.

In yet another embodiment of the invention, the at least one antigen is Interleukin-5 (IL-5), or a fragment or a variant thereof. IL-5 is a lineage-specific cytokine for eosinophilopoiesis and plays an important part in diseases associated with increased number of eosinophils, such as asthma. The sequence of precursor and processed human IL-5 was provided in SEQ ID No: 233 and in SEQ ID No: 234 of WO02/056905, respectively, and the processed mouse amino acid sequence was shown in SEQ ID No: 235 of WO02/056905.

The biological function of IL-5 has been shown in several studies (Coffman R. L. et al., *Science* 245: 308-10 (1989); Kopf et al., *Immunity* 4:15-24 (1996)), which point to a beneficial effect of inhibiting IL-5 function in diseases mediated through eosinophils. Inhibition of the action of IL-5 provides thus a way of treatment against asthma and other diseases associated with eosinophils.

In another preferred embodiment of the invention, the at least one antigen is CCL-21, or a fragment or a variant thereof. In a related preferred embodiment, the antigenic is CXCL12, also termed SDF-1. It has been shown that chemokine receptors CCR7 and CXCR4 are upregulated in breast cancer cells and that CCL21 and CXCL12, the respective ligands, are highly expressed in organs representing the first destinations of breast cancer metastasis Müller et al. (*Nature* 410: 50-6 (2001)). Thus, immunization against CCL21 and CCL12, respectively, provides a way of treatment against metastatis spread in cancers, more specifically in breast cancer. In addition, the CCL12/CXCR4 chemokine-receptor pair has been shown to increase the efficacy of homing of more primitive hematopoietic progenitor cells to be bone marrow. In addition, CXCR4 and SDF-1 are supposed to influence the distribution of chronic lymphocytic leukemia cells. Thus, immunizing against CXCL12 provides a way of treatment against chronic lymphocytic leukemia. Furthermore, CCL12-CXCR4 interactions were reported to play a central role in CD4+ T cell accumulation in rheumatoid arthritis synovium (Nanki et al., 2000). Immunization against SDF-1 thus provides a way of treatment against rheumatoid arthritis.

The respective human and mouse sequences of CCL21 are to be found in SEQ ID No: 236 (Swissprot: SY21_human) and in SEQ ID NO:237 (Swissprot: SY21_mouse) of WO02/056905. The respective human and mouse sequences of CCL12 are shown in SEQ ID NO:238 (Swissprot: SDF1_human) and in SEQ ID NO:239 (Swissprot: SDF1_mouse) of WO02/056905.

In yet another embodiment of the invention, the at least one antigenic is B-lymphocyte chemoattractant (BLC, CXCL13), or a fragment or a variant thereof. The sequence of human and mouse BLC, respectively, are shown in SEQ ID NO:240 (Accession: NP_006410) and in SEQ ID NO:241 (Accession NP_061354) of WO02/056905. The signal peptide is the first 22 or 21 amino acids for human and for mouse respectively. Compositions of the invention with BLC preferably comprise the mature form of the protein.

Further physiological functions of BLC and methods for preparation of the composition have been disclosed in page 74 and 75 of WO02/056905 and are herein incorporated by way of reference. The immunization against BLC may provide a way of treatment against autoimmune diseases where lymphoid neogenesis is involved, such as rheumatoid synovitis and rheumatoid arthritis or type I diabetes.

In another specific embodiment, the at least one antigen of the invention is Eotaxin, or a fragment or a variant thereof. While IL-5 seems to be responsible for the migration of eosinophils from bone-marrow to blood, eotaxin is for the local migration in the tissue (Humbles et al., *J. Exp. Med.* 186: 601-12 (1997)). The sequence of human eotaxin-1 is shown in SEQ ID NO:242 (aa 1-23 corresponds to the signal peptide), the sequence of human eotaxin-2 is shown in SEQ ID NO:243 (aa 1-26 corresponds to the signal peptide), the sequence of human eotaxin-3 is shown in SEQ ID NO.: 244 (aa 1-23 corresponds to the signal peptide), the sequence of mouse eotaxin-1 is shown in SEQ ID No.: 245 (aa 1-23 corresponds to the signal peptide), and the sequence of mouse eotaxin-2 is shown in SEQ ID No.: 246 (aa 1-23 corresponds to the signal peptide) in WO02/056905 and therefore incorporated herein as reference. Further physiological, biochemical information of Eotaxin and its expression and construction in accordance with the invention are disclosed in page 75 and 76 of WO02/056905 and are incorporated herein as reference.

In yet another specific embodiment of the invention, the at least one antigen is Macrophage colony-stimulating factor (M-CSF or CSF-1), or a fragment or a variant thereof. Elevated expressions of M-CSF and its receptor have been associated with poor prognosis in several epithelial cancers such as breast, uterine and ovarian cancer. Structural data on the soluble form of M-CSF are available (crystal structure: Pandit et al., *Science* 258:1358-62 (1992)). The human sequence is shown in SEQ ID NO:247 (Accession: NP_000748) WO02/056905. Further preferred antigens of the present invention comprise the N-terminal fragment consisting of residue 33-181 or 33-185 of SEQ ID NO:247, corresponding to the soluble form of the receptor. The mouse sequence (Accession. NP_031804) is shown in SEQ ID NO:248 WO02/056905. Further biological information of M-CSF as well as its expression and construction of the composition according to the invention are disclosed in page 77 and 78 of WO02/056905 and are incorporated herein as reference.

In another preferred embodiment of the invention, the at least one antigen is a TNF-superfamily member, or a fragment or a variant thereof. The term "TNF-superfamily member" as used herein refers to a protein comprising a TNF-like domain. As used herein "TNF-superfamily member" includes all forms of TNF-superfamily members known in humans, cats, dog, mice, rats, eutherians in general, mammals in general as well as of other animals. TNF-superfamily members comprise a globular TNF-like extracellular domain of about 150 residues, which domain is classified as cd00184, pfam00229 or smart00207 in the conserved domain database CDD (Marchler-Bauer A, et al. (2003), "CDD: a curated Entrez database of conserved domain alignments", Nucleic Acids Res. 31: 383-387). TNF superfamily members as used herein include: TNFα, LTα, LTα/β, FasL, CD40L, TRAIL, RANKL, CD30L, 4-1BBL, OX40L, GITRL and BAFF, CD27L, TWEAK, APRIL, TL1A, EDA and any other polypeptide, in which a TNF-like domain can be identified.

In a further preferred embodiment, the at least one antigen of the invention is a TNF-peptide. "TNF-peptide" as used herein refers to a peptide comprising an amino acid sequence homologous to, that is in this context corresponding to, amino acid residues 3 to 8 of the consensus sequence for the conserved domain pfam 00229 (SEQ ID NO:45), preferably a peptide sequence homologous to amino acid residues 1 to 8 of the consensus sequence for the conserved domain pfam 00229 (SEQ ID NO:45), even more preferred a peptide sequence homologous to amino acid residues 1-13 of said consensus sequence. When the TNF-peptide is a peptide from human or mouse TNFα, said TNF-peptide consists of a peptide with a length of 6 to 18 amino acid residues, preferably with a length of 6 to 16 amino acid residues, more preferably with a length of 6 to 14 amino acid residues. A homologous peptide is such a peptide which is derived from a TNF-superfamily member of an animal, including a human being, particularly a mammalian TNF superfamily member, like e.g. mouse or human RANKL or mouse or human TNFα, and represents those amino acid residues that correspond to SEQ ID NO:45. These homologous peptides are identifiable to a skilled person by way of aligning the consensus sequence of the TNF superfamily (SEQ ID NO:45) with said TNF-superfamily member of the other animal. As explained above, a TNF-peptide comprises a peptide sequence corresponding to the above-mentioned amino acid residues of the consensus sequence. That is, outside of the specified homology region with the consensus sequence (e.g. amino acid residues 3 to 8 of the consensus sequence) the TNF-peptide may differ from a polypeptide that is a TNF-superfamily member. Preferably, however, the part of a TNF-peptide that is outside of the above-specified homology region with the consensus sequence, is at least 70% identical, more preferably at least 75%, 80%, 85%, 90%, 95%, 99% or even 100% identical with a polypeptide that is a TNF-superfamily member, preferably a mammalian TNF-superfamily member, more preferably a human TNF-superfamily member.

In a further preferred embodiment, the at least one antigen of the invention is human TNFα peptide (4-23) with the sequence SSRTPSDKPVAHVVANPQAE (SEQ ID NO: 88). In another further preferred embodiment of the invention, the antigen is a mouse TNFα peptide (4-23) with sequence SSQNSSDKPVAHVVANHQVE (SEQ ID NO:89). In another preferred embodiment, the antigen is the amino acid residues 22-32 of mature murine TNF-α VEEQLEWLSQR (SEQ ID NO:90). In yet another preferred embodiment, the antigen is the amino acid residues 22-32 of human TNF-α AEGQLQWLNRR (SEQ ID NO:91).

In a preferred embodiment, the composition of the invention comprising mouse TNFα peptide (4-23) is used for the manufacturing medicaments for treatment of autoimmune diseases or bone-related diseases, such as rheumatoid arthritis, systemic lupus erythematosus, inflammatory bowel disease, multiple sclerosis, diabetes, autoimmune thyroid disease, autoimmune hepatitis, psoriasis and psoriatic arthritis, and wherein said bone-related diseases are selected from the group consisting of osteoporosis, periondontis, periprostetic osteolysis, bone metasis, bone cancer pain, Paget's disease, multiple myeloma, Sjörgen's syndrome and primary biliary cirrhosis.

In one preferred embodiment of the invention, the self-antigen may be VEGF or VEGFR, or a fragments or a variant thereof as disclosed in page 55 and 56 of WO02/056905; Lymphotoxin 1, as disclosed in page 79 and 80 of WO02/056905; Lymphotoxin β and Lymphotoxin α and Lymphotoxin β receptor in page 93 of WO02/056905. The information is incorporated herein by way of reference.

In one preferred embodiment, the said at least one antigen is CXCR4, or a fragment or a variant thereof. The chemokine receptor CXCR4, also known as LESTR or fusin, belongs to the family of seven-transmembrane domain G-protein coupled receptors (Federsppiel et. al. (1993), Genomics 16:707). The only known ligand for CXCR4 is SDF-1 (Pelchen-Mattews, et. al. (1999) Immunol. Rev. 168:33). CXCR4 and SDF-1 are believed to be involved in many areas of human physiology like hematopoieses, T-cell activation and migration to sites of inflammation and T-cell homing, vascularization, brain development and embryogenesis (Murdoch, (2000) Immunol. Rev. 177:175.

CXCR4 was later identified as a co-receptor for HIV (Feng et al (1996) Science 272:872). Accordingly, HIV strains that necessity CXCR4 for entry are categorized as X4 strain. SDF-1 has been shown to block HIV-1 entry (Oberlin et al (1996), Nature 382:833; Bleul, et al (1996) Nature 382:829.

In one preferred embodiment of the invention, the at least one antigen comprises or consists of a fragment of a CXCR4 extracellular domain. A fragment of a CXCR4 extracellular domain has at least 6, 7, preferably at least 8, 9, 10 amino acids and a fragment of CCR5 extracellular domain has less than 30, preferably 20, more preferably 15, even more preferably 12 amino acids.

In one preferred embodiment, the at least one antigen comprises or consists of the N-terminal extracellular domain of CXCR4. In one further preferred embodiment, the N-terminal extracellular domain of CXCR4 comprises or consists of SEQ ID NO:66. In one preferred embodiment, the at least one antigen comprises or consists of a fragment of CXCR4 extracellular domain ECL2. Preferably said fragment has at least 6, preferably 7 amino acids. In a further preferred embodiment, the at least one antigen comprises or consists of a fragment of CXCR4 extracellular domain ECL2 having amino acid sequence as SEQ ID NO:65.

In one preferred embodiment of the invention, the at least one antigen is CCR5, or a fragment or a variant thereof. HIV R5 strains use the cell surface molecules CD4 and CCR5 for attachment and entry into macrophages and CD4+ T cells. CCR5 is a 7-transmembrane receptor with four extracellular domains: an N-terminal sequence and three loops exposed to the extracellular space, which are called subsequently PNt, ECL-1, ECL-2, and ECL-3, respectively. The natural CCR5 ligands, RANTES, MIP-1α, MIP-1β and analogs thereof are able to block the virus-coreceptor interaction and further cause the internalization of CCR5 (Lederman et al., 2004, Science 306, p485). CCR5 specific auto-antibodies have been found in 12.5% women that were repeatedly exposed to HIV but remained uninfected (Lopalco et al., 2000, J. Immunology 164, 3426). These antibodies were shown to bind the first extracellular loop (ECL-1) of CCR5 and could inhibit R5-tropic HIV infection of peripheral blood mononuclear cells (PBMC). Alloimmunisation in women led to CCR5 specific antibodies that were capable of inhibiting R5-HIV infection in vitro (Wang et al., 2002, Clin. Exp. Immunol. 129, 493).

Monoclonal α-CCR5 antibodies are able to prevent HIV infection (Olson et al., 1999, J. Virol. 73, 4145; Wu and LaRosa et al., 1997, J. Exp. Med. 186, 1373). Antibody binding to a cyclic peptide corresponding to the small extracellular loop ECL-2A (Arg168-Thr177) suppressed infection by HIV-1 R5 (Misumi et al., 2001, J. Virol. 75, 11614). Antibodies produced by immunizing monkeys with linear CCR5 peptides (from the N-terminal, the ECL-1, or the ECL-2 sequence) have viral inhibitory effect in vitro (Lehner et al., 2001, J. Immunology 166, 7446). The N-terminal domain of CCR5 was displayed on papillomavirus like particles and immunized monkey. Viral loads were lower, declined more rapidly and eventually became undetectable in all five tested monkeys (Chackerian et al., 2004, J. Virol. 78, 4037), although the plasma-associated virus in half of six control macaques declined to undetectable levels as well.

In one preferred embodiment of the invention, the at least one antigen comprises or consists of a fragment of a CCR5 extracellular domain. A fragment of a CCR5 extracellular domain has at least 6 or 7, preferably at least 8, 9 or 10 amino acids and a fragment of CCR5 extracellular domain has less than 35, preferably less than 30, preferably less than 20, more preferably less than 15, even more preferably less than 12 amino acids.

In one preferred embodiment, the fragment of a CCR5 extracellular domain comprises or consists of ECL2A. ECL2A, as generally understood in the art, starts preferably from the first amino acid of the ECL2 and stops preferably at threonine, which is right before cysteine in ECL2. In one further preferred embodiment, ECL2A comprises or alternatively consists of SEQ ID NO:62. In one preferred embodiment, ECL2A is cyclized. In a further preferred embodiment, the cyclized ECL2A comprises or alternatively consists of SEQ ID NO:62. In a further preferred embodiment, the ECL-2A is a cyclic peptide as in SEQ ID NO:61, wherein the peptide is cyclized by the C and G residue at both ends.

In one preferred embodiment, the antigen of the invention comprises or consists of CCR5 extracellular domain PNt. In one further preferred embodiment, the PNt domain comprises or preferably consists of SEQ ID NO:63.

In one preferred embodiment of the invention, the at least one antigen is gastrin and/or progastrin. Gastrin (G17) is a group of classical gut peptide hormonese with much lower amount in the colon and pancreas (Koh, Regulatory Peptides. 93, 37-44 (2000)). Gastrin is processed from its precursor progastrin (G34). Both gastrin and progestin exist in a C-terminal glycine-extended form and in a C-terminal phenylalanine amidated form.

Gastin is well known for its ability to stimulate gastric acid secretion (Pharmacol Ther. 98, 109-127 (2003)). The related hormone cholecystokinin (CCK), which has the C-terminal tetrapeptide amide as gastrin, is synthesized in the duodenum and is responsible for pancreatic enzyme secretion. While amidated G17 binds to CCK-2 receptor, CCK binds to both CCK-1 receptor and CCK-2 receptors (Steel. IDrugs. 5, 689-695 (2002)). The receptor for the gaycine-extended gastrin remains unclear. Recent data suggest that gastrin might promote the development of cancers of the gastrointestinal tract (Watson. Aliment Pharmacol Ther. 14, 1231-1247 (2000)). In contrast, non-amidated gastrins stimulate colonic mucosal growth, accelerate the early steps in colorectal carcinoma formation, and are elevated in the tumour and circulation of patients with colorectal cancer (Watson. Aliment Pharmacol Ther. 14, 1231-1247 (2000)).

In one preferred embodiment, the at least one antigen comprises or preferably consists of G17 (SEQ ID NO:50). In one further preferred embodiment, the at least one antigen comprises or consists of G17 with addition glycine at the C-terminus (SEQ ID NO:51). In one alternative further preferred embodiment, the at least one antigen comprises or preferably consists of G17 with the last amino acid F being amidated. In one preferred embodiment, the at least one antigen comprises or consists of progastrin G34 (SEQ ID NO:52). In one further preferred embodiment, the at least one antigen comprises or consists of progastrin G34 with additional glycine at the C-terminus (SEQ ID NO:53). In one alternative further preferred embodiment, the at least one antigen comprises or consists of progastrin G34 with the last amino acid F being amidated.

In one preferred embodiment, the at least one antigen comprises or consists of G17 1-9 fragment (SEQ ID NO:49), preferably with a linker sequence fused to its C-terminus, more preferably with a linker sequence SSPPPPC (SEQ ID NO:72) fused to the C-terminus.

In one very preferred embodiment, the at least one antigen fused with linker comprises or consists of an amino acid sequence as SEQ ID NO:54.

It is to note E at position one of sequence EGPWLEEEE (SEQ ID NO:49) as part of gastrin sequence could be E, pyro E or Q. When additional amino acid is fused to the N-terminus of EGPWLEEEE, E at position one of sequence EGPWLEEEE could be E or preferably Q.

In one preferred embodiment of the invention, the at least one antigen is C5a, or a fragment or a variant thereof. C5a, a 74-amino acid, 4-helix bundle glycoprotein (Fernandez and Hugli, J. Biol. Chem. 253, 6955-6964, 1978), is responsible for generating a number of diverse effects on cellular systems, especially neutrophils, endothelial cells and macrophages to induce local inflammations to combat infecting microorganisms (Ward P., Nat. Rev. Immunol. 4:133, 2004). However, by the same token, the excessive generation of C5a in sepsis leads to serious functional defects in neutrophils (Czermak et al., Nat. Med. 5:788, 1999; Huber-Lang et al., J. Immunol. 166:1193, 2001). Elevated activation of C5a has been also implicated in a number of primary and/or chronic inflammatory diseases, such as rheumatoid arthritis (Jose P. Ann Rheum. Dis. 49:747, 1990), psoriasis (Takematsu H., Arch. Dermatol. 129:74, 1993), adult respiratory distress syndrome (Langlois P., Heart Lung 18:71, 1989), reperfusion injury (Homeister, J. Annu. Rev. Pharmacol. Toxicol. 34:17, 1994), lupus nephritis and bullous pemphigoid.

In one preferred embodiment, the at least one antigen comprises or consists of a C5a. In a further preferred embodiment, the C5a protein has amino acid sequence of SEQ ID NO:57. In one preferred embodiment, the at least one antigen comprises or consists of a C5a fragment. In one further preferred embodiment, the C5a fragment having amino acid sequence as SEQ ID NO:59.

In one preferred embodiment of the invention, the at least one antigen is CETP, or a fragment or a variant thereof. Cholesteryl-ester transfer protein (CETP) is a plasma glycoprotein which mediates the exchange of cholesterol ester (CE) and triglycerides (TG) between High density lipoprotein (HDL) particles and apo B rich particles such as very-low density lipoprotein (VLDL) particles or low-density lipoprotein (LDL) particles. CETP also transfers phospholipids (PL). The human CETP cDNA encodes a protein of 476 amino acid and Mr of 53000, which through glycosylation gives rise to a glycoprotein of Mr 74000.

HDL is considered anti-atherogenic, as an inverse correlation between HDL-cholesterol level and coronary heart disease (CHD) has been observed (Barter P. J. and Rye K. -A. (1996) Atherosclerosis 121: 1-12). LDL and VLDL are in contrast pro-atherogenic lipoproteins. CETP deficiency in human is associated with increase HDL-c and decrease LDL-c levels, which are typically anti-atherogenic. Patients affected by the Metabolic Syndrome have low HDL-c, an enriched fraction of small dense LDL particles, mild to moderate hypertriglyceridemia, mild hypertension, truncal obesity and insulin resistance and are particularly at risk of CHD. Patients suffering from non-insulin-dependent diabetes mellitus or familial combined hyperlipidemia also have low HDL-c and are at risk of CHD (Barter P. J. and Rye K. -A. (1996) Atherosclerosis 121: 1-12).

In one preferred embodiment, the at least one antigen comprises or consists of a CETP fragment having amino acid sequence of SEQ ID NO:69.

In one preferred embodiment of the invention, the at least one antigen comprises or consists of Bradykinin, fragments or variants thereof. Bradykinin (BK, KRPPGFSPFR, SEQ ID NO:80) is a major vasodilator peptide and plays an important role in the local regulation of blood pressure, blood flow and vascular permeability (Margolius H. S, et al., *Hypertension*, 1995). Moreover several other biologic activities of Bradykinin have been described including contraction and relaxation of smooth muscles, induction of nociception and hyperalgesia and mediation of inflammatory responses. Bradykinin exerts its effects via the B2-receptor.

In one preferred embodiment of the invention, the at least one antigen comprises or consists of des-Arg9-Bradykinin, fragments or variants thereof. des-Arg9-BK (KRPPGFSPF, SEQ ID NO:81) has both overlapping and distinct functions from Bradykinin. Evidence suggests that des-Arg9-BK is rapidly generated after tissue injury and modulates most of the events observed during inflammatory processes including vasodilatation, increase of vascular permeability, plasma extravasation, cell migration, pain and hyperalgesia (Calixto J. B. et al., *Pain* 2000). Des-Arg9-BK exerts its effects via the B 1-receptor.

BK and Des-Arg9-BK have been reported to play a role in several inflammatory diseases. For example, B2 and B1-receptor upregulation in synovial fibroblasts and enhanced serum Kinin production was observed during the course of antigen-induced chronic or Rheumatoid Arthritis (RA) (Cruwys S. C. et al., *Br J Pharmacol*, 1994; Cassim B. et al., *Immunopharmacology* 1997). Experimental evidence suggests that both BK des-Arg9-BK play a role during the development of asthma. Elevated levels of BK and des-Arg9-BK were found in BALF of asthmatic patients (Christiansen S. C. et al., *Am. Rev. Dis.* 1992). BK and Des-Arg9-BK play roles in primary and chronic inflammatory diseases, in particular, arthritis and airway inflammation induced by allergens or particulate antigens, such as virus.

The invention further includes compositions which contain mimotopes of the antigens described herein. Further information about employing mimotope in the vaccine composition in accordance with the invention have been disclosed in page 83-85 of WO02/056905 and incorporated herein by way of reference.

The at least one antigen can be prepared by purification from a natural source, or preferably by recombinant expression, even more preferably in a bacterial expression system, most preferably in an *E. coli* system. For the purification purpose, the antigen of the invention is usually expressed as a fusion protein with a tag, such as the histidine tag, the Flag tag, the myc tag or the constant region of an antibody (Fc region). Typically but not necessarily an enterokinase cleavage site is between the antigen and the tag so that the tag can be cleaved. In another preferred embodiment, the at least one antigen with no longer than 50 amino acids is chemically synthesized.

It is to be noted that the VLP-antigen conjugates described in the prior art, such as WO02/056905, WO03/031446, WO03/039225, WO03/040164, WO04/009116, WO04/009124, WO04/016282, U.S. 60/569,322, WO 03/031466 in WO 2004/007538 and other incorporated references by that the present invention, still contain the amount of host RNA within the VLP as obtained and resulted from expression. The inventive VLP-antigen conjugates, on the other hand, have a reduced, or essentially eliminated, the amount of host RNA, preferably host nucleic acids, in accordance with the present invention.

In one embodiment of the invention, the VLP of the invention and the at least one antigen of the invention are fused through the at least one first and the at least one second attachment site, i.e. through at least one peptide bond. Such a fusion can, for example, be effected through fusion of the at least one antigen of the invention with the viral coat protein, the building block of the virus like particle, hereby typically by genetic engineering.

Gene encoding an antigen of the invention, preferably an antigen which is less than 100 amino acids, more preferably less than 80 amino acids, even more preferably less than 60 amino acids, more preferably less than 40, most preferably less than 20 amino acids, is in-frame ligated, either internally or preferably to the N- or the C-terminus to the gene encoding the coat protein of the VLP. Fusion may also be effected by inserting sequences of the antigen into a variant of a VLP subunit where part of the subunit sequence has been deleted, that are further referred to as truncation mutants. Truncation mutants may have N- or C-terminal, or internal deletions of part of the sequence of the VLP coat protein. Preferably, the fusion protein shall retain the ability of assembly into a VLP which can be examined by electronmicroscopy.

Flanking amino acid residues may be added to increase the distance between the coat protein and the foreign epitope. Glycine and serine residues are particularly favored amino acids to be used in the flanking sequences. Such a flanking sequence confers additional flexibility, which may diminish the potential destabilizing effect of fusing a foreign sequence into the sequence of a VLP coat protein and may diminish the interference with the assembly by the presence of the foreign epitope.

In one preferred embodiment, the modified VLP is a mosaic VLP, wherein preferably said mosaic VLP comprises or alternatively consists of at least one fusion protein and at least one viral coat protein.

In preferred embodiments, the at least one antigen of the invention, preferably an antigen consisting of less than 50 amino acids can be fused to a number of viral coat proteins, by way of examples, to the C-terminus of a truncated form of the A1 protein of Qβ (Kozlovska, T. M., et al., Intervirology 39:9-15 (1996)), or being inserted between position 72 and 73 of the CP extension. For example, Kozlovska et al., (Intervirology, 39: 9-15 (1996)) describe Qβ μl protein fusions where the epitope is fused at the C-terminus of the QβCP extension truncated at position 19. As another example, the antigen can be inserted between amino acid 2 and 3 of the fr CP, leading to an antigen-fr CP fusion protein (Pushko P. et al., Prot. Eng. 6:883-891 (1993)). Furthermore, antigen can be fused to the N-terminal protuberant β-hairpin of the coat protein of RNA phage MS-2 (WO 92/13081).

In one preferred embodiment of the invention, the at least one antigen is fused to the N- or the C-terminus of the coat protein, mutants or fragments thereof, of AP205 bacteriophage. In one further preferred embodiment, the at least one antigen is fused to the N- or the C-terminus of the coat protein, mutants or fragments thereof, of AP205 through a spacer. In general, flexible spacers are favoured. The engineering of the spacer between the first polypeptide and the second polypeptide can be achieved by recombinant DNA technology. In one specific embodiments of the invention, the amino acid sequence of the spacer is selected from a group consisting of: (a) GSGG (SEQ ID NO:92); (b) GSG (SEQ ID NO:93); (c) GTAGGGSG (SEQ ID NO:94); and (d) GSGTAGGGSGS (SEQ ID NO:95).

In one preferred embodiment of the present invention, the composition comprises or alternatively consists essentially of a virus-like particle with at least one first attachment site, linked to at least one antigen with at least one second attachment site via at least one covalent bond, preferably the covalent bond is a non-peptide bond. The typical inherent highly repetitive and organized structure of the VLPs of RNA phages, advantageously contributes to the ability to display the antigen of the invention in a preferably highly ordered and repetitive array, which is further ensured by oriented and defined linkages as disclosed by the present invention.

In a preferred embodiment of the present invention, the first attachment site comprises, or preferably is, an amino group, preferably the amino group of a lysine residue. In another preferred embodiment of the present invention, the second attachment site comprises, or preferably is, a sulfhydryl group, preferably a sulfhydryl group of a cysteine. In another preferred embodiment of the present invention, the second attachment site comprises, or preferably is a maleimido group that that is associated, preferably, covalently associated with the at least one antigen.

U.S. Pat. No. 5,698,424 describes a modified coat protein of bacteriophage MS-2 capable of forming a capsid, wherein the coat protein is modified by an insertion of a cysteine residue into the N-terminal hairpin region, and by replacement of each of the cysteine residues located external to the N-terminal hairpin region by a non-cysteine amino acid residue. The inserted cysteine may then be linked directly to a desired molecular species to be presented such as an epitope or an antigenic protein.

We note, however, that the presence of an exposed free cysteine residue in the capsid may lead to oligomerization of capsids by way of disulfide bridge formation. Moreover, attachment between capsids and antigenic proteins by way of disulfide bonds are labile, in particular, to sulfhydryl-moiety containing molecules, and are, furthermore, less stable in serum than, for example, thioether attachments (Martin F J. and Papahadjopoulos D. (1982) Irreversible Coupling of Immunoglobulin Fragments to Preformed Vesicles. J. Biol. Chem. 257: 286-288).

Therefore, in a further very preferred embodiment, the linkage of the VLP and the at least one antigen does not comprise a disulfide bond. Further preferred hereby, the at least one second attachment comprise, or preferably is, a sulfhydryl group. Moreover, in again a very preferred embodiment of the invention, the linkage of the VLP and the at least one antigen does not comprise a sulphur-sulphur bond. In a further very preferred embodiment, said at least one first attachment site is not or does not comprise a sulfhydryl group of a cysteine. In again a further very preferred embodiment, said at least one first attachment site is not or does not comprise a sulfhydryl group.

In a very preferred embodiment of the present invention, the first attachment site comprises, or preferably is, an amino group, more preferably an amino group of a lysine and the second attachment site comprises, or preferably is, a sulfhydryl group, more preferably a sulfhydryl group of a cysteine.

In one preferred embodiment of the invention, the at least one antigen is linked to the VLP, by way of chemical cross-linking, typically and preferably by using a heterobifunctional cross-linker. In preferred embodiments, the hetero-bifunctional cross-linker contains a functional group which can react with the preferred first attachment sites, i.e. with the amino group, preferably of lysine residue(s) of the VLP, and a further functional group which can react with the preferred second attachment site, i.e. a sulfhydryl group, preferably of cysteine(s) residue inherent of, or artificially added to the antigen of the invention, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available, for example, from the Pierce Chemical Company. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the antigen and the VLP upon coupling. Preferred cross-linkers belonging to this class include, for example, SPDP and Sulfo-LC-SPDP (Pierce).

In one preferred embodiment of the invention, the inventive composition further comprises a linker. Thus, in some embodiments, engineering of a second attachment site onto the antigen is achieved by the association of a linker comprising, or alternatively consisting of, an amino acid suitable as a second attachment site according to the disclosures of this invention. Therefore, in a preferred embodiment of the present invention, a linker is associated to the antigen by way of at least one covalent bond, preferably, by at least one, typically one peptide bond. Preferably, the linker comprises, or alternatively consists of, the second attachment site. In a further preferred embodiment, the linker comprises a sulfhydryl group of a cysteine residue. In another preferred embodiment, the linker is a cysteine residue.

The selection of a linker will be dependent on the nature of the antigen, on its biochemical properties, such as pI, charge distribution and glycosylation. In general, flexible amino acid linkers are favored. In a further preferred embodiment of the present invention, the linker consists of amino acids, wherein further preferably the linker consists of at most 25, preferably at most 20, more preferably at most 15 amino acids. In an again preferred embodiment of the invention, the amino acid linker contains no more than 10 amino acids. Preferred embodiments of the linker are selected from the group consisting of: (a) CGG (SEQ ID NO:96); (b) N-terminal gamma 1-linker (e.g. CGDKTHTSPP, SEQ ID NO:97); (c) N-terminal gamma 3-linker (e.g. CGGPKPSTPPGSSGGAP, SEQ ID NO:48); (d) Ig hinge regions; (e) N-terminal glycine linkers (e.g. GCGGGG, SEQ ID NO:98); (f) $(G)_k C(G)_n$ with n=0-12 and k=0-5; (g) N-terminal glycine-serine linkers ((GGGGS)n, n=1-3 with one further cysteine (for example SEQ ID NO:99, which corresponds to an embodiment wherein n=1); (h) $(G)_k C(G)_m (S)_l (GGGGS)_n$ with n=0-3, k=0-5, m=0-10, l=0-2 (for example SEQ ID NO:100, which corresponds to an embodiment wherein n=1, k=1, l=1 and m=1); (i) GGC; (k) GGC-NH2; (l) C-terminal gamma 1-linker (e.g. DKTHTSPPCG, SEQ ID NO:101); (m) C-terminal gamma 3-linker (e.g. PKPSTPPGSSGGAPGGCG, SEQ ID NO:102); (n) C-terminal glycine linkers (GGGGCG, SEQ ID NO:103); (o) $(G)_n C(G)_k$ with n=0-12 and k=0-5; (p) C-terminal glycine-serine linkers ((SGGGG)n n=1-3 with one further cysteine (for example SEQ ID NO:104, which corresponds to an embodiment wherein n=1); (q) (G)m (S)1 (GGGGS)n (G)oC(G)$_k$ with n=0-3, k=0-5, m=0-10, l=0-2, and o=0-8 (for example SEQ ID NO:105, which corresponds to an embodiment wherein n=1, k=1, l=1, o=1 and m=1). In a further preferred embodiment the linker is fused to the N-terminus of the antigen. In another preferred embodiment of the invention, the linker is fused to the C-terminus of the antigen.

Preferred linkers according to this invention are glycine linkers (G)n further containing a cysteine residue as second attachment site, such as N-terminal glycine linker (GCGGGG, SEQ ID NO:98) and C-terminal glycine linker (GGGGCG, SEQ ID NO:103). Further preferred embodiments are C-terminal glycine-lysine linker (GGKKGC, SEQ ID NO: 106) and N-terminal glycine-lysine linker (CGKKGG, SEQ ID NO: 107), GGCG a GGC or GGC-NH2 ("NH2" stands for amidation) linkers at the C-terminus of the peptide or CGG at its N-terminus. In general, glycine residues will be inserted between bulky amino acids and the cysteine to be used as second attachment site, to avoid potential steric hindrance of the bulkier amino acid in the coupling reaction.

In an alternative embodiment of the invention, the linker is associated with the antigen of the invention by chemical interaction, preferably by at least one covalent bond which is not a peptide bond.

Other methods of linking the antigen to the VLP include methods wherein the antigen is cross-linked to the VLP, using the carbodiimide EDC, and NHS. The antigen of the invention may also be first thiolated through reaction, for example with SATA, SATP or iminothiolane. In further methods, the antigen is attached to the VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the VLP.

In one preferred embodiment, the first attachment site comprises, or preferably is, a sulfhydryl group, even more preferable a sulfhydryl group of a cysteine naturally or artificially added to the coat protein comprised, or alternatively consisted essentially of by the VLP. The second attachment site is the maleimido group of a linker, such as MBS (m-Maleimidobenzoyl-N-hydroxysuccinimide ester) or SMPH (Succinimidyl-6-[β-maleimidopropionamido]hexanoate), which is chemically associated with the antigen, preferably covalently associated with the antigen, more preferably covalently associated with an amino group of the antigen, even more preferably covalently associated by a NHS-ester group of the linker with the amino group of the N-terminus amino acid of the antigen. In one preferred embodiment, the antigen, preferably an antigen of no more than 70, more preferably no more than 50, even more preferably no more than 30 amino acids, is preferably chemically synthesized and the maleimido group is preferably associated to the amino group of the N-terminus amino acid. The first attachment site and the second attachment site are linked through a thio-ether bond.

In one preferred embodiment of the composition, the first attachment site comprises, or preferably is, an amino group, preferably an amino group of a lysine and said second attachment site comprises, or preferably is a maleimido group. The first attachment site, the amino group of a lysine may be naturally occurring or artificially added to the coat protein. Preferably the second attachment site is the group of a linker as elaborated in the above paragraph. The amino group of the VLP is derivatized by a hetero-bifunctional crosslinker, such as N-Succinimidyl-5-acetylthioacetate (SATA) or 2-Iminothiolane, into a sulfhydryl group, which is then reactive to the maleimido group of the linker.

Preferred linkers comprising at least one maleimido group are, for example, SMPH, Sulfo-MBS. Further preferred linkers are Sulfo-EMCS, Sulfo-GMBS, Sulfo-SIAB, Sulfo-SMPB, Sulfo-SMCC, SVSB, SIA and other cross-linkers available, for example, from the Pierce Chemical Company, and having one functional group reactive towards amino groups and one functional group reactive towards sulfhydryl groups.

In other embodiments of the present invention, the VLP and the at least one antigen of the invention are linked via chemical interactions, wherein at least one of these chemical interactions is not a covalent bond. Linking of the VLP to the antigen can be effected by biotinylating the VLP and expressing the antigen as a streptavidin-fusion protein. Alternatively, both the antigen and the VLP, are biotinylated, for example as described in WO 00/23955. Other binding pairs, such as ligand-receptor, antigen-antibody, can also be used as coupling reagent in a similar manner as biotin-avidin.

In one aspect, the invention provides a vaccine composition comprising the composition of the invention. Preferably the vaccine composition further comprises a suitable buffer. The antigen linked to the VLP in the vaccine composition may be of animal, preferably mammalian or human origin. In preferred embodiments, the antigen is of human, bovine, dog, cat, mouse, rat, pig or horse origin.

In one preferred embodiment, the vaccine composition further comprises at least one adjuvant. The administration of the at least one adjuvant may hereby occur prior to, contemporaneously or after the administration of the inventive composition. Examples of the at least one adjuvant are aluminium salts, monophosphoryl lipid A (MPL), incomplete Freund's adjuvant (IFA). Adjuvants induce the formation of a local antigen depot.

In another preferred embodiment, the vaccine composition of the invention is devoid of an adjuvant. An advantageous feature of the present invention is the high immunogenicity of the composition, even in the absence of adjuvants. The absence of an adjuvant, furthermore, minimizes the occurrence of unwanted inflammatory T-cell responses representing a safety concern in the vaccination against self antigens. Thus, the administration of the vaccine of the invention to a patient will preferably occur without administering at least one adjuvant to the same patient prior to, contemporaneously or after the administration of the vaccine.

The invention further discloses a method of immunization comprising administering the vaccine of the invention to an animal or a human. The animal is preferably a mammal, such as cat, sheep, pig, horse, bovine, dog, rat, mouse and particularly a human. The vaccine may be administered to an animal or a human by various methods known in the art, but will normally be administered by injection, infusion, inhalation, oral administration, or other suitable physical methods. The conjugates may alternatively be administered intramuscularly, intravenously, transmucosally, transdermally, intranasally, intraperitoneally or subcutaneously. Components of conjugates for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Vaccines of the invention are said to be "pharmacologically acceptable" if their administration can be tolerated by a recipient individual. Further, the vaccines of the invention will be administered in a "therapeutically effective amount" (i.e., an amount that produces a desired physiological effect). The nature or type of immune response is not a limiting factor of this disclosure. Without the intention to limit the present invention by the following mechanistic explanation, the inventive vaccine might induce antibodies which bind to the antigen of the invention and thus reducing its concentration and/or interfering with its physiological or pathological function.

In one embodiment, the invention provides a pharmaceutical composition and an acceptable pharmaceutical carrier. When a vaccine of the invention is administered to an individual, it may be in a form which contains salts, buffers, adjuvants, or other substances which are desirable for improving the efficacy of the conjugate. Examples of materials suitable for use in preparation of pharmaceutical compositions are provided in numerous sources including REMINGTON'S PHARMACEUTICAL SCIENCES (Osol, A, ed., Mack Publishing Co., (1990)).

The invention provides a method of using the compositions of the invention for treating and/or attenuating diseases or conditions in which the at least one antigen of the invention exerts an important pathological function in an animal or in human.

In another aspect, the invention provides for the use of the composition of the invention for the manufacture of a medicament for treatment of diseases in an animal or in human, in which the at least one antigen of the invention exerts an important pathological function.

EXAMPLES

For the sake of simplicity, the terms "prior art VLPs" and "VLPs of the invention" as well as the more specific terms "prior art Qβ VLPs", "Qβ VLPs of the invention", "prior art AP205 VLPs" and "AP205 VLPs of the invention" and the like are, in particular, used within this example section and in the brief description of the figures section. The terms "prior art VLPs" as well as the more specific terms "prior art Qβ VLPs", "prior art AP205 VLPs" and the like, as used within this example section, refer to VLPs obtained by recombinant expression from *E. coli* and subsequent purification as described in WO 02/056905, WO 04/007538 or, in particular, in EXAMPLE 1 of the present application. The terms "VLPs of the invention" as well as the more specific terms "Qβ VLPs of the invention", "AP205 VLPs of the invention" and the like, as used within this example section, refer to VLPs in accordance with this invention, and, in particular, to VLPs obtained by the inventive methods. Moreover, for further sake of simplicity, the terms "reassembled VLPs" as well as the more specific terms "reassembled Qβ VLPs", "reassembled AP205 VLPs" and the like, are used within this example section, for typically and preferably referring to VLPs obtained by the inventive methods as described in claims 35, 37, 39 or 41. Furthermore, the terms "RNase treated VLPs" as well as the more specific terms "RNase treated Qβ VLPs", "RNase treated AP205 VLPs" and the like, are used within this example section, for typically and preferably referring to VLPs obtained by the inventive methods as described in claim 43. Again furthermore, the terms "metal ion treated VLPs" as well as the more specific terms "metal ion treated Qβ VLPs", "metal ion treated AP205 VLPs" and the like, are used within this example section, for typically and preferably referring to VLPs obtained by the inventive methods as described in claim 44.

Example 1

Expression of Qβ Coat Protein and Purification of the Resulting Prior Art Qβ VLP

*E. coli* JM109 was transformed with Qβ coat protein expressing plasmids. 5 ml of LB liquid medium containing 20 μg/ml ampicillin was inoculated with a clone transformed with Qβ coat protein expression plasmid. The inoculated culture was incubated at 37° C. for 16-24 hours without shaking. The culture was subsequently diluted 1:100 in 100-300 ml of fresh LB medium, containing 20 μg/ml ampicillin, and incubated at 37° C. overnight without shaking. The resulting second inoculum was diluted 1:50 in M9 medium containing 1% Casamino acids and 0.2% glucose in flasks, and incubated at 37° C. overnight under shaking. The cells were pelleted by centrifugation and frozen for storage.

Purification

Solutions and buffers for the purification procedure:
1. Lysis buffer LB
   50 mM Tris-HCl pH8.0 with 5 mM EDTA, 0.1% tritonX100 and freshly prepared PMSF at a concentration of 5 micrograms per ml without lysozyme and DNAse.
2. Saturated ammonium sulphate in water (SAS)
3. Buffer NET.
   20 mM Tris-HCl, pH 7.8 with 5 mM EDTA and 150 mM NaCl.
4. PEG
   40% (w/v) polyethylenglycol 6000 in NET Disruption and lysis Frozen cells were resuspended in LB at 2 ml/g cells. The mixture was sonicated with 22 kH five times for 15 seconds, with intervals of 1 min to cool the solution on ice. The lysate was then centrifuged at 14000 rpm, for 1 h using a Janecki K 60 rotor. The centrifugation steps described below were all performed using the same rotor, except otherwise stated. The supernatant was stored at 4° C., while cell debris was washed twice with LB. After centrifugation, the supernatants of the lysate and wash fractions were pooled.

Fractionation

A saturated ammonium sulphate solution was added drop wise under stirring to the above pooled lysate. The volume of the SAS was adjusted to be one fifth of total volume, to obtain 20% of saturation. The solution was left standing overnight, and was centrifuged the next day at 14000 rpm, for 20 min. The pellet was washed with a small amount of 20% ammonium sulphate, and centrifuged again. The obtained supernatants were pooled, and SAS was added drop wise to obtain 40% of saturation. The solution was left standing overnight, and was centrifuged the next day at 14000 rpm, for 20 min. The obtained pellet was solubilised in NET buffer.

Chromatography

The capsid or VLP protein resolubilized in NET buffer was loaded on a Sepharose CL-4B column. Three peaks eluted during chromatography. The first one mainly contained membranes and membrane fragments, and was not collected. VLPs were contained in the second peak, while the third one contained other *E. coli* proteins.

The peak fractions were pooled, and the NaCl concentration was adjusted to a final concentration of 0.65 M. A volume of PEG solution corresponding to one half of the pooled peak fraction was added drop wise under stirring. The solution was left to stand overnight without stirring. The capsid protein was sedimented by centrifugation at 14000 rpm for 20 min. It was then solubilized in a minimal volume of NET and loaded again on the Sepharose CL-4B column. The peak fractions were pooled, and precipitated with ammonium sulphate at 60% of saturation (w/v). After centrifugation and resolubilization in NET buffer, capsid protein was loaded on a Sepharose CL-6B column for rechromatography.

Dialysis and Drying

The peak fractions obtained above were pooled and extensively dialysed against sterile water, and lyophilized for storage.

Example 2

Hydrolysis of RNA Encapsulated in Prior Art Qβ VLPs by RNAse A

Prior art Qβ VLPs at a concentration of 1.0 mg/ml in 0.2×HBS (4 mM HEPES, 30 mM NaCl, pH 7.4) were digested by addition of RNaseA (Qiagen AG, Switzerland) to a final concentration of 300 μg/ml. The sample was incubated for 3 h at 37° C. in a thermomixer at 650 rpm. Then the sample was dialyzed against 0.2 HBS buffer in a 300,000 molecular weight cutoff membrane overnight with one time exchange of buffer. An adequate portion of prior art Qβ VLPs from the same batch was not treated with RNaseA but rather saved for the determination of the amount of RNA, preferably nucleic acids, in the subsequent procedure.

To determine the amount of RNA, preferably nucleic acids, with secondary structure remained within the VLPs, equal amounts (by weight) of RNaseA-treated Qβ VLPs and prior art Qβ VLPs not being treated with RNaseA were loaded on a 1% agarose gel containing ethidium bromide (typically and preferably at a concentration of 0.5% g/ml), which intercalates into the secondary structures of RNA, preferably nucleic acids. The equal amount of loading of VLPs is realized by determining within the same experiment the protein concentrations of the prior art Qβ VLP not being treated with RNaseA and the RNaseA-treated Qβ VLP by Bradford assay following standard protocol given by the manufacture (BIO-RAD) using typically and preferably Albumin (PIERCE) as a standard. "Equal amount" as used herein, means that the amount of the RNase-treated VLP, preferably RNaseA-treated VLP, and even more preferably RNaseA-treated Qβ VLP, loaded on the gel does not differ from the amount of prior art VLP, preferably prior art Qβ VLP, loaded on the gel by more than 5%, preferably by more than 3%, and even more preferably by more than 1%. After electrophoresis for, typically and preferably, 1 h at, typically and preferably, 80V, the gel was exposed to UV-light, typically and preferably as described in Sambrook, J. et al., eds., Molecular Cloning, A Laboratory Manual, 2nd edition, Cold Spring Harbor Laboratory Press, Cold Spring Harbor, N.Y. (1989), and hereby in particular, as described in Chapter 6.15 and 6.19 thereof. The amount of RNA was indicated by the fluorescence intensity of the ethidium bromide intercalated in the RNA. Prior art Qβ VLPs not being treated with RNaseA showed strong fluorescence intensity while the intensity of the RNaseA-treated VLPs was strongly reduced. Quantification of the fluorescence intensity by densitometry (Kodak 1D Scientific Imaging System) showed that the amount of RNA, preferably nucleic acid, with secondary structure comprised by the RNaseA-treated VLPs is less than 10% (various experiments led to values of 3-9%) of the amount of RNA, preferably nucleic acids, with secondary structure comprised by the prior art Qβ VLPs not being treated with RNaseA (FIG. 1).

Assuming that the amount of host RNA comprised by the prior art Qβ VLP is 300 μg per mg of VLP as determined by the method described in EXAMPLE 17, the amount of RNA, preferably nucleic acid, with secondary structure remained within the RNaseA treated QβVLP is less than 30% g per mg of VLP (or corresponding to 9-27 μg per mg of VLP of the various experiments).

Example 3

Non-Enzymatic Hydrolysis of the RNA Content of VLPs

ZnSO$_4$ Dependent Degradation of the Nucleic Acid Content of a VLP:

Prior art Qβ VLPs (1.0 mg/ml in 0.2×HBS buffer) was incubated in the presence of 2.5 mM ZnSO$_4$ at 60° C. for 24 h. The resulting sample was dialyzed against 0.2 HBS buffer in a 300,000 molecular weight cutoff membrane overnight with one time of exchanging buffer. An adequate portion of prior art Qβ VLPs from the same batch was not treated with ZnSO$_4$ but rather saved for the determination of the amount of RNA, preferably nucleic acids, with secondary structure in the subsequent procedure.

To determine the amount of RNA, preferably nucleic acid, with secondary structures remained within the VLPs, equal amounts (by weight) of ZnSO$_4$-treated Qβ VLPs and prior art Qβ VLPs not being treated with ZnSO$_4$ were loaded on a 1% agarose gel containing ethidium bromide (typically and preferably at a concentration of 0.5 μg/ml), which intercalates into the secondary structures of RNA, preferably nucleic acids. The equal amount of loading of VLPs is realized by determining the protein concentrations of the prior art QβVLPs not being treated and the ZnSO$_4$-treated Qβ VLPs in the same experiment by Bradford assay following standard protocol given by the Bradford assay following standard protocol given by the manufacture (BIO-RAD) using typically and preferably Albumin (PIERCE) as a standard. "Equal amount" as used herein, means that the amount of the ZnSO$_4$-treated VLP, preferably ZnSO$_4$-treated Qβ VLP, loaded on the gel does not differ from the amount of prior art VLP, preferably prior art Qβ VLP, loaded on the gel by more than 5%, preferably by more than 3%, and even more preferably by more than 1%. After electrophoresis for, typically and preferably 1 h, at typically and preferably, 80V, the gel was exposed to UV-light, typically and preferably as described in Sambrook, J. et al., eds., Molecular Cloning, A Laboratory Manual, 2nd edition, Cold Spring Harbor Laboratory Press, Cold Spring Harbor, N.Y. (1989), and hereby in particular, as described in Chapter 6.15 and 6.19 thereof. The amount of RNA was indicated by the fluorescence intensity of the ethidium bromide intercalated into the RNA. Prior art Qβ VLPs not being treated showed a strong fluorescence intensity while the intensity of the ZnSO$_4$ treated VLPs was strongly reduced. Quantification of the fluorescence intensity by densitometry (Kodak 1D Scientific Imaging System) showed that the amount of RNA, preferably nucleic acids with secondary structures bound to the ZnSO$_4$ treated VLPs is 9% of the amount of RNA, preferably nucleic acids, with secondary structures bound to the prior art Qβ VLPs not being treated with ZnSO$_4$.

Assuming that the amount of host RNA comprised by the prior art Qβ VLP is 300 μg per mg of VLP as determined by the method described in EXAMPLE 17, the amount of RNA with secondary structure remained with the ZnSO$_4$ treated Qβ VLP is 27 μg per mg of VLP.

Example 4

Preparation of Qβ VLPs of the Invention by Disassembly/Reassembly in the Presence of Different Polyanionic Macromolecules Resulting in Reassembled Qβ VLPs (A) Disassembly of Prior Art Qβ VLP 45 mg prior art Qβ VLP (2.5 mg/ml, as determined by Bradford analysis) in PBS (20 mM Phosphate, 150 mM NaCl, pH 7.5) purified from E. coli lysate was reduced with 10 mM DTT for 15 min at room temperature under stirring conditions. Magnesium chloride was then added to 0.7 M final concentration and the incubation was continued for 15 min at room temperature under stirring conditions, which led to the precipitation of the encapsulated host cell RNA. The solution was centrifuged for 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

(B) Purification of the Qβ Coat Protein by Cation Exchange Chromatography and by Size Exclusion Chromatography The supernatant of the disassembly reaction, containing the dimeric coat protein, host cell proteins and residual host cell RNA, was diluted 1:15 in water to adjust conductivity below 10 mS/cm and was loaded onto a SP-Sepharose FF column (xk $^{16}/_{20}$, 6 ml, Amersham Bioscience). The column was equilibrated beforehand with 20 mM sodium phosphate buffer pH 7. The elution of the bound coat protein was accomplished by a step gradient to 20 mM sodium phosphate/500 mM sodium chloride and the protein was collected in a fraction volume of approx. 25 ml. The chromatography was carried out at room temperature with a flow rate of 5 ml/min and the absorbance was monitored at 260 nm and 2800 nm.

In the second step, the isolated Qβ coat protein (the eluted fraction from the cation exchange column) was loaded (in two runs) onto a Sephacryl S-100 HR column (xk$^{26}/_{60}$, 320 ml, Amersham Bioscience), equilibrated with 20 mM sodium phosphate/250 mM sodium chloride; pH 6.5. The chromatography was carried out at room temperature with a flow rate of 2.5 ml/min and the absorbance was monitored at 260 nm and 280 nm. Fractions of 5 ml were collected.

(C1) Reassembly of the Qβ VLP by Dialysis

Purified Qβ coat protein (2.2 mg/ml in 20 mM sodium phosphate pH 6.5), one polyanionic macromolecule (2 mg/ml in water), urea (7.2 M in water) and DTT (0.5 M in water) were mixed to the final concentrations of 1.4 mg/ml coat protein, 0.14 mg/ml of the respective polyanionic macromolecule, 1 M urea and 2.5 mM DTT. The mixtures (1 ml each) were dialyzed for 2 days at 5° C. in 20 mM Tris HCl, 150 mM NaCl pH 8, using membranes with 3.5 kDa cut off. The polyanionic macromolecules were: polygalacturonic acid (25000-50000, Fluka), dextran sulfate (MW 5000 and 10000, Sigma), poly-L-aspartic acid (MW 11000 and 33400, Sigma), poly-L-glutamic acid (MW 3000, 13600 and 84600, Sigma) and tRNAs from bakers yeast and wheat germ.

(C2) Reassembly of the Qβ VLP by Diafiltration 33 ml purified Qβ coat protein (1.5 mg/ml in 20 mM sodium phosphate pH 6.5, 250 mM NaCl) was mixed with water and urea (7.2 M in water), NaCl (5 M in water) and poly-L-glutamic acid (2 mg/ml in water, MW: 84600). The volume of the mixture was 50 ml and the final concentrations of the components were 1 mg/ml coat protein, 300 mM NaCl, 1.0 M urea and 0.2 mg/ml poly-L-glutamic acid. The mixture was then diafiltrated at room temperature, against 500 ml of 20 mM Tris HCl pH 8, 50 mM NaCl, applying a cross flow rate of 10 ml/min and a permeate flow rate of 2.5 ml/min, in a tangential flow filtration apparatus using a Pellicon XL membrane cartridge (Biomax 5K, Millipore).

Figure 2:
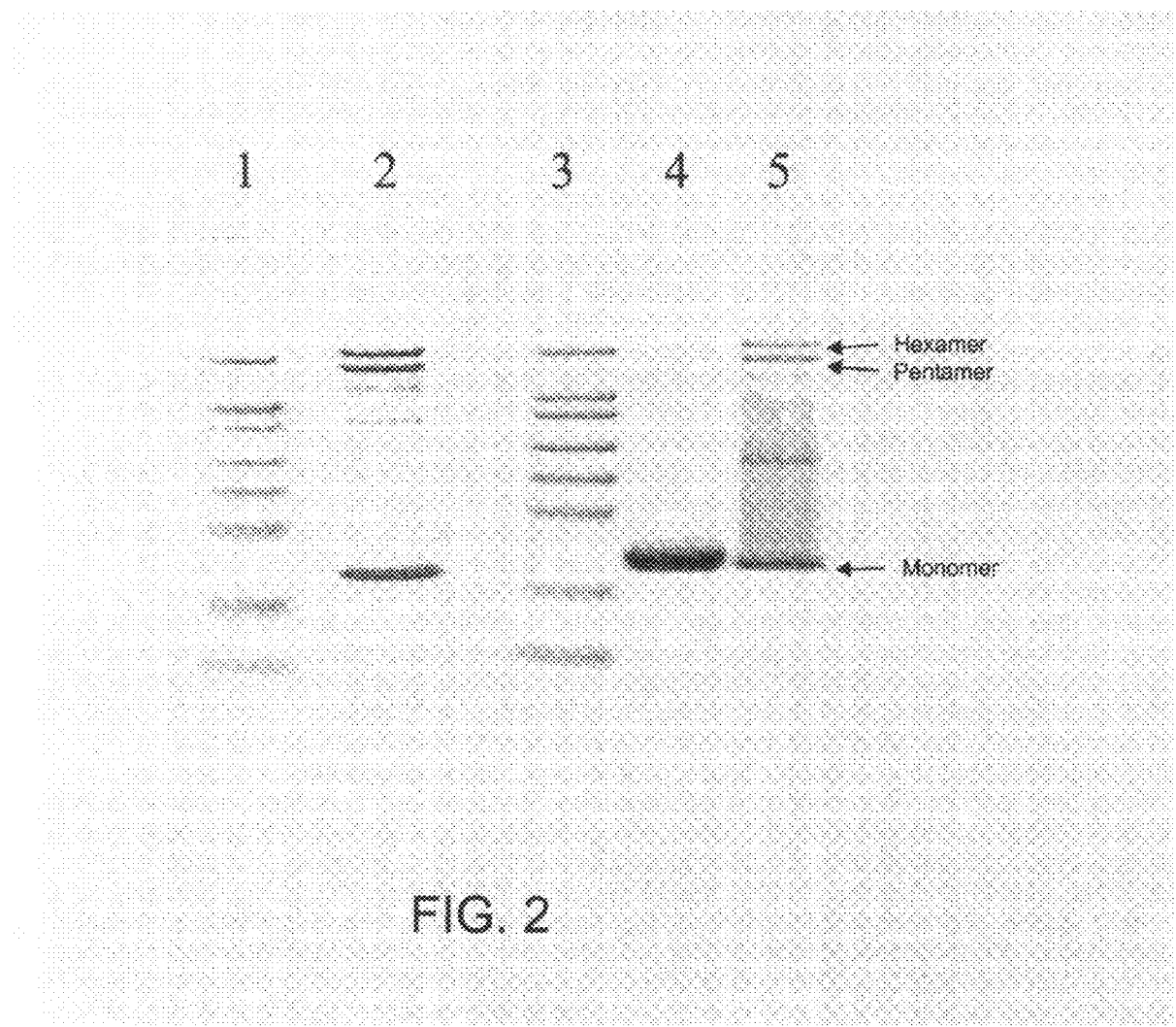
FIG. 2 shows a SDS-PAGE gel of a prior art Qβ VLP and a reassembled Qβ VLP in accordance with the present invention. Lane 1: molecular standard; Lane 2: prior art Qβ VLP under non-reducing condition; Lane 3: molecular standard; Lane 4: reassembled Qβ VLP run under reducing condition (25 mM DTT); Lane 5: reassembled Qβ VLP run under non-reducing condition.

Analysis of the Reassembled Qβ-VLPs (D1) Formation of Disulfide Bonds in the Qβ-VLPs The reassembled Qβ-VLPs in the presence of different polyanionic macromolecules as described in EXAMPLE 4(C1) and 4(C2) were analyzed by non-reducing SDS-PAGE and compared to the prior art Qβ VLP. The reassembled Qβ-VLPs exhibited bands of disulfide-linked pentameric and hexameric forms of the coat protein; similar to the prior art Qβ VLP, indicating the correct structural arrangement of the coat protein units in the reassembled QβVLP (FIG. 2).

(D2) Hydrodynamic Size of the Qβ VLPs Reassembled in the Presence of Different Polyanionic Macromolecules by Analytical Size Exclusion Chromatography Samples of the Qβ-VLPs reassembled in the presence of different polyanionic macromolecules as described in EXAMPLE 4(C1) and 4(C2) were analyzed by analytical size exclusion chromatography and compared to the prior art Qβ VLP. The reassembled Qβ VLP showed a peak migrating at the same retention time as the peak representing the prior art QβVLP, indicating the overall size and structure of the reassembled VLP is the same as the prior art VLP.

Example 5

In Vitro Assembly of AP205 VLPs (A) Purification of AP205 Coat Protein

Disassembly: 20 ml of AP205 VLP solution (1.6 mg/ml in PBS, purified from *E. coli* extract) was mixed with 0.2 ml of 0.5 M DTT and incubated for 30 min at room temperature. 5 ml of 5 M NaCl was added and the mixture was then incubated for 15 min at 60° C., causing precipitation of the DTT-reduced coat proteins. The turbid mixture was centrifuged (rotor Sorvall SS34, 10000 g, 10 min, 20° C.) and the supernatant was discarded and the pellet was dispersed in 20 ml of 1 M Urea/20 mM Na Citrate pH 3.2. After stirring for 30 min at room temperature, the dispersion was adjusted to pH 6.5 by addition of 1.5 M $Na_2HPO_4$ and then centrifuged (rotor Sorvall SS34, 10000 g, 10 min, 20° C.) to obtain supernatant containing dimeric coat protein.

Cation exchange chromatography: The supernatant (see above) was diluted with 20 ml water to adjust a conductivity of approx. 5 mS/cm. The resulting solution was loaded on a column of 6 ml SP Sepharose FF (Amersham Bioscience) which was previously equilibrated with 20 mM sodium phosphate pH 6.5 buffer. After loading, the column was washed with 48 ml of 20 mM sodium phosphate pH 6.5 buffer followed by elution of the bound coat protein by a linear gradient to 1 M NaCl over 20 column volumes. The fractions of the main peak were pooled and analyzed by SDS-PAGE and UV spectroscopy. According to SDS-PAGE, the isolated coat protein was essentially pure from other protein contaminations. According to the UV spectroscopy, the protein concentration was 0.6 mg/ml (total amount 12 mg), taking that 1 A280 unit reflects 1.01 mg/ml of AP205 coat protein. Furthermore, the value of A280 (0.5999) over the value of A260 (0.291) is 2, indicating that the preparation is essentially free of nucleic acids.

(B) Assembly of AP205 VLPs

Figure 5A:
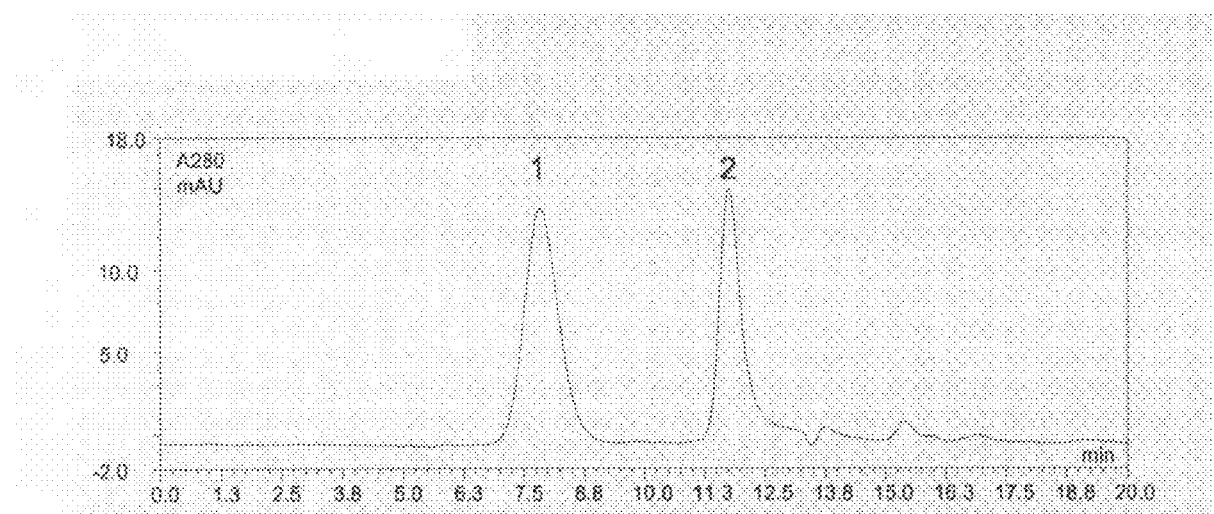
FIG. 5 shows the elution profile of an assembly mixture in size exclusion HPLC. (A) AP205 coat proteins assembled in the absence of any polyanionic macromolecule; (B) AP205 coat proteins assembled in the presence of polyglutamic acid. The formation of AP205 VLP is indicated by the presence of the peak at 7.83 min, the same retention time as the prior art AP205 VLP. The non-assembled AP205 coat protein was eluted out with retention time 11.77 min.

Assembly in the absence of any polyanionic macromolecule: The eluted protein fraction from above was diafiltrated and concentrated by TFF to a protein concentration of 1 mg/ml in 20 mM sodium phosphate pH 6.5. 500 μl of that solution was mixed with 50 μl of 5 M NaCl solution and incubated for 48 h at room temperature. The formation of reassembled VLPs in the mixture was shown by non-reducing SDS-PAGE and by size exclusion HPLC (FIG. 5A). A TSK-gel G5000 PWXL column (Tosoh Bioscience), equilibrated with 20 mM sodium phosphate, 150 mM NaCl pH 7.2, was used for the HPLC analysis.

Figure 5B:
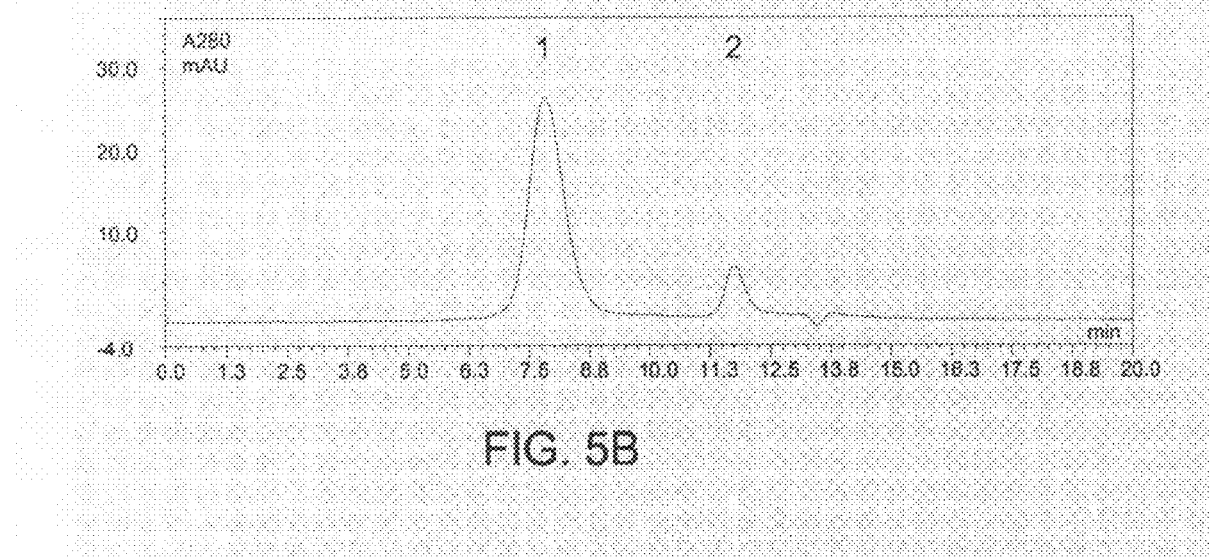

Assembly in the presence of polyglutamic acid: 375 μl of purified AP205 coat protein (1 mg/ml in 20 mM sodium phosphate pH 6.5) was mixed with 50 μl of NaCl stock solution (5 M in water) solution, 50 μl of polyglutamic acid stock solution (2 mg/ml in water, MW: 86400, Sigma) and 25 μl of water. The mixture was incubated for 48 h at room temperature. The formation of reassembled VLP in the mixture was shown by non-reducing SDS-PAGE and by size exclusion HPLC (FIG. 5B). The coat protein in the mixture was almost completely incorporated into the VLPs, showing a higher assembly efficiency than the AP205 coat protein assembled in the absence of any polyanionic macromolecule (FIG. 5A).

Example 6

Preparation of the Reassembled fr VLP or the Reassembled GA in the Presence of Polyanionic Macromolecules Similar experimental conditions as disclosed in Example 1 and 4 are applied to recombinantly produce prior art fr or GA VLP in E. coli, purify and disassemble these VLPs, and purify the obtained coat proteins of the corresponding RNA phages. Similar experimental conditions are then applied to reassemble the coat proteins into the reassembled fr VLP or the reassembled GA VLP.

Example 7

Coupling Nicotine Derivative to the Prior Art Qβ VLP and the Qβ VLPs of the Invention A nicotine derivative suitable for coupling to VLPs was synthesized according Langone et al. (1982, supra). Trans-4'-carboxycotinine is available from commercial sources. The methylester of trans-4'-carboxycotinine is produced by reacting trans-4'-carboxycotinine with methanolic sulfuric acid. The solution is neutralized with sodium bicarbonate, extracted with chloroform, concentrated on a rotary evaporator and recrystallized from ether-acetone. Reduction of the methyl ester with lithium aluminium hydride in ether then produces trans-3'-hydroxymethylnicotine. The O'-succinyl-hydroxymethylnicotine is then produced by the addition of succinic anhydride in benzene. The solution is concentrated on a rotary evaporator. Activation of the carboxyl group is subsequently achieved by addition of EDC (1-Ethyl-3-(3-dimethylaminopropyl)-carbodiimide) and N-hydroxysuccinimide (NHS) resulting in the N-hydroxysuccinimide ester of O'-succinyl-hydroxymethylnicotine (in the following abbreviated as "Suc-Nic").

Figure 3:
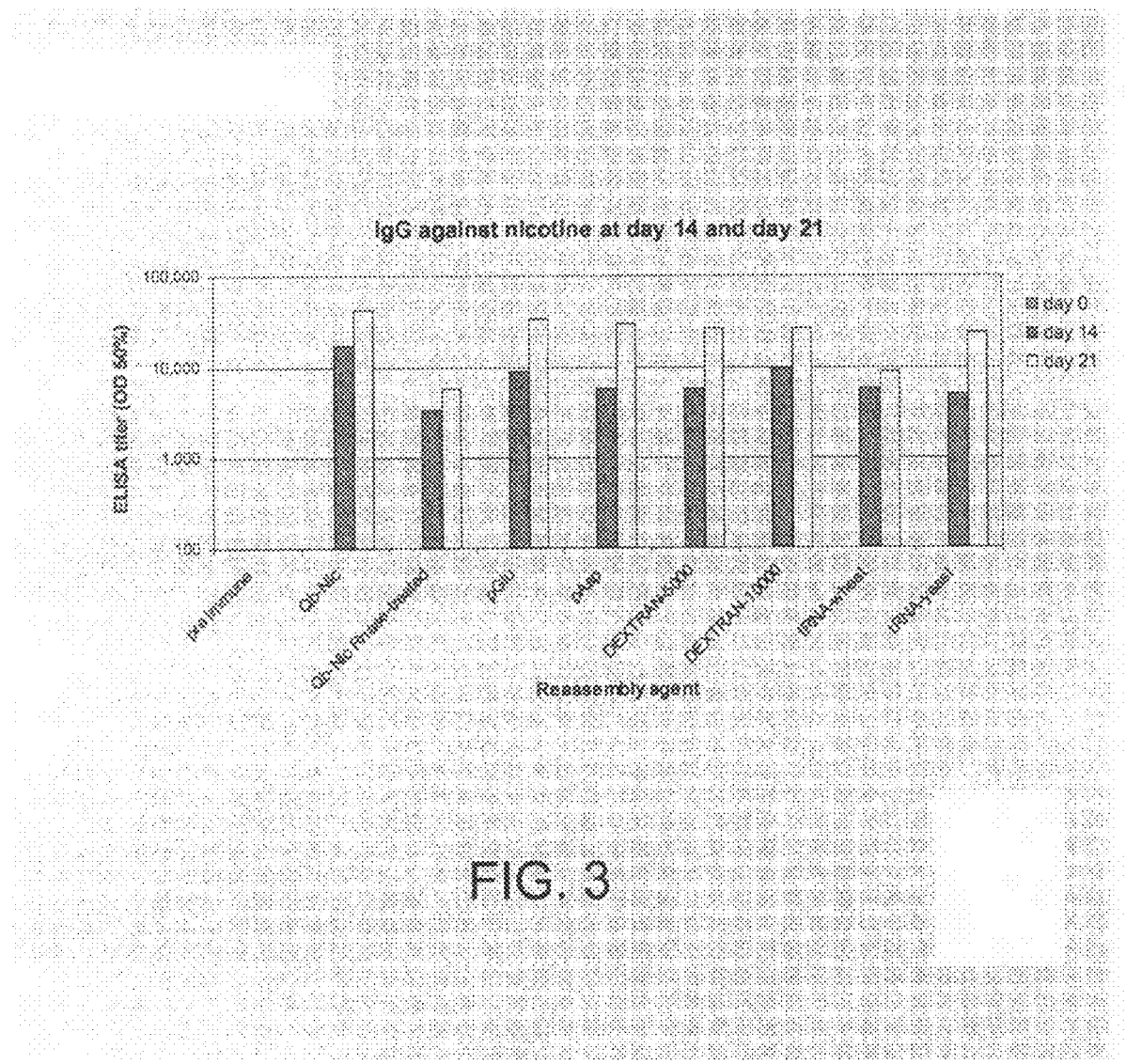
FIG. 3 shows antibody titer against nicotine after immunizing mice with a nicotine derivative coupled to the prior art Qβ VLP, RNase A treated Qβ VLP and the reassembled QβVLPs in the presence of different polyanionic macromolecules.

The prior art Qβ VLP and the Qβ VLPs of the invention, including the RNase A treated Qβ VLP, the reassembled Qβ VLPs in the presence of different polyanionic macromolecules as indicated in FIG. 3, were dialysed against Hepes-buffered saline HBS (50 mM Hepes, 150 mM NaCl, pH 8.0). The nicotine derivative Suc-Nic was dissolved in HBS at a concentration of 121 mM. It was added to different Qβ VLPs solutions (0.14 mM) at 1×, 5×, 50×, 100× and 500× molar excess and incubated at room temperature for 2 h on a shaker. The reaction solutions were then dialysed against HBS, pH 8.0 (cut off 10000 Da), flash-frozen in liquid nitrogen and stored at −80° C. The nicotine derivative suc-nic reacts with lysines on the surface of Qβ under formation of an amid bond. The resulting covalent conjugate was termed herein "prior art Qβ VLP-Nic" and "Qβ VLP of the invention-Nic", respectively.

Example 8

Qβ VLP of the Invention-Nic Induced Specific Antibody Response (A) Immunization of Mice 7-8 week old female Balb/c mice were vaccinated twice with 60 μg the prior art Qβ VLP-Nic and the Qβ VLP of the invention-Nic vaccines, respectively, wherein the Nicotine derivative is Suc-Nic. The vaccines were diluted in 200 ul of sterile PBS and injected subcutaneously into the left and right inguinal region. 14 days after the first immunization the mice were boosted. Sera were collected at day 14 (before boost) and day 21 (7 days after boost). The nicotine-specific antibody titers in serum were determined by ELISA.

(B) ELISA

Microtiter plates (Maxisorp, Nunc) were coated overnight with 5 μg/ml nicotine coupled to BSA (BSA-NicB01) in PBS (pH 7.3-7.7). After washing (0.05% Tween 20/PBS) and blocking with 2% BSA in PBS, sera were added at different dilutions in 2% BSA/1% FCS/PBS. For detection of IgE sera were depleted from IgG by incubating with protein G beads (Pharmacia). After 2 hours incubation at room temperature the plates were washed and HRP-labelled antibodies specific for mouse IgG (goat anti-mouse IgG (H+L), Jackson ImmunoResearch), IgG1 (rabbit anti-mouse IgG1, Zymed), IgG2a (rat anti-mouse IgG2a, Pharmingen) and IgE (goat anti-mouse IgE) were added. After 1 hour incubation the plates were washed and the color substrate OPD (Fluka) in citric acid buffer was added according the instructions of the manufacturer. After 5 minutes the color reaction was stopped with 5% $H_2SO_4$. Optical densities at 450 nm were read in an ELISA Reader (Benchmark, Biorad). ELISA titer was defined as the reciprocal dilution of the serum which gives a half-maximal optical density signal (OD 50%) in the ELISA.

All the Qβ VLP of the invention-Nic vaccines induced nicotine-specific antibodies to a level comparable to antibody titer induced by the prior art Qβ VLP-Nic vaccine. (FIG. 3). ELISA titers for serum pools of the three mice per group were measured for the total IgG response at day 14 and day 21. As shown in FIG. 3, at day 21 the IgG titers for the Qβ VLP-Nic of the invention vaccines were similar to the titer of the prior art Qβ VLP-Nic vaccine.

Figure 4:
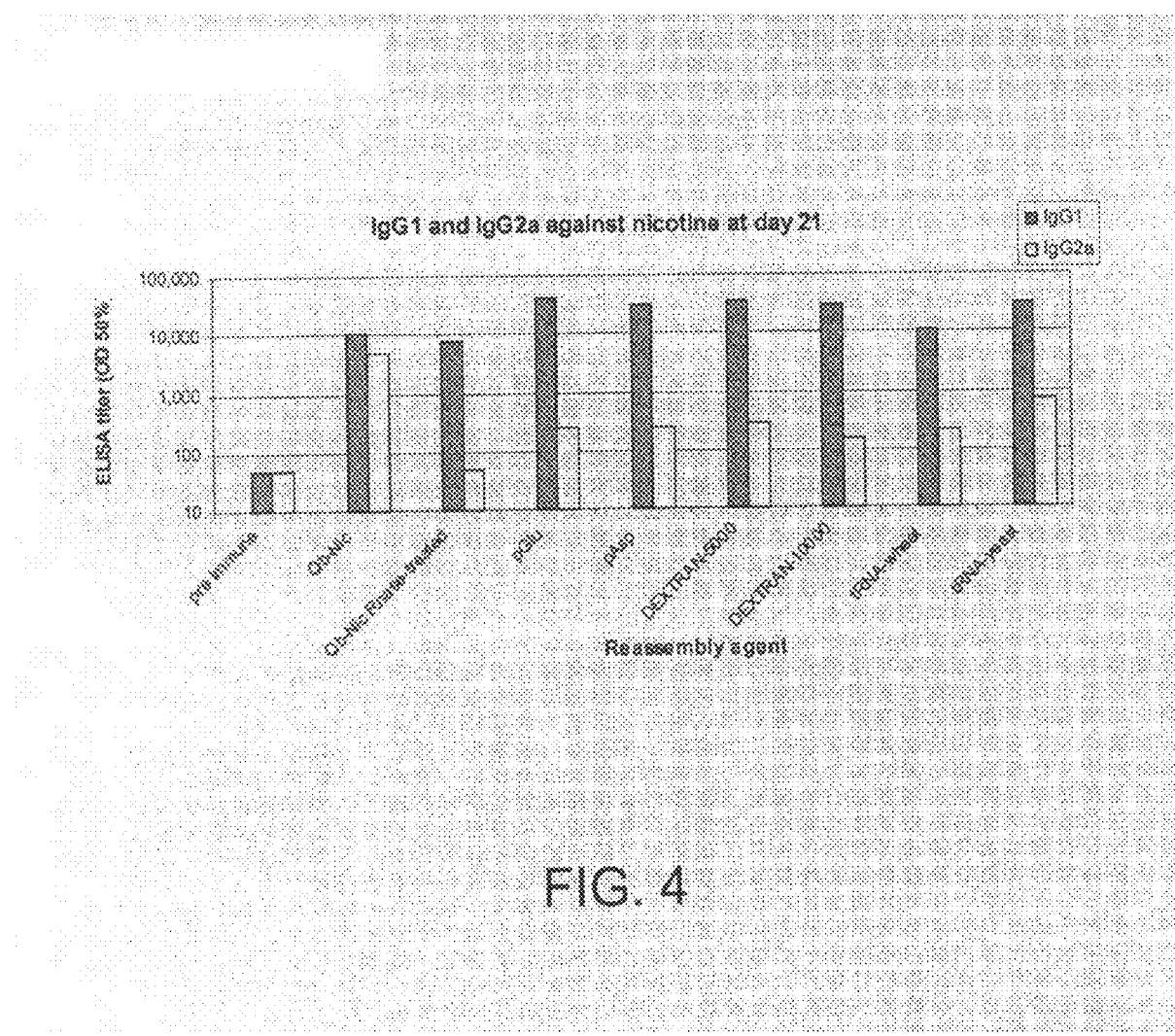
FIG. 4 shows IgG1 and IgG2a antibody titer against nicotine after immunizing mice with a nicotine derivative coupled to the prior art Qβ VLP, RNase A treated Qβ VLP and the reassembled Qβ VLPs in the presence of different polyanionic macromolecules.

FIG. 4 shows the anti-nicotine titers of the subclasses IgG1 and IgG2a at day 21 measured by ELISA. The prior art Qβ VLP-Nic induced a Th1 type of immune response with a high IgG2a titer. The ratio of IgG2a/IgG1 titers was about 0.5. The RNAse-treated Qβ VLP-Nic did not affect the IgG1 titer, but drastically reduced the IgG2a titer, resulting in a ratio of 0.006, and the overall antibody titer was reduced compared to the prior art VLP. The reassembled QβVLP-Nic vaccines induced higher IgG1 titers but lower IgG2a titers, compared to the prior art Qβ VLP-Nic. This is reflected by the IgG2a/IgG1 titer ratios lower than 0.035, indicating a more Th2 type response. However, despite of more TH2 response, no IgE could be detected in the sera vaccinated with the reassembled Qβ VLP-Nic. Similarly, no IgE could be detected in the sera vaccinated with the prior art Qβ VLP-Nic.

The data show that the reassembled Qβ VLP-Nic maintained high immunogenicity while the immune responses have been shifted into a more Th2 type response without inducing the production of IgE.

Example 9

Coupling of GnRH Peptides to the Reassembled Qβ VLP

The following peptide analogues comprising amino acid 1-10 of GnRH (SEQ ID NO:1), extended with either a cysteine as attachment site for coupling or with two glycine residues plus a cysteine residue as attachment site, were chemically synthesized:

```
CGG-GnRH    CGGEHWSYGLRPG-NH2    (SEQ ID NO: 2)
GnRH-GGC    pEHWSYGLRPGGGC       (SEQ ID NO: 3)
C-GnRH      CEHWSYGLRPG-NH2      (SEQ ID NO: 4)
GnRH-C      pEHWSYGLRPGC         (SEQ ID NO: 5)
```

Peptides are coupled to reassembled Qβ VLP as described below.

High coupling efficiency (>90% of monomers carrying at least 1 peptide) for CGG-GnRH (SEQ ID NO:2) are achievable by derivatizing recombinantly produced reassembled QβVLPs (2 mg/ml) in 50 mM NaCl, 20 mM Hepes pH7.2 with a 20 fold molar excess of SMPH (100 mM in DMSO, Pierce) for 0.5 h at 25° C. The reaction is subsequently dialysed for 2×2 h against 20 mM Hepes pH7.2 at 4° C., using 10.000 MWCO dialysis tubing, to remove unreacted SMPH. GnRH peptide (5 mM in DMSO) is added in a 7 fold molar excess and allowed to react for 2 h in a thermomixer at 25° C. Reactions are dialysed overnight against 20 mM Hepes pH7.2 to remove uncoupled peptide.

Intermediate coupling efficiencies (82% of monomers carrying at least 1 peptide) for peptides CGG-GnRH (SEQ ID NO:2) and GnRH-GGC (SEQ ID NO:3) are achievable by derivatizing reassembled Qβ VLPs (1 mg/ml) in 20 mM Hepes pH7.2 with an 18 fold molar excess of SMPH for 0.5 h at 25° C. Reactions are subsequently dialysed against 20 mM Hepes pH7.2 and coupled with a 10 fold molar excess GnRH peptide (10 mM in DMSO) by incubation on a thermoshaker for 2 h at 25° C.

Coupling of peptides C-GnRH (SEQ ID NO:4) and GnRH-C (SEQ ID NO:5) is performed by derivatizing reassembled Qβ VLPs (2.8 mg/ml) in 20 mM Hepes pH7.2 with a 20 fold molar excess SMPH (50 mM in DMSO) for 0.5 h at 25° C. followed by overnight dialysis against 20 mM Hepes pH7.2. High (>90%) and low (60-71%) coupling efficiencies are obtainable by subsequent incubation on a thermoshaker for 2 h at 25° C. with 7 fold and 2.5 fold molar excess of peptide (5 mM in DMSO), respectively. Reactions are dialysed against 20 mM Hepes pH7.2 overnight to remove uncoupled peptide. The Qβ-GnRH coupling products are centrifuged and supernatants are analysed on SDS-PAGE gel under reducing conditions. Qβ-GnRH coupling products were named Qβ-CGG-GnRH, GnRH-GGC-Qβ, Qβ-C-GnRH and GnRH-C-Qβ according to the respective peptides (SEQ ID NO:2, 3, 4 and 5) that were used for coupling.

Example 10

Coupling Human IL-23 p19 to the VLPs of the Invention

The reassembled Qβ virus-like particle (2 g/l), AP205 (2 g/l), fr (2 g/l) and GA (2 g/l), the RNase A treated Qβ virus-like particle (2 g/l), AP205 (2 g/l), fr (2 g/l) and GA (2 g/l), the ZnSO$_4$ treated Qβ virus-like particle (2 g/l), AP205 (2 g/l), fr (2 g/l) and GA (2 g/l), are derivatised with 0.714 mM SMPH (Pierce, Perbio Science) for 30 minutes at 25° C. and then dialysed against 20 mM Hepes pH8, 150 mM NaCl. Human IL-23 p19 protein (SEQ ID NO:7, 0.28 g/l) protein and derivatised Qβ particles (0.5 g/l) are incubated for two hours at 25° C. in the presence of 1 mM EDTA and 10 μM, 30 μM or 90 μM TCEP (Pierce, Perbio Science). The coupling products are analysed by SDS-page. The antigen density of the vaccine is determined by densitometric analysis.

Example 11

Fusion of an Aβ1-6 Peptide to the C-Terminus of the Qβ A1 Protein Truncated at Position 19 of the CP Extension A primer annealing to the 5' end of the Qβ A1 gene and a primer annealing to the 3' end of the A1 gene and comprising additionally a sequence element coding for the Aβ1-6 peptide, of sequence DAEFRH (SEQ ID NO: 87) or DAEFGH (SEQ ID NO: 123), are used in a PCR reaction with pQβ1O as template. The PCR product is cloned in pQβ1O (Kozlovska T. M. et al, Gene 137: 133-37 (1993)), and the VLP comprising fusion protein is expressed and purified in similar condition as described in Example 1.

The purified Qβ VLP-AP1-6 is to be disassembled as described in Example 4. Purified. Qβ-Aβ1-6 fusion protein (2.2 mg/ml in 20 mM sodium phosphate pH 6.5), one polyanionic macromolecule (2 mg/ml in water), urea (7.2 M in water) and DTT (0.5 M in water) are mixed to the final concentrations of 1.4 mg/ml fusion protein, 0.14 mg/ml of the respective polyanionic macromolecule, 1 M urea and 2.5 mM DTT. The mixtures (1 ml each) are dialyzed for 2 days at 5° C. in 20 mM Tris HCl, 150 mM NaCl pH 8, using membranes with 3.5 kDa cut off. The polyanionic macromolecules are: polygalacturonic acid (25000-50000, Fluka), poly-L-glutamic acid (MW 3000, 13600 and 84600, Sigma) or tRNAs from bakers yeast or wheat germ.

Example 12

Insertion of an AP 1-6 Peptide Between Positions 2 and 3 of fr Coat Protein

Complementary primers coding for the sequence of the Aβ1-6 peptide of sequence DAEFRH (SEQ ID NO: 87) or DAEFGH (SEQ ID NO: 123), and containing Bsp1191 compatible ends and additional nucleotides enabling in frame insertion, are inserted in the Bsp1 191 site of the pFrd8 vector (Pushko, P. et al., Prot. Eng. 6: 883-91 (1993)) by standard molecular biology techniques. Alternatively, the overhangs of the pFrd8 vector are filled in with Klenow after digestion with Bsp1 191, and oligonucleotides coding for the sequence of the Aβ1-6 peptide and additional nucleotides for in frame cloning are ligated in pFrd8 after the Klenow treatment. Clones with the insert in the right orientation are analysed by sequencing. Expression and purification of the chimeric fusion protein in *E. coli* JM 109 or *E. coli* K802 is performed as described in Pushko, P. et al, Prot. Eng. 6:883-91 (1993), but for the chromatography steps which are performed using a Sepharose CL-4B or Sephacryl S-400 (Pharmacia) column. The cell lysate is precipitated with ammonium sulphate, and purified by two successive gel filtration purification steps, similarly to the procedure described for Qβ in Example 1.

The purified chimeric fr VLP-AP 1-6 is to be disassembled as described in Example 4. Purified fr AP 1-6 fusion protein (2.2 mg/ml in 20 mM sodium phosphate pH 6.5), one polyanionic macromolecule (2 mg/ml in water), urea (7.2 M in water) and DTT (0.5 M in water) are mixed to the final concentrations of 1.4 mg/mil fusion protein, 0.14 mg/ml of the respective polyanionic macromolecule, 1 M urea and 2.5 mM DTT. The mixtures (1 ml each) are dialyzed for 2 days at 5° C. in 20 mM Tris HCl, 150 mM NaCl pH 8, using membranes with 3.5 kDa cut off. The polyanionic macromolecules are: polygalacturonic acid (25000-50000, Fluka), dextran sulfate (MW 5000 and 10000, Sigma), poly-L-aspartic acid (MW 11000 and 33400, Sigma).

Example 13

Coupling of Peptides Derived from Angiotensin I and Angiotensin II to the Reassembled AP205 VLP and GA VLP and the Immunization of Mice with the Resulting Conjugates A. Production of Conjugates The following angiotensin peptides moieties were chemically synthesized:

CGGDRVYIHPF ("Angio 1"; SEQ ID NO:111), CGGDRVYIHPFHL ("Angio 2"; SEQ ID NO:112), DRVYIHPFHLGGC ("Angio 3"; SEQ ID NO:113), CDRVYIHPFHL ("Angio 4"; SEQ ID NO:114), CHPFHL ("Angio 5"; SEQ ID NO:115), CGPFHL ("Angio 6"; SEQ ID NO:116), CYIHPF ("Angio 7"; SEQ ID NO:117), CGIHPF ("Angio 8"; SEQ ID NO:118), CGGHPF ("Angio 9"; SEQ ID NO:119), DRVYIGGC ("Angio 13"; SEQ ID NO:120), DRVYGGC ("Angio 14"; SEQ ID NO:121) and DRVGGC ("Angio 15"; SEQ ID NO: 122). They are used for chemical coupling to the reassembled AP205 or GA VLP as described in the following.

For peptides Angio 1 to Angio 4: A solution of 5 ml of the reassembled 2 mg/ml AP205 or GA VLP in 20 mM Hepes. 150 mM NaCl pH 7.4 is reacted for 30 minutes with 507 µl of a solution of 13 mg/ml Sulfo-MBS (Pierce) in $H_2O$ at 25° C. on a rocking shaker. The reaction solution is subsequently dialyzed twice for 2 hours against 2 L of 20 mM Hepes, 150 mM NaCl, pH 7.4 at 4° C. 665 µl of the dialyzed reaction mixture is then reacted with 2.8 µl of each of the corresponding 100 mM peptide stock solution (in DMSO) for two hours at 25° C. on a rocking shaker. The reaction mixture is subsequently dialyzed 2×2 hours against 2 liters of 20 mM Hepes, 150 mM NaCl, pH 7.4 at 4° C.

For peptides Angio 5-9 and Angio 13-15: A solution of 3 ml of the reassembled 2 mg/ml AP205 or GA VLP in 20 mM Hepes. 150 mM NaCl pH 7.2 is reacted for 50 minutes with 86 µl of a solution of 100 mM SMPH (succinimidyl-6-(β-maleimidopropionoamido hexanoate, Pierce) in DMSO at 25° C. on a rocking shaker. The reaction solution is subsequently dialyzed twice for 2 hours against 2 L of 20 mM Hepes, 150 mM NaCl, pH 7.2 at 4° C. 514 µl of the dialyzed reaction mixture is then reacted with 3.6 µl of each of the corresponding 100 mM peptide stock solution (in DMSO) for 4 hours at 25° C. on a rocking shaker. The reaction mixture is subsequently dialyzed 2×2 hours against 2 liters of 20 mM Hepes, 150 mM NaCl, pH 7.2 at 4° C.

B. Immunization

Female Balb/c mice are vaccinated with one of the nine angiotensin peptide derivatives coupled to the reassembled AP205 or GA VLP without the addition of adjuvants. 50 µg (Angio 1-4 vaccine) or 20 µg (Angio 5-9 vaccine) of total protein of each sample is diluted in PBS to 2001 and injected subcutaneously (1001 on two ventral sides) on day 0 and day 14. Mice are bled retroorbitally on day 21 and their serum is analyzed using an angiotensin-specific ELISA.

It should be noted that the human and the murine sequences of the angiotensin peptides identically correspond to each other. Therefore, immunization of a human or a mouse with vaccines or conjugates, respectively, comprising angiotensin peptide moieties as antigenic determinant in accordance with the invention, is a vaccination against a self-antigen.

Example 14

Qβ VLP Reassembled in the Presence of Polyglutamic Acid led to the Abrogation of a CD8+ T Cell Response C57BL/6 mice were immunized by injecting subcutaneously 150 ug of Q.beta. VLPs chemically liked to the LCMV-peptide gp33 (KAVYNFATM) (Q.beta.x33, SEQ ID NO:124). One group of mice received intact Q.beta. VLP.times.33 particle, whereas the other groups were treated with Q.beta. VLP.times.33 that were reassembled in the presence of different amount of poly-L-glutamic acid (Q.beta./poly L-Glu/.times.33 with 0.1 mg/ml, 0.2 mg/ml and 0.4 mg/ml of poly-L-glutamic acid). Eight days later blood from immunized animals was analysed for the expansion of gp33-specific CD8+ T cells. Blood was collected in FACS buffer (PBS, 2% FCS, 5 mM EDTA, pH 8.2) and stained for 10 min at 37.degree. C. with PE-labeled H2-Db-tetramer loaded with the gp33-peptid (Proimmune, Oxford, UK) followed by staining for 30 min at 4.degree. C. with an APC labelled rat anti-mouse CD8a-antibody (BD PharMingen, San Jose, USA). After washing, erythrocytes were lysed with BD-Lyzing Solution (BD Biosciences, San Jose, USA) for 10 min at room temperature. Finally, the cells were analysed on a FACS Calibur using CellQuest software. First of all, the cells were acquired in the forward scatter and side scatter and the lymphocytes were gated. From this lymphocyte population, the gp33-PE labelled and CD8-APC labelled cells were measured with the FL2 and FI4 detector, respectively. The amount of gp33-specific T cells were calculated as percent CD8 positive, gp33 positive cells on total CD8 positive lymphocytes.

Flow cytometry analysis showed that none of the Qβ/poly L-Glu/x33 samples induced an expansion of gp33-specific CD8 positive T cells compared to animals receiving the prior art Qβ VLPx33. (see TABLE 1).

After the measurement of the gp33-specific T cell response the mice were challenged with $1.5 \times 10^6$ pfu of a recombinant vaccinia virus that express the gp33-peptide. 5 days later the viral titer was measured in the ovaries of these mice. A single cell suspension of the ovaries was incubated in serial dilutions on BSC40 cells. After overnight incubation at 37° C. at 5% $CO_2$ cells were stained with crystal violet (500 ml 96% Ethanol, 5 g Crystal violet (Sigma C-3886), 8 g NaCl, 450 ml $H_2O$, 50 ml Formaldehyde) in order to visualize plaques in the cell layer derived from virus induced cell lysis. The number of residual virus in the ovaries was calculated as plaque forming units (pfu). The plaque forming units were significant higher in mice received the reassembled Qβ VLPx33 vaccines compared with the group of mice received the prior art Qβ VLPx 33 (see TABLE 1).

TABLE 1

| | $CD8^+$, $gp33^+/CD8^+$ | Plaque Forming Units |
|---|---|---|
| naïve mice | 0.18% +/− 0.04% | $5 \times 10^7$ pfu |
| Prior art Qβ VLPx33 | 1.43% +/− 0.49% | $2.5 \times 10^5$ pfu |
| Qβ/poly L-Glu (0.1 mg/ml)x33 | 0.2% +/− 0.05% | $1.4 \times 10^8$ pfu |
| Qβ/poly L-Glu (0.2 mg/ml)/x33 | 0.11% +/− 0.07% | $2.3 \times 10^7$ pfu |
| Qβ/poly L-Glu (0.4 mg/ml)/x33 | 0.22% +/− 0.07% | $2 \times 10^7$ pfu |

Example 15

RNase A Digested Qβ VLP Coupled to Mouse TNF and its Induced Immune Responses A Coupling of Mouse TNF Protein to Prior Art Qβ VLP fusion protein (SEQ ID NO:67) consisting of cysteine containing linker, a hexahistidine tag and the mature murine TNF protein (corresponding to amino acids 78 to 233 of the immature protein) was recombinantly expressed in *Escherichia coli* and purified to homogeneity by affinity chromatography. A solution containing 1.4 mg/ml of this protein in 20 mM HEPES, 150 mM NaCl, pH 7.2 was incubated for 60 min at room temperature with an equimolar amount of TCEP.

A solution of 500 µl of 3.06 mg/ml prior art Qβ VLP in 20 mM HEPES, 150 mM NaCl pH 7.2 was then reacted for 60 minutes at room temperature with 4.2 µl of a SMPH solution (65 mM in DMSO). The reaction solution was dialysed at 4° C. against two 3 l changes of 20 mM HEPES pH 7.2 for 2 hours and 14 hours, respectively. 60 µl of the derivatized and dialyzed Qβ solution was mixed with 30 µl $H_2O$ and 180 µl of the purified and pre-reduced mouse TNF protein and incubated for 4 hours at 15° C. for chemical crosslinking. Uncoupled protein was removed by 2×2 h dialysis at 4° C. against PBS using cellulose ester membranes with a molecular weight cutoff of 300.000 Da.

B. RNase Digestion of Qβ-mTNF.

300 µl of the prior art Qβ coupled to murine TNFα (Qβ-mTNF, 0.7 mg/ml) obtained from A1 were incubated with 3 µl of RNase A (100 mg/ml) at 37° C. for 3 hours with gentle agitation. The degree of digestion of the RNA contained in the prior art Qβ was checked by agarose gel electrophoresis of an aliquot of the reaction and subsequent ethidium bromide staining. About 95% of *E. coli* host RNA was digested after such a treatment. The RNase-treated Qβ-mTNF was dialysed overnight against an excess of 20 mM HEPES pH 7.2.

C. Immunization of Mice.

Three female balb/c mice were immunised with prior art Qβ-mTNF and five female balb/c mice were immunized with RNase-treated Qβ-mTNF. 25 µg of total protein were diluted in PBS to 200 µl and injected subcutaneously (100 µl on two ventral sides) on day 0 and day 14. Mice were bled retroorbitally on day 0 and day 21, and murine TNF-specific antibody titers in serum were determined by ELISA.

D. ELISA

Microtiter plates (Maxisorp, Nunc) were coated overnight with 1 µg/ml recombinant murine TNFα. The determination of total IgG titers and the titer of different subclasses (IgG1, IgG2a) specific for prior art or reassembled Qβ VLP, and to TNFα in sera were determined by ELISA substantially the same as described in EXAMPLE 8

TABLE 2 shows that both the prior art Qβ-mTNF and the RNase-treated Qβ-mTNF induced antibodies specific for murine TNFα. The prior art Qβ-mTNF induced a Th1 type of immune response with a high IgG2a titer. The average ratio of IgG2a/IgG1 titers was about 0.75. RNAse-treatment of Qβ-mTNF did not influence the IgG1 titer, but drastically reduced the IgG2a titer, resulting in a ratio of 0.135. These data show that the immune responses induced by the RNase-treated Qβ-mTNF have shifted from a more Th1 immune response to a more Th2 response, as compared with the immune response induced by the prior art Qβ-mTNF.

TABLE 2

|  | Total IgG | IgG2a | IgG1 | IgG2a/IgG1 |
|---|---|---|---|---|
| prior art Qβ-mTNF | 27768 ± 16318 | 1465 ± 1107 | 1832 ± 885 | 0.75 |
| RNAse-treated Qβ-mTNF | 18681 ± 9510 | 279 ± 164 | 1950 ± 937 | 0.135 |

Example 16

Coupling of Murine TNFα (4-23) Peptide to the Prior Art Qβ VLP and to the Reassembled Qβ and AP205 VLP A solution of 3 ml of 3.06 mg/ml intact Qβ VLP in 20 mM HEPES, 150 mM NaCl pH 7.2 was reacted for 60 minutes at room temperature with 99.2 µl of a SMPH solution (65 mM in DMSO). The reaction solution was dialysed at 4° C. against two changes of 20 mM HEPES, 150 mM NaCl pH 7.2 for 4 hours and 14 hours, respectively. 69 µl of the derivatized and dialyzed Qβ solution was mixed with 265.5 µl 20 mM HEPES pH 7.2 and 7.5 µl of mTNFα (4-23) peptide with second attachment site CGG fused to the N terminus (23.6 mg/ml in DMSO) and incubated for 2 hours at 15° C. for chemical crosslinking. Uncoupled peptide was removed by 2×2 h dialysis at 4° C. against PBS. Coupled products were analysed on a 12% SDS-polyacrylamide gel under reducing conditions.

Similar conditions are applied to couple murine TNFα (4-23) to the reassembled Qβ and AP205 VLPs, respectively.

Example 17

Determination of the Amount of RNA Enclosed in the VLPs

VLP samples (see TABLE 2, 1 mg/ml) were incubated in 10 mM $MgCl_2$ and 0.1 M $NaHCO_3$ pH 9.7 for approx. 16 h at 60° C. This is to hydrolyze the encapsulated RNA, preferably nucleic acids, to nucleotides and to precipitate the proteins. The samples were centrifuged at 14000 rpm for 5 min using a rotor F45-30-11 (Eppendorf)) to separate the protein precipitated from the soluble nucleotides.

The pH of the supernatants was adjusted to pH 7 by adding 0.5 M sodium phosphate buffer pH 7. The nucleotide concentrations in each sample were further adjusted by a series dilution to allow the recording of UV data in an absorption range below 2 AU (AU refers to "absorption units"). The same buffer but without the presence of VLP was used as reference.

The nucleotide concentration corresponding to the amount of original RNA, preferably nucleic acids, is calculated from the absorption value at 260 nm taking into account that 1 AU corresponds to 33 µg RNA/ml. The RNA concentration of the samples is summarized in TABLE 3.

TABLE 3

|  | Samples | Average RNA concentration µg RNA per mg VLP or µg RNA per mg protein in sample 3 |
|---|---|---|
| 1 | Prior art Qβ VLP | 316 |
| 2 | Reassembled Qβ VLP in pGlu | 2 |
| 3 | Purified Qβ coat protein | 0.3 |

Example 18

Coupling of Maleimido-GnRH to the Prior Art Qβ VLP and the Reassembled Qβ VLP (A) Preparation of Maleimido-GnRH Peptide GnRH is chemically synthesized according standard methods. MBS (m-Maleimidobenzoyl-N-hydroxysulfosuccinimide ester) or SMPH (Succinimidyl-6-[β-maleimidopropionamido]hexanoate) is covalently attached to the amino group at the N-terminus of the peptide.

(B) Transformation of the Amino Groups of Qβ VLPs to Sulfhydryl Groups

The prior art Qβ VLP and the reassembled Qβ VLP (stock solution in PBS) are mixed with 0.1 M sodium phosphate pH 7 and 2-Iminothiolane (200 mM stock solution in DMSO) to final concentrations of 2 mg/ml Qβ VLP, 50 mM sodium phosphate pH 7 and 15 mM 2-Iminothiolane. The mixture is incubated for 2 h at room temperature and subsequently the excess of non-reacted 2-Iminothiolane is removed by gel filtration (Sephadex G25 in PBS), resulting in purified, SH-modified Qβ VLP solution at a concentration of approx 1.4 mg/ml.

(C) Coupling of Maleimido-GnRH

The SH-modified prior art Qβ VLP and the SH-modified reassembled Qβ VLP (1.4 mg/ml) obtained from step (B) are mixed with ½₀ volume of maleimido-GnRH stock solution (10 mM in DMSO) and incubated for 1 h at room temperature. Uncoupled maleimido-GnRH is removed by diafiltration using a 300 kDa membrane. The coupling results are checked by SDS-PAGE gel.

Example 19

Pyrogens Test

This test is preformed according to standard pyrogens test procedure as described in European Pharmacopoeia 4th edition, Chapter 2.6.8., page 131-132, which is herein incorporated by way f reference.

The test samples are Qβ VLP reassembled in the presence of polyglutamic acid, the Qβ VLP treated with RNase, the Qβ VLP treated with $ZnSO_4$ and the prior art Qβ which comprises RNA of E. coli. The concentrations of the Qβ VLPs are 0.3 mg/ml. The samples are prewarmed to 38.5° C. before injection.

The animals used in this test are healthy adult rabbit with approximately 3 kg body weight. Three rabbits are tested in each group.

Briefly, the samples in the amount of 0.3 ml/kg of body weight are slowly injected into the marginal vein of the ear of each rabbit over a period not exceeding 4 minutes. The initial temperature of each rabbit is the mean of two temperature readings recorded for that rabbit at an interval of 30 min in the 40 min immediately preceding the injection of the sample. The maximum temperature of each rabbit is the highest temperature recorded for that rabbit in the 3 h after the injection. Record the temperature of each rabbit at intervals of not more than 30 min, beginning at least 90 min before the injection of the sample and continuing 3 h after the injection. The difference between the maximum temperature and the initial temperature of each rabbit is taken to be its response. The capability of the tested VLPs to induce fever in rabbit is studied and compared with the prior art VLP.

Example 20

Coupling IL-5 to the Reassembled Qβ VLP and Determination of its Induced Immune Responses

Example 21

Coupling IL-5 to the Prior Art Qβ VLP and to the Qβ VLP Reassembled in the Presence of Poly-L-Glutamic Acid and Determination of its Induced Immune Responses Mouse IL-5 (SEQ ID NO:46) or human IL-5 (SEQ ID NO:47) fused to the N-terminal gamma 3 amino acid linker (SEQ ID NO:48) was recombinantly produced in E. coli and purified. Prior art Qβ VLP and the Qβ VLP reassembled in the presence of poly-L-glutamic acid were derivatized with a 10× fold molar excess of SMPH for 30 min at 25° C. Derivatization reactions were dialysed for 2×2 hrs against a 1000× volume of dialysis buffer consisting of 20 mM Hepes, 150 mM NaCl; pH 7.4 in Slide-A-Lyzer dialysis cassettes with a MWCO of 10'000. Purified mouse IL-5 was prereduced for 60 min with an 2× fold molar excess of pH-neutralized TCEP. Reduced mouse IL-5 (42 μM) was incubated for 3 hours at 20° C. with 40 μM SMPH-derivatized prior art Qβ VLP prepared according to EXAMPLE 1 and 42 μM mouse IL-5, respectively, was incubated for 3 hours at 20° C. with 40 μM SMPH-derivatized Qβ VLP reassembled in the presence of poly-L-glutamic acid prepared according to EXAMPLE 4. The coupling-reactions were dialysed 12 hrs and again 6 hrs against PBS pH 8.0 using a 300 kDa cut-off dialysis membrane.

Five female BalbC mice per group were injected subcutaneously a day 0, day 14 and day 28 with 50 μg, 25 μg and again 50 μg of either "prior art-Qβ-mouse IL-5" or "reassembled Qβ-mouse IL-5" vaccine in 200 μl of PBS (100 μl on two ventral sides). As controls, five mice were immunized at day 0, day 14 and day 28 with either prior art Qβ VLP or Qβ VLP reassembled in the presence of poly-L-glutamic, only. Vaccines were administered without adjuvant. Mice were bled at day 0, 14, 21 and 28 of the immunization protocol.

Microtiter plates (Maxisorp, Nunc) were coated overnight with 2 μg/ml recombinant murine IL-5 or 2 μg/ml prior art Qβ or 2 μg/ml Qβ reassembled in the presence of poly-L-glutamic acid. The determination of total IgG titers and the titer of different subclasses (IgG1, IgG2a) specific for prior art or reassembled Qβ VLP, and to IL-5 in sera were determined by ELISA substantially the same as described in EXAMPLE 8.

TABLE 4

| vaccine | time | Total IgG | IgG2a | IgG1 | IgG2a/IgG1 |
| --- | --- | --- | --- | --- | --- |
| prior art | day 14 | 8964 | 2018 | 807 | 2.5 |
| Qβ-mIL-5 | day 21 | 46571 | 10011 | 4060 | 2.46 |
| | day 28 | 38035 | 10277 | 3927 | 2.62 |
| reassembled | day 14 | 3985 | <25 | 1530 | 0.016 |
| Qβ-mIL-5 | day 21 | 19057 | <25 | 7107 | 0.0035 |
| (cont. poly-L-glutamic acid) | day 28 | 19909 | <25 | 7016 | 0.0035 |

TABLE 4 shows that both the prior art-Qβ-mouse-IL-5 and the reassembled Qβ-mouse-IL-5 induced antibodies specific for murine IL-5. The prior art Qβ-IL-5 induced a Th1 type of immune response with a high IgG2a titre. The average ratio of IgG2a/IgG1 titers was about 2.5. Instead, immunizing mice with a Qβ-mouse-IL-5 vaccine which was made out of QβVLP that was reassembled in the presence of poly-L-glutamic acid, drastically reduced the IgG2a titer, resulting in an average ratio of 0.0077. These data show that the immune responses induced by the reassembled Qβ-mIL-5, containing poly-L-glutamic acid, have shifted from a Th1 immune response to a more Th2 response, as compared with the immune response induced by the prior art Qβ-mIL-5. Note, that sera from 5 mice (each group consisted of 5 mice) were pooled for ELISA analysis.

Consistently, the anti-Qβ titres show the same immune response against the VLP. Using prior art Qβ VLP induces a Th1 type of immune response against Qβ with a high IgG2a titre. In contrast, by using Qβ VLPs reassembled in the presence of poly-L-glutamic acid, a more Th2 type of immune response against Qβ is induced (data not shown).

Eosinophilia Model

An experimental asthma model of allergic airway inflammation is used to assess the effects of vaccination on eosinophilia. Balb/c mice (5 per group) are immunised with the reassembled Qβ VLP coupled to mouse IL-5 as described above. At day 35 of the vaccination program mice were injected intraperitoneally with 50% g Ovalbumin (OVA) in Alumn (Alu-Gel-S) A third group of 4 mice which received no immunisation, are also injected. After 10 days (i.e. day 33) the mice received 100 μg OVA in PBS administered intranasally each day for 4 days. 24 hours after the last challenge the mice are sacrificed and the lungs washed with PBS. The cells contained in the broncho alveolar lavage (BAL) are stained with Maigrünwald-Giemsa and the number of eosinophil cells are counted (Trifilieff A, et al. Clin Exp Allergy. 2001 June; 31(6):934-42).

Example 21

Coupling Gastrin Fragments to the Reassembled Qβ VLP

The following gastrin fragments with fused linker sequence are chemically synthesized according to standard procedures.

```
                                            (SEQ ID NO: 72)
G17(1-9)C2:
pEGPWLEEEESSPPPPC (SEQ ID NO: 73)
c1G17:
pEGPWLEEEEEAYGWMDFGGC (SEQ ID NO: 74)
nG17amide:
CGGQGPWLEEEEEAYGWMDFCONH2

(SEQ ID NO: 54)
nG17-G:
CGGQGPWLEEEEEAYGWMDFG (SEQ ID NO: 75)
nG34amide:
CGGQLGPQGPPHLVADPSKKQGPWLEEEEEAYGWMDFCONH2

(SEQ ID NO: 76)
nG34-G:
CGGQLGPQGPPHLVADPSKKQGPWLEEEEEAYGWMDFG
```

A solution of 2 ml of 2.0 mg/ml reassembled Qβ VLP in 20 mM Hepes, 150 mM NaCl pH 7.2 is reacted for 60 minutes with 114.4 μl of a SMPH (Pierce) solution (from a 50 mM stock solution dissolved in DMSO) at 25° C. The reaction solution is subsequently dialyzed twice for 2 hours against 2 L of 20 mM Hepes, 150 mM NaCl, pH 7.2 at 4° C.

The dialysed, derivatized Qβ VLP is subsequently used to couple c1G17. Briefly, 1 ml of derivatized Qβ VLP (at a concentration of 2 mg/ml) was reacted with 167 μl of a 10 mM peptide solution in DMSO and 100 μl of acetonitril for 2 hours at 15° C. The coupling reactions are then centrifuged at 16 100 rcf for 5 minutes and the supernatants are collected and dialyzed once for 2 hours and then overnight against 2 L of 20 mM Hepes, 150 mM NaCl, pH 7.2 at 4° C. The coupled product was termed Qβ-c1G17. Under substantially the same conditions are nG17amide, nG17-G, nG34amide and nG34-G coupled to the reassembled Qβ VLP.

Example 22

Immunization of Mice with Qβ-c1G17, Qβ-nG17amide, Qβ-nG17-G, Qβ-nG34amide, Qβ3-nG34-G, Qβ-G17(1-9)C2 and DT-G17(1-9)C2 and Detection Antibody Titers by ELISA Adult female C57BL/6 mice are vaccinated with either Qβ-c1G17 (5 mice per group), Qβ-nG17amide, Qβ-nG17-G, Qβ-nG34amide or Qβ-nG34-G (3 mice per group)). 50 μg of Qβ-c1G17 or 25 μg of Qβ-nG17amide, Qβ-nG17-G, Qβ-nG34amide and Qβ-nG34-G (obtained in EXAMPLE 21) are diluted in PBS to a volume of 200 μl and injected subcutaneously (100 μl on two ventral sides) on days 0 and 14. The vaccines are administered without adjuvant. As a control, a group of mice is injected with 50 μg of reassembled Qβ. Mice immunized with Qβ—C1G17 are bled retro-orbitally on day 0, 14, 21, 28, 42, 69, and 101 and mice which are immunized with Qβ-nG17amide, Qβ-nG17-G, Qβ-nG34amide and Qβ-nG34-G are bled retro-orbitally on day 0, 14, 21, 28, 42, 56, and 77.

5 mg/ml RNase and 0.2 mM SPDP (final concentration) are incubated for 1 h at RT. The RNase-SPDP solution is purified over a PD10 column (Amersham). After purification, 10 mM EDTA and 1 mM peptide is added to the RNase-SPDP solution.

ELISA plates (96 well MAXIsorp, NUNC) are coated with RNase-coupled c1G17 or nG17amide, nG17-G, nG34smide, nG34-G at a concentration of 10 μg/ml in coating buffer (0.1 M NaHCO3, pH 9.6), over night at 4° C. After washing the plates in wash buffer (PBS-0.05% Tween), the plates are blocked with blocking buffer (2% BSA-PBS-Tween 20 solution) for 2 h at 37° C. and then washed again and incubated with serially diluted mouse sera. As a control, pre-immune serum of the same mice is also tested. Plates were incubated at RT for 2 h. After further washing, bound antibodies are detected with a HRPO-labeled, Fc specific, goat anti-mouse IgG antibody (Jackson Immunoresearch) and incubated for 1 h at RT. After further washing, plates are developed with OPD solution (1 OPD tablet, 25 ul OPD buffer and 8 μl $H_2O_2$) for 6 minutes and the reaction was stopped with 5% $H_2SO_4$ solution. Plates are read at 450 nm on an ELISA reader (Biorad Benchmark). ELISA titers are expressed as serum dilutions which lead to half maximal OD in the ELISA assay.

Example 23

Coupling of CXCR4 Fragments to Prior Art and Reassembled Qβ VLP

CXCR4 fragment 1-39 (SEQ ID NO:66) with a CGG or GGC linker sequence fused to either the N- or the C-terminus of the CXCR4 fragment 1-39, and CXCR4 fragment 176-185 (SEQ ID NO:65) which was cyclized by connecting a C which was added at the N-terminus with a G which was added at the C-terminus were chemically synthesized according to standard procedures (Peter Henklein, Charité, Berlin, Germany).

A solution of 3 ml (1.0 mg/ml) prior art or reassembled Qβ VLP in 20 mM Hepes, pH 7.2 is reacted for 30 minutes with 85 µl SMPH (50 mM in DMSO, Pierce) at 25° C. The reaction is then dialyzed twice for 2 hours against 3 L of 20 mM Hepes, pH 7.2 at 4° C. The dialysed, derivatized prior art Qβ or reassembled VLP is subsequently used to couple peptides CXCR4-CGG-1-39, CXCR4-1-39-GGC, or CXCR4-C-176-185-G. Briefly, 1 ml of derivatized prior art or reassembled Qβ VLP at a concentration of 1 mg/ml is reacted with 70 µl of a 5 mM peptide solution for 2 hours at 25° C. in 20 mM Hepes, pH 7.2. The coupling reactions are then centrifuged at 13000 rpm for 5 minutes and the supernatants are collected and dialyzed once for 2 hours and then overnight against 1 L of 20 mM Hepes, pH 7.2 at 4° C.

Example 24

Immunization of Mice with Qβ-CXCR4-CGG-1-39, Qβ-CXCR4-1-39-GGC, or Qβ-CXCR4-C-176-185-G and Detection Of Antibody Subtypes Adult female, C57BL/6 mice (3 per group) are vaccinated with the either the prior art or the reassembled Qβ VLP coupled to the CXCR4 fragments (obtained in EXAMPLE 23), using the prior art or reassembled Qβ VLP only as a control. 100 µg of dialyzed vaccine from each sample are diluted in PBS to a volume of 200 µl and injected subcutaneously (100 µl on two ventral sides) on days 0 and 14. The vaccines are administered without or with adjuvant (Allhydrogel, 1 mg/injection). Mice are bled retro-orbitally on day 14, 21, 28 and IgE titers, total IgG titers and the titer of different subclasses (IgG1, IgG2a) specific for the CXCR4 fragments in mice are determined by ELISA substantially the same as described in EXAMPLE 8.

Example 25

Coupling of CCR5 Fragments to Prior Art or Reassembled Qβ VLP and Immunization of Mice Cyclic peptide ECL2A (SEQ ID NO:61) or PNt (SEQ ID NO:63) with additional amidated Cys at the C terminus were chemically synthesized according to standard procedure.

2 g/l prior art or reassembled Qβ VLP are derivatised with 1.43 mM SMPH (Pierce, Perbio Science) for 30 minutes at 25° C. and then dialysed against 20 mM Hepes pH8, 150 mM NaCl. 1 g/l derivatised Qβ VLPs are dissolved in 20% acetonitrile, 150 mM NaCl, 20 mM phosphate pH7.5. 0.286 mM CCR5 fragments ECL2A or PNt is added and incubated for two hours at 25° C.

Female black 6 mice are primed with 50 µg prior art or reassembled Qβ VLP coupled to CCR5 fragments on day 0, (subcutaneously, in 0.2 ml PBS) and compared to BalbC mice primed with 50 µg prior art or reassembled Qβ VLP only. After boosting with the same vaccines on day 14, the x-Qβ and the α-CCR5 antibody titers are checked by ELISA at day 14 and day 21.

Example 26

Purification of CCR5 Specific Mouse Polyclonal Antibody and its Effect in HIV-Neutralisation Assay Serum from immunised mice (obtained in EXAMPLE 25) is centrifuged for five minutes at 14'000 rpm. The supernatant is loaded on a column of 3.3 ml prewashed protein G sepharose (Amersham Biosciences). The column is then washed with PBS and eluted with 100 mM glycine pH2.8. 1 ml fractions are collected in tubes previously provided with 100 µl 1M Tris pH8. Peak fractions absorbing at 280 nm are pooled.

The CCR5 co-receptor specific strains, JR-FL and SF162, have been described previously (O'Brien et al., Nature 1990, 348, page 69; and Shioda et al., Nature 1991, 349, page 167). The HIV-1 inoculums in stock solution are adjusted to contain approximately 1,000 to 4,000 $TCID_{50}$/ml in assay medium ($TCID_{50}$: 50% tissue culture infective dose). Stimulated primary CD8 depleted PBMC (for HIV neutralisation assays)

Briefly, buffy coats obtained from 3 healthy blood donors are depleted of CD8+ T cells using Rosette Sep cocktail (StemCell Technologies Inc., BIOCOBA AG, Switzerland) and PBMC isolated by Ficoll-Hypaque centrifugation (Amersham-Pharmacia Biotech). Cells are adjusted to $4 \times 10^6$/ml in culture medium (RPMI 1640, 10% FCS, 100 U/ml IL-2, glutamine and antibiotics), divided into three parts and stimulated with either 5 µg/ml phytohemagglutinin (PHA), 0.5 µg/ml PHA or anti-CD3 MAb OKT3. After 72 h, cells from all three stimulations are combined and used as source of stimulated CD4+ T cells for infection and virus neutralisation experiments.

Briefly, cells are incubated with serial dilutions of purified polyclonal mouse IgG or control antibody 2D7 (25 µg/ml-25 ng/ml; Pharmingen) in 96-well culture plates for 1 h at 37° C. Then virus inoculum (100 $TCID_{50}$; 50% tissue culture infective dose; Trkola et al., J. Virol., 1999, page 8966) is added and plates cultured for 4-14 days. The total infection volume is 200 µl. Preferably on day 6 post infection, the supernatant medium is assayed for the HIV-1 p24 antigen production by using an immunoassay, as described previously (Moore et al., 1990. Science 250, page 1139).

Example 27

Coupling Bradykinin (BK) and Des-Arg-Bradykinin (Des-Arg9-BK) to Prior Art and Reassembled Qβ VLP Bradykinin (BK) (SEQ ID NO:55) and des-Arg9-Bradykinin (SEQ ID NO:56) with a Cys fused to the N-terminus of both sequences or Bradykinin (BK) with a Cys fused to the C-terminus were chemically synthesized according to standard procedures.

Solution of 3 ml (1.0 mg/ml) prior art or reassembled Qβ VLP in 20 mM Hepes, pH 7.2 was reacted for 30 minutes with 84 µl SMPH (50 mM in DMSO, Pierce) at 25° C. The reaction was then dialyzed twice for 2 hours against 3 L of 20 mM Hepes, pH 7.2 at 4° C. The dialysed, derivatized Qβ VLP was subsequently used to couple Bradykinin or des-Arg9-Bradykinin. Briefly, 3 ml of derivatized prior art or reassembled Qβ VLP at a concentration of 1 mg/ml were reacted with 42 µl of a 50 mM Bradykinin or des-Arg-Bradykinin for 2 hours at 25° C. in 20 mM Hepes, pH 7.2. The coupling reactions were then centrifuged at 13000 rpm for 5 minutes and the supernatants were collected and dialyzed once for 2 hours and then overnight against 3 L of 20 mM Hepes, pH 7.2 at 4° C.

Example 28

Immunization of Mice with Qβ-BK and Qβ-des-Arg9-BK and Detection of Antibody Subtypes Adult female, C57BL/6 mice (10 per group) were vaccinated with either Qβ-BK or Qβ-des-Arg9-BK coupled to prior art or reassembled Qβ VLP (obtained from EXAMPLE 27). 50 μg of dialyzed vaccine from each sample were diluted in PBS to a volume of 200 μl and injected subcutaneously (100 μl on two ventral sides) on days 0, 14 and 28. The vaccine was administered without adjuvant. As a control, a group of 5 mice was injected with PBS. Mice were bled retro-orbitally on day 0, 14, 21 and 33.

The determination of total IgG titers and the titer of different subclasses (IgG1, IgG2a) specific for prior art or reassembled Qβ VLP, and to TNFα in sera were determined by ELISA substantially the same as described in EXAMPLE 8. The ELISA serum titer (TABLE 5 and 6) was defined as the reciprocals of the dilution needed to achieve 50% of the optical density measured at saturation.

TABLE 5 Average anti-prior art Qβ, anti-reassembled Qβ, anti-BK and anti-des-Arg9-BK specific tIgG, IgG2a and IgG1 (expressed as a dilution factor) in mice immunized on day 0 and 14 and 28 with prior art Qβ, reassembled Qβ, Qβ-BK or Qβ-des-Arg9-BK respectively. This data showed that the reassembled Qβ VLPs, either uncoupled or coupled to an antigen have shifted from a more Th1 immune response to a more Th2 response, as compared with the immune response induced by the prior art Qβ VLPs either uncoupled or coupled to an antigen.

cloned in the same restriction sites into the vector pAP405-61 (as described in EXAMPLE 1 of U.S. provisional application 60/611,308) under the control of *E. coli* tryptophan operon promoter. The resulting plasmid is: AP205 coat protein—GTAGGGSG (SEQ ID NO:94)- FGFPEHLLVDFLQSLS (SEQ ID NO:125).

AP205-11-CETP 1 protein is expressed and purified substantially the same as described in WO04/007538. Further steps to remove *E. coli* RNA packaged inside the AP205 VLP is substantially the same as described in EXAMPLE 5 above.

Example 30

Chemically Coupling of CETP Peptide CETP1 to Reassembled Qβ VLP

The CETP fragment (SEQ ID NO:69) with additional CGG linker fused to the N-terminus was synthesized by solid phase chemistry at EMC microcollections GmbH (Germany). The peptide was amidated at its C-terminus.

A solution of 2 ml (2.0 mg/ml) reassembled Qβ VLP (obtained in EXAMPLE 4) in 20 mM Hepes, 150 mM NaCl pH 7.4 is reacted for 30 minutes with 57 μl of SMPH solution (50 mM stock in DMSO, Pierce) at 25° C. The reaction is then

| | immunisation | | | | | | | | |
|---|---|---|---|---|---|---|---|---|---|
| | Qβ-des-Arg9-BK (50 ug/mouse) | | | QβGlu-des-Arg9-BK (50 ug/mouse) | | | QβGlu-des-Arg9-BK (500 ug/mouse) | | |
| | Time after the first Immunisation (days) | | | | | | | | |
| Ab-subtypes | 14 | 28 | 35 | 14 | 28 | 35 | 14 | 28 | 35 |
| tIgG | 1644 | 10366 | 10566 | 317 | 2800 | 5006 | 1166 | 10250 | 13634 |
| IgG2a | 234 | 1295 | 1364 | <100 | <100 | <100 | <100 | <100 | <100 |
| IgG1 | <100 | 151 | 238 | <100 | 540 | 910 | 124 | 1417 | 1898 |

TABLE 6

| | immunisation | | | | | | | | |
|---|---|---|---|---|---|---|---|---|---|
| | Qβ (50 ug/mouse) | | | QβGlu (50 ug/mouse) | | | QβGlu (500 ug/mouse) | | |
| | Time after the first Immunisation (days) | | | | | | | | |
| Ab-subtypes | 14 | 28 | 35 | 14 | 28 | 35 | 14 | 28 | 35 |
| tIgG | 33684 | 106039 | 113380 | 3234 | 55855 | 48850 | 6496 | 61149 | 51605 |
| IgG2a | 5548 | 18881 | 18765 | <100 | 669 | 779 | 138 | 588 | 697 |
| IgG1 | 357 | 1723 | 1699 | <100 | 3591 | 4372 | 194 | 2606 | 3633 |

This data showed that the reassembled Qβ VLPs, either uncoupled or coupled to an antigen have shifted from a more Th1 immune response to a more Th2 response, as compared with the immune response induced by the prior art Qβ-mTNF shifted the immune responses from Th1 to Th2.

Example 29

Cloning, Expression and Purification of CETP Fragment Fused to the C-Terminus of AP205 VLP The DNA fragment coding for the CETP fragment (SEQ ID NO:69) is created by annealing two complementary oligonucleotides encoding the CETP fragment and containing Kpn2I and Mph1103I restriction sites, respectively. The obtained fragment is digested with Kpn2I and Mph1103I and dialyzed twice for 2 hours against 2 L of 20 mM Hepes, pH 7.2 at 4° C. The dialysed, derivatized reassembled Qβ VLP is subsequently used to couple the CETP fragment. Briefly, 1 ml of derivatized reassembled QβVLP at a concentration of 2 mg/ml is reacted with 100 μl of a 50 mM peptide solution for 2 hours at 15° C. in 20 mM Hepes, 150 mM NaCl, pH 7.4. The coupling reactions are then centrifuged at 16000 g for 5 minutes and the supernatants are collected and dialyzed twice for 2 hours against 2 L of 20 mM Hepes, pH 7.4 at 4° C.

Example 31

Test of CETP Vaccines in the Cholesterol Fed Rabbit Model of Atherosclerosis

New Zealand White rabbits (n=12 per group) are vaccinated subcutaneously with 200 μg of VLP-CETP fragment vaccine or VLP as obtained either from EXAMPLE 30 or from EXAMPLE 29 on day 0, and boosted on week 3, 6, 9, 12, 15, 19, 23 and 27. The rabbits are placed on a high cholesterol diet (0.25%) on week 16 and maintained on this diet for another 16 weeks. Plasma samples from fasted rabbits are collected at regular interval for antibody titer, lipoprotein, cholesterol and CETP activity measurements. The animals are sacrificed on week 32 and the aorta removed for atherosclerosis lesion analysis. The aorta are stained with oil red O after "en face" preparation of the Aorta, and the percentage of the aorta covered by lesions is calculated for each animal.

Example 32

Coupling mC5acys to Reassembled Qβ VLPs

The murine C5a amino acid sequence containing an N-terminal CGSGG linker (SEQ ID NO:58, hereafter named mC5acys) was chemically synthesized by Dictagene SA. The C-terminal 19 amino acids of the murine C5a sequence were chemically synthesized (EMC Microcollections GmbH, Germany) with an additional CGG linker at the N-terminus (SEQ ID NO:71, thereafter named mC5acys$^{59-77}$).

A solution of 143 µM reassembled Qβ VLP in 4-(2-Hydroxyethyl) piperazine-1-ethanesulfonic acid (HEPES) buffer (20 mM HEPES, 150 mM NaCl, pH 7.2) is reacted with a 2-fold molar excess (286 µM) of SMPH (Pierce) for 30 minutes at 25° C. with shaking. Reaction products are dialyzed against two changes of Dulbecco's PBS (Gibco) using a dialysis unit with a 10,000 Da molecular weight cutoff (Slide-A-Lyzer, Pierce).

An equimolar amount of mC5acys is added to a 36 µM solution of SMPH-derivatized Qβ VLPs. Reaction volume is 1001 and multiple reactions are performed in parallel. Reactions are incubated for 2 hours at 15° C. with shaking. After coupling, aliquots were centrifuged at 16,000×g for 3 minutes at 4° C. to pellet insoluble material and vaccine is in the soluble fraction.

A 2 fold molar excess amount of mC5acys$^{59-77}$ is added to a 107 µM solution of 5 molar excess SMPH-derivatized Qβ VLPs. Reaction volume is 100 µl and multiple reactions are performed in parallel. Reactions are incubated for 2 hours at 15° C. with shaking. After coupling, aliquots were centrifuged at 16,000×g for 3 minutes at 4° C. to pellet insoluble material. Soluble vaccine is dialysed 2×2 hours against PBS using 10,000 MW cutoff dialysis cassette.

Example 33

Immunization Mice with Qβ-mC5acys VLP in a Collagen-Induced Arthritis Model

Male 6 week old DBA/1JCr1 mice (Charles River, Deutschland) are immunized subcutaneously on the flanks with either 50 µg reassembled Qβ-mC5acys (n=8) or 30 µg reassembled Qβ VLP only (n=8), both diluted in Dulbecco's PBS. Two further booster immunizations are given subcutaneously, on days 15 and 24 after the initial immunization. Anti-mC5acys antibody titers are measured by ELISA. Mice are immunized intradermally at the base of the tail twice on days 35 and 57 after the initial immunization with 100 µg bovine type II collagen (MD Biosciences) emulsified using glass syringes as a 1:1 ratio in Complete Freund's Adjuvant (CFA). The mice are then monitored for the induction and severity of collagen-induced arthritis by daily measurements of fore and hind limb joint thickness and by the daily estimation of joint clinical scores. Joint thickness is measured using constant-tension calipers.

Example 34

Immunization of Mice with Qβ-CCR5 Fragments and Detection of Antibody Subtypes

Adult female, C57BL/6 mice (3 per group) are vaccinated with the either prior art or reassembled Qβ VLP coupled to the CCR5 fragments (obtained in EXAMPLE 25), using the prior art or reassembled Qβ VLP as a control. 100 µg of dialyzed vaccine from each sample are diluted in PBS to a volume of 200 µl and injected subcutaneously (100 µl on two ventral sides) on days 0 and 14. The vaccines are administered without or with adjuvant (Allhydrogel, 1 mg/injection). Mice are bled retro-orbitally on day 14, 21, 28 and IgE titers, total IgG titers and the titer of different subclasses (IgG1, IgG2a) specific for the CCR5 fragments in mice are determined by ELISA.

Microtiter plates (Maxisorp, Nunc) are coated overnight with 10 µg/ml CCR5 fragments coupled to RNAse. The determination of total IgG titers and the titer of different subclasses (IgG1, IgG2a) specific for prior art or reassembled Qβ VLP, and to TNFα in sera are determined by ELISA substantially the same as described in EXAMPLE 8.

Example 35

Efficacy of Vaccination Against Qβ-BK, Qβ-Des-Arg9-BK for the Treatment of Collagen-Induced Arthritis The efficacy of reassembled Qβ-BK or Qβ-des-Arg9-BK is tested in the murine collagen-induced arthritis (CIA) model. 10 Male DBA/1 mice per group are immunized intradermally three times (days 0, 14 and 28) with 50 µg of Qβ-BK, Qβ-des-Arg9-BK or Qβalone. Then mice are injected twice intradermally (days 34 and 55) with 200 µg bovine type II collagen mixed with complete Freund's adjuvant.

After the second collagen/CFA injection mice are examined on a regular basis and a clinical score ranging from 0 to 3 is assigned to each limb according to the degree of reddening and swelling observed. Three weeks after the second collagen/CFA injection the average clinical score per limb is determined in the three experimental groups.

Example 36

Efficacy of Vaccination Against Qβ-BK and Qβ-Des-Arg9-BK for the Treatment of Allergic Airway Inflammation (AAI)

An experimental asthma model of allergic airway inflammation is used to assess the effects of vaccination against Bradykinin (BK) and des-Arg9-Bradykinin (des-Arg9-BK) on Th2-mediated immune responses characterized by: eosinophil influx into the lung, cytokine (IL-4, IL-5, IL-13) production, IgE antibody and mucous production and broncho hyper-responsiveness (BHR). Balb/c mice (5 per group) are immunised with either Qβ-BK or Qβ-des-Arg9-BK as described in EXAMPLE 15 or injected with Qβ alone. 35 days after the first immunisation, mice are injected intraperitonealy with 50% g ovalbumin (OVA) in the presence or absence of adjuvant (Alhydrogel, 1 mg AlOH/injection). 10 days later (i.e. day 45) all mice are daily intranasally challenged with 50 µg OVA in PBS on 4 consecutive days. 24 hours after the last challenge BHR is determined with a whole body phlegtismograph. Then mice are sacrificed at specific time points to analyze lung inflammation and Th2-mediated immune responses. Lung lavages are performed with PBS/ 1% BSA. The cells contained in the broncho alveolar lavage (BAL) are counted in a Coulter Counter (Instrumenten Gesellschaft AG) and differentiated with Maigrünwald-Giemsa staining as previously described (Trifilieff A, et al. Clin Exp Allergy. 2001 June; 31(6):934-42).

The invention claimed is:

1. A composition comprising:
   (a) a virus-like particle (VLP) comprising coat proteins, mutants or fragments thereof, of an RNA-bacteriophage with at least one first attachment site, wherein said VLP is recombinantly produced by a host, and said VLP is essentially free of host RNA;
   (b) at least one antigen with at least one second attachment site; wherein said at least one antigen is linked to said VLP (a) through said at least one first attachment site and said at least one second attachment site; and
   (c) at least one polyanionic macromolecule packaged inside said VLP, wherein said at least one polyanionic macromolecule is a polyanionic polypeptide selected from the group consisting of:
   (i) polyglutamic acid;
   (ii) polyaspartic acid;
   (iii) poly(GluAsp); and
   (iv) chemical modifications of (i)-(iii), wherein said modifications are glycosylations, acetylations or phosphorylations;
wherein said polyanionic polypeptide does not statistically significantly activate a Toll-like receptor.

2. The composition of claim 1, wherein the molecular weight of said polyanionic macromolecule is from 10,000 to 100,000 Daltons.

3. The composition of claim 1, wherein said polyanionic polypeptide is polyglutamic acid and/or polyaspartic acid.

4. The composition of claim 1, wherein said RNA-phage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (j) bacteriophage f2;
   (k) bacteriophage PP7; and
   (l) bacteriophage AP205.

5. The composition of claim 1, wherein said VLP comprises coat proteins, and/or mutants thereof, and/or fragments thereof, of a RNA-phage Qβ, fr, AP205 or GA.

6. The composition of claim 1, wherein said first attachment site is linked to said second attachment site via at least one covalent bond.

7. The composition of claim 1, wherein said first attachment site comprises an amino group.

8. The composition of claim 1, wherein said second attachment site comprises a sulfhydryl group.

9. The composition of claim 1, wherein said first attachment site comprises an amino group of a lysine and said second attachment site comprises a sulfhydryl group of a cysteine.

10. The composition of claim 1 further comprising a linker fused to the N-terminus or the C-terminus of said antigen, wherein said linker comprises said second attachment site, and wherein said linker comprises a cysteine residue.

11. The composition of claim 1, wherein said at least one antigen is selected from the group consisting of:
   (a) polypeptides;
   (b) carbohydrates;
   (c) steroid hormones;
   (d) organic molecules; and
   (e) haptens.

12. The composition of claim 1, wherein said at least one antigen is a self antigen, or a fragment thereof, or a variant thereof.

13. The composition of claim 1, wherein said antigen is selected from the group consisting of:
   (a) lymphotoxins;
   (b) lymphotoxin receptors;
   (c) receptor activator of nuclear factor kB ligand (RANKL);
   (d) vascular endothelial growth factor (VEGF);
   (e) vascular endothelial growth factor receptor (VEGF-R);
   (f) Interleukin-5;
   (g) Interleukin-17;
   (h) Interleukin-13;
   (i) IL-23 p19;
   (j) Ghrelin;
   (k) CCL21;
   (l) CXCL12;
   (m) SDF-1;
   (n) M-CSF;
   (o) MCP-1;
   (p) Endoglin;
   (q) GnRH;
   (r) TRH;
   (s) Eotaxin;
   (t) Bradykinin;
   (u) BLC;
   (v) Tumor Necrosis Factor α;
   (w) amyloid beta peptide (A$\beta_{1-42}$);
   (x) A$\beta_{1-6}$;
   (y) Angiotensin;
   (z) Gastrin and/or progastrin;
   (aa) CETP;
   (bb) CCR5;
   (cc) C5a;
   (dd) CXCR4;
   (ee) Des-Arg-Bradykinin;
   (ff) GnRH peptide;
   (gg) angiotensin peptide;
   (hh) TNF-peptide;
   (ii) a fragment of the aforementioned antigens (a) to (hh); and
   (jj) a variant of the aforementioned antigens (a) to (hh).

14. An immunogenic composition comprising the composition of claim 1, wherein said immunogenic composition is devoid of an adjuvant.

15. An immunogenic composition comprising the composition of claim 1, wherein said immunogenic composition further comprises at least one adjuvant.

16. A method of inducing an immune response comprising administering the immunogenic composition of claim 14 or claim 15 to an animal or human.

17. A pharmaceutical composition comprising:
   (a) the composition of claim 1; and
   (b) an acceptable pharmaceutical carrier.

18. The composition of claim 1, wherein said polyanionic polypeptide is a polyglutamic acid.

19. The composition of claim 1, wherein said first attachment site is linked to said second attachment site via at least one non-peptide covalent bond.

20. The composition of claim 1, wherein said VLP is a VLP of an RNA-bacteriophage.

21. The composition of claim 1, wherein said VLP is a VLP of RNA-bacteriophage Qβ.

22. The composition of claim 21, wherein said VLP of RNA-bacteriophage Qβ comprises one or more recombinant proteins having the amino acid sequence as set forth in SEQ ID NO:10.

23. The composition of claim 21, wherein said VLP of RNA-bacteriophage Qβ comprises one or more recombinant coat proteins consisting of the amino acid sequence as set forth in SEQ ID NO:10.

24. The composition of claim 23, wherein said first attachment site is linked to said second attachment site via at least one non-peptide covalent bond.

25. The composition of claim 24, wherein said first attachment site comprises an amino group of a lysine and said second attachment site comprises a sulfhydryl group of a cysteine.

26. The composition of claim 25, wherein said polyanionic polypeptide is a polyglutamic acid.

27. The composition of claim 26, wherein said antigen is Interleukin-17.

28. The composition of claim 26, wherein said antigen is Tumor Necrosis Factor α.

29. The composition of claim 26, wherein said polyglutamic acid is a polypeptide consisting of glutamic acid molecules with a molecular weight between 10,000 and 100,000 Dalton.

30. The composition of claim 29, wherein said at least one antigen is a self antigen, or a fragment thereof, or a variant thereof.

31. The composition of claim 30, wherein said self antigen is Interleukin-17.

32. The composition of claim 30, wherein said self antigen is Tumor Necrosis Factor α.

* * * * *